United States Patent
Wehner et al.

(10) Patent No.: US 6,399,643 B1
(45) Date of Patent: *Jun. 4, 2002

(54) SPIROIMIDAZOLIDINE DERIVATIVES, THEIR PREPARATION, THEIR USE AND PHARMACEUTICAL PREPARATIONS FORMED THEREFROM

(75) Inventors: Volkmar Wehner, Sandberg; Hans Ulrich Stilz; Wolfgang Schmidt, both of Frankfurt; Dirk Seiffge, Mainz-Kostheim, all of (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/572,273

(22) Filed: May 17, 2000

(30) Foreign Application Priority Data

May 17, 1999 (DE) ......................................... 199 22 462

(51) Int. Cl.[7] .................. A61K 31/4184; C07D 235/02
(52) U.S. Cl. ...................... 514/397; 514/398; 548/301.4
(58) Field of Search ........................ 548/301.4; 514/397, 514/398

(56) References Cited

U.S. PATENT DOCUMENTS

| | | | |
|---|---|---|---|
| 5,389,614 A | 2/1995 | Koenig et al. | 514/18 |
| 5,397,796 A | 3/1995 | Zoller et al. | 514/389 |
| 5,424,293 A | 6/1995 | Zoller et al. | 514/20 |
| 5,554,594 A | 9/1996 | Zoller et al. | 514/18 |
| 5,658,935 A | 8/1997 | Klinger et al. | 514/359 |
| 5,686,421 A | 11/1997 | Koenig et al. | 514/18 |
| 5,981,492 A | 11/1999 | Zoller et al. | 514/20 |

FOREIGN PATENT DOCUMENTS

| | | |
|---|---|---|
| EP | 0 796 855 | 9/1997 |
| EP | 0 842 943 | 11/1997 |
| EP | 0 842 944 | 11/1997 |
| EP | 0 842 945 | 11/1997 |
| EP | 0 903 353 | 3/1999 |
| EP | 0 905 139 | 3/1999 |
| EP | 0 918 059 | 5/1999 |
| WO | 93/13798 | 7/1993 |
| WO | 93/15764 | 8/1993 |
| WO | 93/18057 | 9/1993 |
| WO | 94/15958 | 7/1994 |
| WO | 94/16094 | 7/1994 |
| WO | 94/17828 | 8/1994 |
| WO | 95/14008 | 5/1995 |
| WO | 95/15973 | 6/1995 |
| WO | 95/19790 | 7/1995 |
| WO | 96/00581 | 1/1996 |
| WO | 96/06108 | 2/1996 |
| WO | 96/20216 | 7/1996 |
| WO | 98/22966 | 8/1996 |
| WO | 97/03094 | 1/1997 |
| WO | 98/04247 | 2/1998 |
| WO | 98/04913 | 2/1998 |
| WO | 98/42656 | 10/1998 |
| WO | 99/60015 | 11/1999 |

OTHER PUBLICATIONS

Cronstein, Bruce N. et al., "The Adhesion Molecules of Inflammation". *Arthritis and Rheumatism*, vol. 36(2); pp. 147–157(1993).A52.

Elices, Mariano J. et al., "VCAM–1 on Activated Endothelium Interacts with the Leukocyte Integrin VLA–4 at a Site Distinct from the VLA–4/Fibronectin Binding Site". *Cell*, vol. 60; pp. 577–584(1990).

Foster, Carolyn A. et al., "VCAM–1/α4–integrin adhesion pathway: Therapeutic target for allergic inflammatory disorders". *Jour. Allergy Clin. Immunol.*, vol. 96(6); pp. S270–S277(1996).

Kilger et al., "Molecular analysis of the physiological and pathophysiological role of α4–integrins". *J. Mol. Med.*, vol. 73; pp. 347–354(1995).

McMurray, Robert, W., "Adhesion Molecules in Autoimmune Disease", Seminars in Arthritis and Rheumatism, vol. 25(4); pp 215–233(1996).

(List continued on next page.)

Primary Examiner—Laura L. Stockton
(74) Attorney, Agent, or Firm—Heller Ehrman White and McAuliffe

(57) ABSTRACT

The present invention relates to spiroimidazolidine derivatives of the formula I

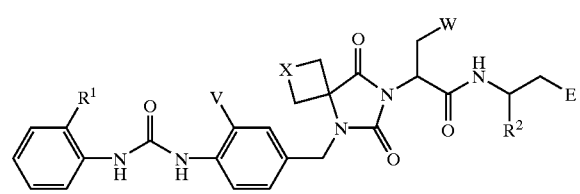

in which E, V, W, X, $R^1$ and $R^2$ have the meanings indicated in the claims. The compounds of the formula I are valuable pharmaceutical active compounds which are suitable, for example, for the therapy and prophylaxis of inflammatory disorders, such as, for example, rheumatoid arthritis, or allergic disorders. The compounds of the formula I are also inhibitors of the adhesion and migration of leukocytes and/or antagonists of the adhesion receptor VLA-4 belonging to the integrins group. They are generally suitable for the therapy and prophylaxis of illnesses which are caused by an undesired extent of leukocyte adhesion and/or leukocyte migration or are associated therewith or in which cell-cell or cell-matrix interactions which are based on interactions of VLA-4 receptors with their ligands play a part. The invention also relates to processes for the preparation of the compounds of the formula I, pharmaceutical preparations which contain compounds of the formula I, and methods for treating these disorders.

17 Claims, No Drawings

OTHER PUBLICATIONS

Albelda, S., et al., "Molecular and Cellular Properties of PECAM-1 (endoCAM/CD31): A Novel Vascular Cell–Cell Adhsion Molecule", Journal of Cell Biology, vol. 114, No. 5, pp 1059–1068, 1991.

Issekutz, Thomas B. et al., Rat Blood Neutrophils Express Very Late Antigen 4 and it Mediates Migration to Arthritic Joint and Dermal Inflammation. J. Exp. Med., vol. 183; pp 2175–2184(1996).

Damle, N., et al., "Vascular Cell Adhesion Molecule 1 Induces T–cell Antigen Receptor–Dependent Activation of CD4+T Lymphocytes," Proc. Nat'l. Acad. Sci. USA, vol. 88, pp. 6403–6407 (1991).

Davies, S., et al., "Asymmetric Synthesis of R–β–Amino Butanoic Acid and S–β–Tyrosine: Homochiral Lithium Amide Equivalents for Michael Additions to α,β–Unsaturated Esters," Tetrahedron: Asymmetry, vol. 2, No. 3, pp. 183–186 (1991).

Elices, M.J., et al., "The Integrin VLA–4 Mediates Leukocyte Recruitment to Skin Inflammatory Sites In Vivo," Clinical and Experimental Rheumatology, vol. 11, Supp. 8, pp. S77–S80 (1993).

Elices, M.J., et al., "Expression and Functional Significance of Alternatively Spliced CS1 Fibronectin in Rheumatoid Arthritis Microvasculature," J. Clin. Invest., vol. 93, pp. 405–416 (1994).

Elices, M.J., "The Integrin $\alpha_4\beta_1$ (VLA–4) As a Therapeutic Target," Ciba Foundation Symposium, vol. 189, pp. 79–90 (1995).

Fleisher, D., et al., "Improved Oral Drug Delivery: Solubility Limitations Overcome by the Use of Prodrugs," Advanced Drug Delivery Reviews, vol. 19, pp. 115–130 (1996).

Freedman, A., et al., "Follicular Non–Hodgkin's Lymphoma Cell Adhesion to Normal Germinal Centers and Neoplastic Follicles Involves Very Late Antigen–4 and Vascular Cell Adhesion Molecule–1," Blood, vol. 79, No. 1, pp. 206–212 (1992).

Goldschmidt, V.S., et al., "Über Peptid–Synthesen I," Liebigs. Ann. Chem., vol. 575, pp. 217–231 (1952).

Harlan, J., "Leukocyte–Endothelial Interactions," Blood, vol. 65, No. 3, pp. 513–525 (1985).

Isobe, M., et al, "Effect of Anti–VCAM–1 and Anti–VLA–4 Monoclonal Antibodies on Cardiac Allograft Survival and Response to Soluble Antigens in Mice," Transplantation Proceedings, vol. 26, No. 2, pp. 867–868, (1994).

Issekutz, T., "Inhibition of In Vivo Lymphocyte Migration to Inflammation and Homing to Lymphoid Tissues by the TA–2 Monoclonal Antibody," Journal of Immunology, vol. 147, No. 12, pp. 4178–4184 (1991).

Kuijpers, T., "Pathophysiological Aspects of VLA–4 Interactions and Possibilities for Therapeutic Interventions," Springer Seminars in Immunopathology, vol. 16, pp. 379–389 (1995).

Laffon, A., et al., "Upregulated Expression and Function of VLA–4 Fibronectin Receptors on Human Activated T–Cells in Rheumatoid Arthritis," J. Clin. Invest., vol. 88, pp. 546–552 (1991).

Morales–Ducret, J., et al., "$\alpha_4/\beta_1$ Integrin (VLA–4) Ligands in Arthritis: Vascular Cell Adhesion Molecule–1 Expression in Synovium and on Fibroblast–Like Synoviocytes," Journal of Immunology, vol. 149, No. 4, pp. 1424–1431 (1992).

Muacevic, G., "New Apparatus and Method for the Toxicological Investigation of Metered Aerosols in Rats," Arch. Toxicol., vol. 34, pp. 1–8 (1975).

Nowick, J., et al., "Synthesis of Peptide Isocyanates and Isothiocynates," J. Org. Chem, vol. 61, p. 3929–3934 (1996).

O'Brien, K., et al., "Vascular Cell Adhesion Molecule–1 is Expressed in Human Coronary Atherosclerotic Plaques," J. Clin. Invest., vol. 92, pp. 945–951 (1993).

Ockenhouse, C., et al., "Human Vascular Endothelial Cell Adhesion Receptors for *Plasmodium falciparum*–infected Erythrocytes: Roles for Endothelial Leukocyte Adhesion Molecule 1 and Vascular Cell Adhesion Molecule 1," Journal of Experimental Medicine, vol. 176, pp. 1183–1189 (1992).

Osborn, L., et al., "Direct Expression Cloning of Vascular Cell Adhesion Molecule 1, a Cytokine–Induced Endothelial Protein that Binds to Lymphocytes," Cell, vol. 59, pp. 1203–1211 (1989).

Osborn, L., "Leukocyte Adhesion to Endothelium in Inflammation," Cell, vol. 62, pp. 3–6 (1990).

Postigo, A., et al., Increased Binding of Synovial T. Lymphocytes from Rheumatoid Arthritis to Endothelial–Leukocyte Adhesion Molecule–1 (ELAM–1) and Vascular Cell Adhesion Molecule–1 (VCAM–1), J. Clin.., Invest vol. 89, pp 1445–1452 (1992).

Renkonen, R., et al., "Rapid Communication: Expression of Endothelial Adhesion Molecules In Vivo," American Journal of Pathology, vol. 140, No. 4, pp. 763–767 (1992).

Rice, G., et al., "An Inducible Endothelial Cell Surface Glycoprotein Mediates Melanoma Adhesion," Science, vol. 246, pp. 1303–1306 (1989).

Ruoslahti, E., "Fibronectin and its Receptors," Ann. Rev. Biochem., vol. 57, pp. 375–413 (1988).

Seiffge, D., et al., "Effects of Different Mediators or Cytokines and Monoclonal Antibodies to Adhesion Molecules on Leukocyte Adhesion in Rat Mesenteric Venules," Int. J. Microcirc., vol. 15, pp. 301–308 (1995).

Springer, T., "Traffic Signals for Lymphocyte Recirculation and Leukocyte Emigration: The Multistep Paradigm," Cell, vol. 76, pp. 301–314 (1994).

Stoolman, L., "Adhesion Molecules Controlling Lymphocyte Migration," Cell, vol. 56, pp. 907–910 (1989).

Takeuchi, T., et al., "Upregulated Expression and Function of Integrin Adhesive Receptors in Systemic Lupus Erythematosus Patients with Vasculitis," J. Clin. Invest., vol. 92, pp. 3008–3016 (1993).

Tropp, C., "Einwirkung von Phosgen auf Polypeptidartige Derivate der p–Amino–benzosäure: Bildung von 1.3–substi–tuierten Hydantoinen," Chem. Ber, vol. 61, pp. 1431–1439 (1928).

Yang, X., et al., "Inhibition of Insulitis and Prevention of Diabetes in Nonobese Diabetic Mice by Blocking L–selectin and Very Late Antigen–4 Adhesion Receptors," Proc. Nat'l. Acad. Sci. USA, vol. 90, pp. 10494–10498 (1993).

Yednock, T., et al., "Prevention of Experimental Autoimmune Encephalomyelitis by Antibodies Against $\alpha_4\beta_1$ Integrin," Nature, vol. 356, pp. 63–66 (1992).

Zettlmeissl, G., et al., "Expression and Characterization of Human CD4: Immunoglobulin Fusion Proteins," DNA and Cell Biology, vol. 9, No. 5, pp. 347–353 (1990).

Van Dinther, Janssen, A., et al., "The VLA–4/VCAM–1 Pathway is Involved in Lymphocyte Adhesion to Endothelium in Rheumatoid Synovium," Journal of Immunology, vol. 147, No. 12, pp. 4207–4210 (1991).

Barbadillo, C., et al., "Anti–Integrin Immunotheraphy in Rheumatoid Arthritis: Protective Effect of Anti–α–4 Antibody in Adjuvant Arthritis," Springer Seminars in Immunotheraphy, vol. 16 pp. 427–436 (1995).

Bergelson, J., et al., "Do Integrins Use a 'Midas Touch' to Grasp an Asp?" Current Biology, vol. 5, No. 6, pp. 615–617 (1995).

Bundgaard, H., "Novel Chemical Approaches in Prodrug Design," Drugs of the Future, vol. 16, No. 5, pp. 443–458 (1991).

Davies, S., et al., "Asymmetric Synthesis of anti–α–Alkyl–β–amino Acids", J. Chem. Soc. Perkins Trans 1 pp. 1129–1139 (1994).

SPIROIMIDAZOLIDINE DERIVATIVES, THEIR PREPARATION, THEIR USE AND PHARMACEUTICAL PREPARATIONS FORMED THEREFROM

BACKGROUND OF THE INVENTION

1. Field of the Invention

The present invention relates to spiroimidazolidine derivatives of the formula I

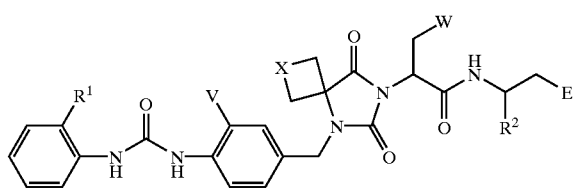

in which E, V, W, X, $R^1$ and $R^2$ have the meanings indicated below. The compounds of the formula I are valuable pharmaceutical active compounds, which are suitable, for example, for the therapy and prophylaxis of inflammatory disorders, for example of rheumatoid arthritis, or of allergic disorders. The compounds of the formula I are inhibitors of the adhesion and migration of leukocytes and/or antagonists of the adhesion receptor VLA-4 belonging to the integrins group. They are generally suitable for the therapy and prophylaxis of illnesses which are caused by an undesired extent of leukocyte adhesion and/or leukocyte migration or are associated therewith or in which cell-cell or cell-matrix interactions which are based on interactions of VLA-4 receptors with their ligands play a part. The invention furthermore relates to processes for the preparation of the compounds of the formula I, their use and pharmaceutical preparations which contain compounds of the formula I.

2. Description of the Related Art

The integrins are a group of adhesion receptors which play an important part in cell-cell-binding and cell-extracellular matrix-binding processes. They have an αβ-heterodimeric structure and exhibit a wide cellular distribution and a high extent of evolutive conservation. The integrins include, for example, the fibrinogen receptor on platelets, which interacts especially with the RGD sequence of fibrinogen, or the vitronectin receptor on osteoclasts, which interacts especially with the RGD sequence of vitronectin or of osteopontin. The integrins are divided into three major groups, the β2 subfamily with the representatives LFA-1, Mac-1 and p150/95, which are responsible in particular for cell-cell interactions of the immune system, and the subfamilies β1 and β3, whose representatives mainly mediate cell adhesion to components of the extracellular matrix (Ruoslahti, Annu. Rev. Biochem. 1988, 57, 375). The integrins of the β1 subfamily, also called VLA proteins (very late (activation) antigen), include at least six receptors which interact specifically with fibronectin, collagen and/or laminin as ligands. Within the VLA family, the integrin VLA-4 (α4β1) is atypical, insofar as it is mainly restricted to lymphoid and myeloid cells and is responsible in these for cell-cell interactions with a large number of other cells. For example, VLA-4 mediates the interaction of T and B lymphocytes with the heparin II-binding fragment of human plasma fibronectin (FN). The binding of VLA-4 with the heparin II-binding fragment of plasma fibronectin is especially based on an interaction with an LDVP sequence. In contrast to the fibrinogen or vitronectin receptor, VLA-4 is not a typical RGD-binding integrin (Kilger and Holzmann, J. Mol. Meth. 1995, 73, 347).

The leukocytes circulating in the blood normally exhibit only a low affinity for the vascular endothelial cells which line the blood vessels. Cytokines which are released from inflamed tissue cause the activation of endothelial cells and thus the expression of a large number of cell surface antigens. These include, for example, the adhesion molecules ELAM-1 (endothelial cell adhesion molecule-1; also designated as E-selectin), which, inter alia, binds neutrophils, ICAM-1 (intercellular adhesion molecule-1), which interacts with LFA-1 (leukocyte function-associated antigen 1) on leukocytes, and VCAM-1 (vascular cell adhesion molecule-1), which binds various leukocytes, inter alia lymphocytes (Osborn et al., Cell 1989, 59, 1203). VCAM-1, like ICAM-1, is a member of the immunoglobulin gene superfamily. VCAM-1 (first known as INCAM-110) was identified as an adhesion molecule that is induced on endothelial cells by inflammatory cytokines such as TNF and IL-1 and lipopolysaccharides (LPS). Elices et al. (Cell 1990, 60, 577) showed that VLA-4 and VCAM-1 form a receptor-ligand pair which mediates the adhesion of lymphocytes to activated endothelium. The binding of VCAM-1 to VLA-4 does not take place here due to an interaction of the VLA4 with an RGD sequence; this sequence is not contained in VCAM-1 (Bergelson et al., Current Biology 1995, 5, 615). VLA-4, however, also occurs on other leukocytes, and the adhesion of leukocytes other than lymphocytes is also mediated via the VCAM-1/VLA-4 adhesion mechanism. VLA-4 thus represents an individual example of a β1 integrin receptor which, via the ligands VCAM-1 and fibronectin, plays an important part both in cell-cell interactions and in cell-extracellular matrix interactions.

The cytokine-induced adhesion molecules play an important part in the recruitment of leukocytes into extravascular tissue regions. Leukocytes are recruited into inflammatory tissue regions by cell adhesion molecules which are expressed on the surface of endothelial cells and serve as ligands for leukocyte cell surface proteins or protein complexes (receptors) (the terms ligand and receptor can also be used vice versa). Leukocytes from the blood must first adhere to endothelial cells before they can migrate into the synovium. Since VCAM-1 binds to cells which carry the integrin VLA-4 (α4β1), such as eosinophils, T and B lymphocytes, monocytes or neutrophils, it and the VCAM-1/VLA-4 mechanism have the function of recruiting cells of this type from the blood stream into areas of infection and inflammatory foci (Elices et al., Cell 1990, 60, 577; Osborn, Cell 1990, 62, 3; Issekutz et al., J. Exp. Med. 1996, 183, 2175).

The VCAM-1/VLA-4 adhesion mechanism has been connected with a number of physiological and pathological processes. Apart from by cytokine-induced endothelium, VCAM-1 is additionally expressed, inter alia, by the following cells: myoblasts, lymphoid dendritic cells and tissue macrophages, rheumatoid synovium, cytokine-stimulated neural cells, parietal epithelial cells of the Bowman's capsule, the renal tubular epithelium, inflamed tissue during heart and kidney transplant rejection and by intestinal tissue in graft-versus-host disease. VCAM-1 is also found to be expressed on those tissue areas of the arterial endothelium which correspond to early arteriosclerotic plaques of a rabbit model. Additionally, VCAM-1 is expressed on follicular dendritic cells of human lymph nodes and is found on stroma cells of the bone marrow, for example in the mouse. The latter finding points to a function of VCAM-1 in B-cell development. Apart from on cells of hematopoietic origin, VLA-4 is also found, for example, on melanoma cell lines, and the VCAM-1/VLA-4 adhesion mechanism is connected with the metastasis of such tumors (Rice et al., Science 1989,246, 1303).

The main form in which VCAM-1 occurs in vivo on endothelial cells and which is the dominant form in vivo is designated as VCAM-7D and carries seven immunoglobulin domains. The domains 4, 5 and 6 are similar in their amino acid sequences to the domains 1, 2 and 3. In a further form consisting of six domains, designated here as VCAM-6D, the fourth domain is removed by alternative splicing. VCAM-6D can also bind VLA-4-expressing cells.

Further details on VLA-4, VCAM-1, integrins and adhesion proteins are found, for example, in the articles by Kilger and Holzmann, J. Mol. Meth. 1995, 73, 347; Elices, Cell Adhesion in Human Disease, Wiley, Chichester 1995, p. 79; Kuijpers, Springer Semin. Immunopathol. 1995,16, 379.

On account of the role of the VCAM-1/VLA-4 mechanism in cell adhesion processes, which are of importance, for example, in infections, inflammations or atherosclerosis, it has been attempted by means of interventions into these adhesion processes to control illnesses, in particular, for example, inflammations (Osborn et al., Cell 1989, 59, 1203). A method of doing this is the use of monoclonal antibodies which are directed against VLA-4. Monoclonal antibodies (mABs) of this type, which as VLA-4 antagonists block the interaction between VCAM-1 and VLA-4, are known. Thus, for example, the anti-VLA-4 mABs HP2/1 and HP1/3 inhibit the adhesion of VLA-4-expressing Ramos cells (B-cell-like cells) to human umbilical cord endothelial cells and to VCAM-1-transfected COS cells. The anti-VCAM-1 mAB 4B9 likewise inhibits the adhesion of Ramos cells, Jurkat cells (T-cell-like cells) and HL60 cells (granulocyte-like cells) to COS cells transfected with genetic constructs which cause VCAM-6D and VCAM-7D to be expressed. In vitro data with antibodies which are directed against the α4 subunit of VLA-4 show that the adhesion of lymphocytes to synovial endothelial cells is blocked, an adhesion which plays a part in rheumatoid arthritis (van Dinther-Janssen et al., J. Immunol. 1991,147, 4207).

In vivo experiments have shown that an experimental autoimmune encephalomyelitis can be inhibited by anti-α4 mAB. The migration of leukocytes into an inflammatory focus is likewise blocked by a monoclonal antibody against the α4 chain of VLA-4. The influencing of the VLA-4-dependent adhesion mechanism by antibodies was also investigated in an asthma model in order to investigate the role of VLA-4 in the recruitment of leukocytes into inflamed lung tissue (WO-A-93/13798). The administration of anti-VLA-4 antibodies inhibited the late-phase reaction and airway overreaction in allergic sheep.

The VLA-4-dependent cell adhesion mechanism was also investigated in a primate model of inflammatory bowel disease (IBD). In this model, which corresponds to ulcerative colitis in man, the administration of anti-VLA-4 antibodies resulted in a significant reduction in the acute inflammation.

Moreover, it was possible to show that VLA-4-dependent cell adhesion plays a part in the following clinical conditions including the following chronic inflammatory processes: rheumatoid arthritis (Cronstein and Weismann, Arthritis Rheum. 1993, 36, 147; Elices et al., J. Clin. Invest. 1994, 93, 405), diabetes mellitus (Yang et al., Proc. Natl. Acad. Sci. USA 1993, 90, 10494), systemic lupus erythematosus (Takeuchi et al., J. Clin. Invest. 1993, 92, 3008), allergies of the delayed type (type IV allergy) (Elices et al., Clin. Exp. Rheumatol. 1993, 11, S77), multiple sclerosis (Yednock et al., Nature 1992, 356, 63), malaria (Ockenhouse et al., J. Exp. Med. 1992, 176, 1183), arteriosclerosis (O'Brien et al., J. Clin. Invest. 1993, 92, 945), transplantation (Isobe et al., Transplantation Proceedings 1994, 26, 867), various malignancies, for example melanoma (Renkonen et al., Am. J. Pathol. 1992,140, 763), lymphoma (Freedman et al., Blood 1992, 79, 206) and others (Albelda et al., J. Cell Biol. 1991, 114,1059).

VLA-4 blocking by suitable antagonists accordingly offers effective therapeutic possibilities, in particular, for example, of treating various inflammatory conditions including asthma and IBD. The particular relevance of VLA-4 antagonists for the treatment of rheumatoid arthritis in this case results, as already stated, from the fact that leukocytes from the blood must first adhere to endothelial cells before they can migrate into the synovium, and that the VLA-4 receptor plays a part in this adhesion. The fact that VCAM-1 is induced by inflammatory agents on endothelial cells (Osborn, Cell 1990, 62, 3; Stoolman, Cell 1989, 56, 907), and the recruitment of various leukocytes into areas of infection and inflammatory foci has already been discussed above. At the same time, T cells adhere to activated endothelium mainly via the LFA-1/ICAM-1 and VLA-4/VCAM-1 adhesion mechanisms (Springer, Cell 1994, 76, 301). On most synovial T cells, the binding capacity of VLA-4 for VCAM-1 is increased in rheumatoid arthritis (Postigo et al., J. Clin. Invest. 1992, 89, 1445). Additionally, an increased adhesion of synovial T cells to fibronectin has been observed (Laffon et al., J. Clin. Invest. 1991, 88, 546; Morales-Ducret et al., J. Immunol. 1992,149, 1424). VLA-4 is upregulated both in the course of its expression and with respect to its function on T lymphocytes of the rheumatoid synovial membrane. The blocking of the binding of VLA-4 to its physiological ligands VCAM-1 and fibronectin makes possible an effective prevention or alleviation of articular inflammatory processes. This is also confirmed by experiments with the antibody HP2/1 on Lewis rats with adjuvant arthritis, in which an effective prevention of illness has been observed (Barbadillo et al., Springer Semin. Immunopathol. 1995, 16, 427). VLA-4 is thus an important therapeutic target molecule.

The abovementioned VLA-4 antibodies and the use of antibodies as VLA-4 antagonists are described in the Patent Applications WO-A-93/13798, WO-A-93/15764, WO-A-94/16094, WO-A-94/17828 and WO-A-95/19790. In the Patent Applications WO-A-94/15958, WO-A-95/15973, WO-A-96/00581, WO-A-96/06108 and WO-A-96/20216, peptide compounds are described as VLA-4 antagonists. The use of antibodies and peptide compounds as pharmaceuticals, however, has some disadvantages, for example lack of oral availability, easy degradability or immunogenic action on longer-term use, and there is thus a need for VLA-4 antagonists having a favorable profile of properties for use in therapy and prophylaxis.

WO-A-95/14008, WO-A-93/18057, U.S. Pat. Nos. 5,658, 935, 5,686,421, 5,389,614, 5,397,796, 5,424,293 and 5,554, 594, which are herein incorporated by reference, describe substituted 5-membered ring heterocycles which have an amino, amidino or guanidino function at the N-terminal end of the molecule and which exhibit platelet aggregation-inhibiting actions. EP-A-796 855 describes further heterocycles which are inhibitors of bone resorption. EP-A-842 943, EP-A-842 945 and EP-A-842 944 describe that compounds from this series and further compounds surprisingly also inhibit leukocyte adhesion and are VLA-4 antagonists.

EP-A-903 353, EP-A-905 139 and EP-A-918 059 and WO-A-99/60015 (German patent application 19821483.9)

describe further compounds which inhibit leukocyte adhesion and are VLA-4 antagonists. The properties of these compounds, however, are still not satisfactory in various respects and there is a need for compounds having a further improved property profile. EP-A-91 8 059 describes, inter alia, imidazolidine derivatives which contain a spiro-linked ring system on the imidazolidine ring. Not specifically disclosed, however, are the spiroimidazolidine derivatives of the present invention, which are distinguished by their advantageous property profile.

SUMMARY OF THE INVENTION

The present invention relates to a compound, and physiologically acceptable salts thereof, in all its stereoisomeric forms and mixtures thereof in all ratios, of the formula I:

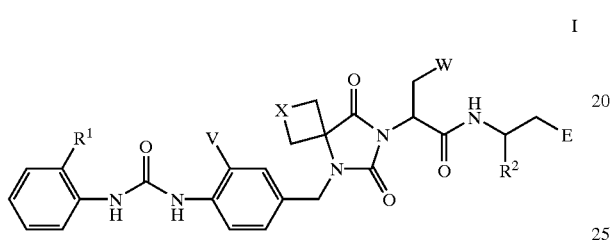

where $R^1$ is hydrogen or methyl; where $R^2$ is phenyl or $(C_1-C_4)$-alkyl; where X is —CH$_2$—CH$_2$— or —CH$_2$—CH$_2$—CH$_2$—, where one of the CH$_2$ groups in these two residues can be replaced by a carbonyl group C=O; where W is isopropyl or cyclopropyl; where V is hydrogen or methoxy; where E is —CO—$R^3$, —CO—H, —CH$_2$—O—$R^4$, —CH$_2$—O—CO—$R^4$, —CH$_2$—O—CO—O—$R^5$ or 5-tetrazolyl; where $R^3$ is hydroxy, $(C_1-C_{10})$-alkoxy, phenyl-$(C_1-C_8)$-alkoxy-, phenyloxy-, $(C_1-C_8)$-alkylcarbonyloxy-$(C_1-C_6)$-alkoxy-, phenylcarbonyloxy-$(C_1-C_6)$-alkoxy-, phenyl-$(C_1-C_6)$-alkylcarbonyloxy-$(C_1-C_6)$-alkoxy-, $(C_1-C_8)$-alkoxycarbonyloxy-$(C_1-C_6)$-alkoxy-, phenyloxycarbonyloxy-$(C_1-C_6)$-alkoxy-, phenyl-$(C_1-C_6)$-alkoxycarbonyloxy-$(C_1-C_6)$-alkoxy-, amino, mono-$((C_1-C_{10})$-alkyl)-amino-, di-$((C_1-C_{10})$-alkyl)-amino- or $R^4R^4N$—CO—$(C_1-C_6)$-alkoxy- in which the residues $R^4$ are independent of one another and can be identical or different; where $R^4$ is hydrogen, $(C_1-C_{10})$-alkyl, phenyl or phenyl-$(C_1-C_8)$-alkyl-; where $R^5$ has one of the meanings of $R^4$ with the proviso that $R^4$ is not hydrogen; where phenyl is an unsubstituted phenyl residue or a phenyl residue which is substituted by one or more identical or different substituents from the group consisting of $(C_1-C_4)$-alkyl, $(C_1-C_4)$-alkoxy, methylenedioxy, ethylenedioxy, halogen, trifluoromethyl and trifluoromethoxy.

In one embodiment, the invention relates to a compound of the formula where W is isopropyl and V is hydrogen. In another embodiment, the invention relates to a compound of the formula I where $R^2$ is unsubstituted phenyl, phenyl substituted by a methylenedioxy residue or an ethylenedioxy residue, or phenyl substituted by one or two $(C_1-C_4)$-alkoxy groups, or $(C_1-C_4)$-alkyl. In yet another embodiment, the invention relates to a compound of the formula I where E is —CO—$R^3$ or —CH$_2$—OH and $R^3$ is hydroxy, a $(C_1-C_6)$-alkoxy or an amino group.

In yet another embodiment, the invention relates to a compound of the formula I where $R^1$ is hydrogen or methyl, where $R^2$ is unsubstituted phenyl, phenyl substituted by a methylenedioxy residue or an ethylenedioxy residue, phenyl substituted by one or two methoxy groups, or $(C_1-C_4)$-alkyl; where X is —CH$_2$—CH$_2$— or —CH$_2$—CH$_2$—CH$_2$—, where one of the CH$_2$ groups in these two residues can be replaced by a carbonyl group C=O; where W is isopropyl or cyclopropyl; where V is hydrogen or methoxy; and where E is —CO—OH, —CO—O—$(C_1-C_4)$-alkyl, —CO—NH$_2$ or —CH$_2$—OH.

The invention also relates to a process for the preparation of a compound of the formula I which includes performing a condensation of a compound of the formula II with a compound of the formula III

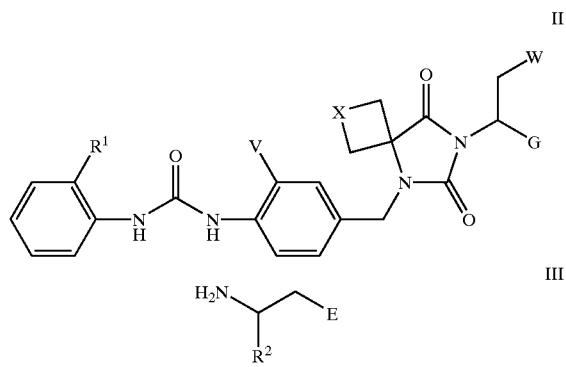

where, in the formulae II and III, the groups E, V, W, X, $R^1$ and $R^2$ are defined as set forth above with reference to formula I or alternatively functional groups are present in protected form or in the form of a precursor, and where G is hydroxycarbonyl, $(C_1-C_6)$-alkoxycarbonyl or an activated carboxylic acid derivative.

In another embodiment, the invention relates to prodrugs of a compound of the formula I for use as pharmaceuticals. In yet another embodiment, the invention relates to a pharmaceutical preparation, which includes one or more compounds of the formula I together with a pharmaceutically acceptable carrier. In a preferred embodiment, the pharmaceutical preparation may be used as an antiinflammatory, for the therapy or prophylaxis of, for example, arthritis, rheumatoid arthritis, polyarthritis, inflammatory bowel disease, systemic lupus erythematosus, multiple sclerosis, inflammatory disorders of the central nervous system, asthma, allergies, cardiovascular disorders, arteriosclerosis, restenoses, diabetes, damage to organ transplants, immune disorders, autoimmune disorders, tumor growth or tumor metastasis, or malaria. In yet another embodiment, the invention relates to a pharmaceutical preparation, which includes one or more compounds of the formula I together with a pharmaceutically acceptable carrier which may be used as an inhibitor of the adhesion and/or migration of leukocytes or for the inhibition of the VLA-4 receptor.

The above and other advantages and features of the invention will be more clearly understood from the following detailed description

DETAILED DESCRIPTION OF THE INVENTION

In the following detailed description, reference is made to specific embodiments by which the invention may be practiced. These embodiments are described in sufficient detail to enable those skilled in the art to practice the invention, and it is to be understood that other embodiments may be utilized, and that changes may be made without departing from the spirit and scope of the present invention.

The present invention relates to compounds of the formula I

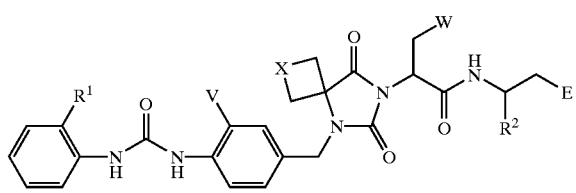

in which
- $R^1$ is hydrogen or methyl;
- $R^2$ is phenyl or $(C_1-C_4)$-alkyl;
- X is —CH$_2$—CH$_2$— or —CH$_2$—CH$_2$—CH$_2$—, where one of the CH$_2$ groups in these two residues can be replaced by a carbonyl group C=O;
- W is isopropyl or cyclopropyl;
- V is hydrogen or methoxy;
- E is —CO—$R^3$, —CO—H, —CH$_2$—O—$R^4$, —CH$_2$—O—CO—$R^4$, —CH$_2$—O—CO—O—$R^5$ or 5-tetrazolyl;
- $R^3$ is hydroxy, $(C_1-C_{10})$-alkoxy, phenyl-$(C_1-C_8)$-alkoxy-, phenyloxy-, $(C_1-C_8)$-alkylcarbonyloxy-$(C_1-C_6)$-alkoxy-, phenylcarbonyloxy-$(C_1-C_6)$-alkoxy-, phenyl-$(C_1-C_6)$-alkylcarbonyloxy-$(C_1-C_6)$-alkoxy-, $(C_1-C_8)$-alkoxycarbonyloxy-$(C_1-C_6)$-alkoxy-, phenyloxycarbonyloxy-$(C_1-C_6)$-alkoxy-, phenyl-$(C_1-C_6)$-alkoxycarbonyloxy-$(C_1-C_6)$-alkoxy-, amino, mono-$((C_1-C_{10})$-alkyl)-amino-, di-$((C_1-C_{10})$-alkyl)-amino- or $R^4R^4N$—CO—$(C_1-C_6)$-alkoxy- in which the residues $R^4$ are independent of one another and can be identical or different;
- $R^4$ is hydrogen, $(C_1-C_{10})$-alkyl, phenyl or phenyl-$(C_1-C_8)$-alkyl-;
- $R^5$ has one of the meanings of $R^4$ with the exception of hydrogen;
- phenyl is an unsubstituted phenyl residue or a phenyl residue which is substituted by one or more identical or different substituents from the group consisting of $(C_1-C_4)$-alkyl, $(C_1-C_4)$-alkoxy, methylenedioxy, ethylenedioxy, halogen, trifluoromethyl and trifluoromethoxy;
- in all their stereoisomeric forms and mixtures thereof in all ratios, and their physiologically acceptable salts.

If a residue occurs more than once in a compound of the formula I for example if $R^2$ is phenyl and a further phenyl residue is contained in the group E, the residues are in all cases independent of one another and can be identical or different.

Alkyl residues can be straight-chain or branched. This also applies if they carry substituents or occur as substituents of other residues, for example in alkoxy residues, alkoxycarbonyl residues or arylalkyl residues. Examples of suitable alkyl residues are methyl, ethyl, n-propyl, n-butyl, n-pentyl, n-hexyl, n-heptyl, n-octyl, n-nonyl, n-decyl, isopropyl, isobutyl, isopentyl, isohexyl, 3-methylpentyl, neopentyl, neohexyl, 2,3,5-trimethylhexyl, sec-butyl, tert-butyl, tert-pentyl. Preferred alkyl residues are methyl, ethyl, n-propyl, isopropyl, n-butyl, isobutyl, sec-butyl, tert-butyl, n-pentyl, isopentyl, n-hexyl and isohexyl. Substituted alkyl residues can be substituted in any desired positions.

If the divalent residue X in the formula I is the divalent 1,2-ethylene residue —CH$_2$—CH$_2$—, that is if X together with the two CH$_2$ groups to which X is bonded forms a tetramethylene residue, the compounds of the formula I contain a spiro-linked cyclopentane ring, and thus compounds of the formula Ia are present which can be designated as 4,4-tetramethyleneimidazolidine derivatives.

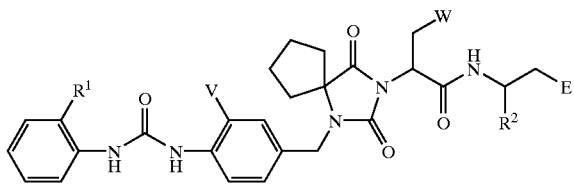

If, in the compounds of the formula Ia, one of the CH$_2$ groups in the cyclopentane ring is replaced by a C=O group, that is if X in the formula I is the group —CH$_2$—CO— or —CO—CH$_2$—, compounds of the formula Ib are present.

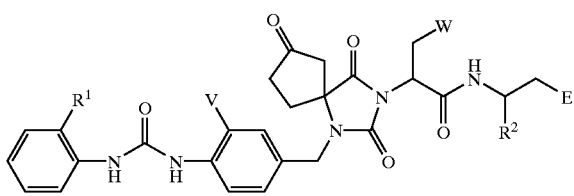

In the compounds of the formula Ib, X together with the two CH$_2$ groups in the formula I to which X is bonded forms a 2-oxotetramethylene residue —CH$_2$—CO—CH$_2$—CH$_2$—. The compounds of the formula Ib can be designated as 4,4-(2-oxotetramethylene)imidazolidine derivatives.

If the divalent residue X in the formula I is the divalent 1,3-propylene residue —CH$_2$—CH$_2$—CH$_2$—, that is if X together with the two CH$_2$ groups to which X is bonded forms a pentamethylene residue, the compounds of the formula I contain a spiro-linked cyclohexane ring, and thus compounds of the formula Ic are present which can be designated as 4,4-pentamethyleneimidazolidine derivatives.

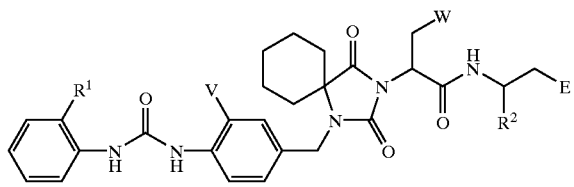

If, in the compounds of the formula Id, one of the CH$_2$ groups in the cyclohexane ring is replaced by a C=O group, that is if X is one of the groups —CO—CH$_2$—CH$_2$—, —CH$_2$—CO—CH$_2$— or —CH$_2$—CH$_2$—CO—, compounds of the formulae Id or Ie are present.

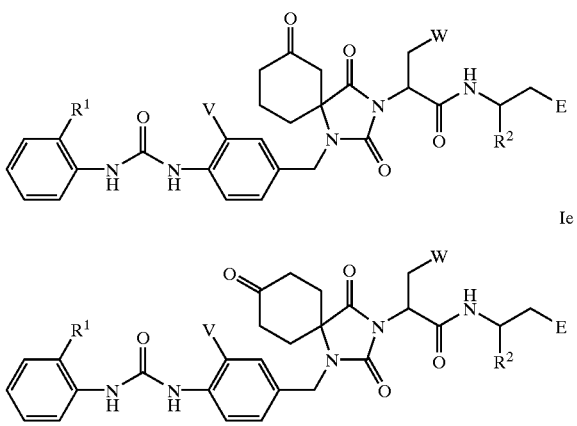

In the compounds of the formulae Id and Ie, X together with the two CH$_2$ groups in the formula I to which X is bonded forms a 2-oxopentamethylene residue —CH$_2$—CO—CH$_2$—CH$_2$—CH$_2$— or a 3-oxopentamethylene residue —CH$_2$—CH$_2$—CO—CH$_2$—CH$_2$—. The compounds of the formulae Id and Ie can be designated as 4,4-(2-oxopentamethylene)imidazolidine derivatives and 4,4-(3-oxopentamethylene)-imidazolidine derivatives. If, in the residue —CH$_2$—CH$_2$—CH$_2$— representing X, a CH$_2$ group is replaced by a carbonyl group, the middle CH$_2$ group is preferably replaced, that is preferably compounds of the formula Ie are present in this case.

Phenyl residues are unsubstituted or are monosubstituted or polysubstituted, for example monosubstituted, disubstituted, trisubstituted, tetrasubstituted or pentasubstituted, by identical or different residues. If a phenyl residue is substituted, it preferably carries one or two identical or different substituents. The same applies, for example, to substituted phenyl residues in groups such as phenylalkyl, phenylcarbonyl, etc. Phenylalkyl residues are, for example, benzyl, 1-phenylethyl or 2-phenylethyl, preferably benzyl, all of which can also be substituted.

In monosubstituted phenyl residues, the substituent can be located in the 2-position, the 3-position or the 4-position. In disubstituted phenyl residues, the substituents can be located in the 2,3-position, 2,4-position, 2,5-position, 2,6-position, 3,4-position or 3,5-position. In trisubstituted phenyl residues, the substituents can be located in the 2,3,4-position, 2,3,5-position, 2,4,5-position, 2,4,6-position, 2,3,6-position or 3,4,5-position. If a phenyl residue carries substituents from the group consisting of methylenedioxy (—O—CH$_2$—O—) and ethylenedioxy (—O—CH$_2$—CH$_2$—O—), it preferably carries only one substituent from this group (optionally in addition to other substituents).

Examples of substituted phenyl residues which, for example, can be R$^2$, are 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 2,4,6-trimethylphenyl, 3,4,5-trimethylphenyl, 2-(n-butyl)phenyl, 3-(n-butyl)phenyl, 4-(n-butyl)phenyl, 2-isobutylphenyl, 3-isobutylphenyl, 4-isobutylphenyl, 3-tert-butylphenyl, 4-tert-butylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,4,5-trimethoxyphenyl, 2,4,6-trimethoxyphenyl, 3,4,5-trimethoxyphenyl, 2-(n-butoxy)phenyl, 3-(n-butoxy)phenyl, 4-(n-butoxy)phenyl, 2-isobutoxyphenyl, 3-isobutoxyphenyl, 4-isobutoxyphenyl, 2-tert-butoxyphenyl, 3-tert-butoxyphenyl, 4-tert-butoxyphenyl, 2,3-methylenedioxyphenyl, 3,4-methylenedioxyphenyl, 2,3-ethylenedioxyphenyl, 3,4-ethylenedioxyphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,4,5-trifluorophenyl, 2,4,6-trifluorophenyl, 3,4,5-trifluorophenyl, 2,3,5,6-tetrafluorophenyl, 2,3,4,5,6-pentafluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2-bromophenyl, 3-bromophenyl, 4-bromophenyl, 3-iodophenyl, 4-iodophenyl, 2-trifluoromethylphenyl, 3-trifluoromethylphenyl, 4-trifluoromethylphenyl, 3,4-bis(trifluoromethyl)phenyl, 3,5-bis(trifluoromethyl)phenyl, 2-trifluoromethoxyphenyl, 3-trifluoromethoxyphenyl, 4-trifluoromethoxyphenyl, etc. In substituted phenyl residues, however, different substituents can also be contained in any desired combination, such as, for example, in the residues 3-methoxy-4-methylphenyl, 4-fluoro-3-methoxyphenyl, 3-fluoro-4-methoxyphenyl, 3,5-difluoro-4-methoxyphenyl, 3-fluoro-4,5-methylenedioxyphenyl, 3-fluoro-4,5-ethylenedioxyphenyl, 2-chloro-3-methylphenyl, 3-chloro-4-methylphenyl, 3-chloro-4-fluorophenyl, etc.

Halogen may be fluorine, chlorine, bromine or iodine, preferably fluorine or chlorine.

Physiologically acceptable salts of the compounds of the formula I are preferably nontoxic or pharmaceutically utilizable salts. Salts of this type of compounds of the formula I which contain acidic groups, for example a carboxylic acid group representing the group E, are, for example, alkali metal salts or alkaline earth metal salts such as, for example, sodium salts, potassium salts, magnesium salts and calcium salts, or ammonium salts such as, for example, salts with physiologically acceptable quaternary ammonium ions and acid addition salts with ammonia and physiologically acceptable organic amines, such as, for example, methylamine, ethylamine, triethylamine, 2-hydroxyethylamine, tris(2-hydroxyethyl)amine, α,α,α-tris(hydroxymethyl)methylamine (tromethamine) or amino acids, preferably basic amino acids. Salts of an acidic compound of the formula I and an organic amine can contain the two components in the ratio 1:1 (or about 1:1) or in another ratio, for example in a ratio of about 1:0.5 to about 1:4 (1 molecule of the formula I to 0.5 to 4 molecules of the amine), preferably in a ratio of about 1:0.5 to about 1:2 (1 molecule of the formula I to 0.5 to 2 molecules of the amine).

Compounds of the formula I which contain basic groups, for example an amino group in the alcohol component of a carboxylic acid ester group, form salts with inorganic acids such as, for example, hydrochloric acid, sulfuric acid or phosphoric acid, and with organic carboxylic acids or sulfonic acids such as, for example, acetic acid, citric acid, benzoic acid, maleic acid, fumaric acid, tartaric acid, methanesulfonic acid or p-toluenesulfonic acid. Compounds which contain both acidic groups and basic groups can also be present in the form of inner salts or betaines or zwitterions, which are likewise included by the present invention.

Salts can be obtained from the compounds of the formula I according to customary processes known to the person skilled in the art, for example by combination with an organic or inorganic acid or base in a solvent or diluent, or also from other salts by anion exchange or cation exchange.

The compounds of the formula I can be present in stereoisomeric forms. On all asymmetric centers in the compounds of the formula I, independently of one another the S configuration or the R configuration can be present or a R/S mixture can be present. Thus the asymmetric carbon atom to which the residue $R^2$ is bonded can have the R configuration or S configuration or the compound of the formula I can be present, with respect to this carbon atom, as an R/S mixture. Likewise, the asymmetric carbon atom to which the group —$CH_2$—W, which is an isobutyl group (=2-methylpropyl group) or a cyclopropylmethyl group, and the imidazolidine ring are bonded can have the R configuration or S configuration or the compound of the formula I can be present with respect to this carbon atom as an R/S mixture. All other asymmetric carbon atoms can also have the R configuration or the S configuration or the compound of the formula I can be present with respect to each of these carbon atoms as an R/S mixture.

The invention includes all possible stereoisomers of the compounds of the formula I, for example pure or largely pure enantiomers and pure or largely pure diastereomers and mixtures of two or more stereoisomeric forms, for example mixtures of enantiomers and/or diastereomers, in all ratios. Enantiomers are thus a subject of the invention in enantiomerically pure form, both as levorotatory and as dextrorotatory antipodes, in the form of racemates and in the form of mixtures of the two enantiomers in all ratios. Likewise, diastereomers in diastereomerically pure form and in the form of mixtures in all ratios are a subject of the invention. Examples of individual stereoisomers which are a subject of the invention are the compounds of the formulae If, Ig, Ih and Ii.

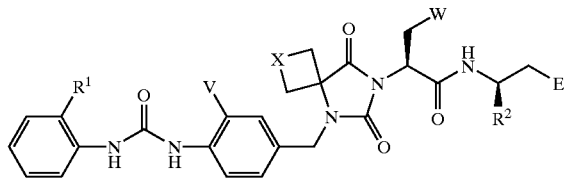

If

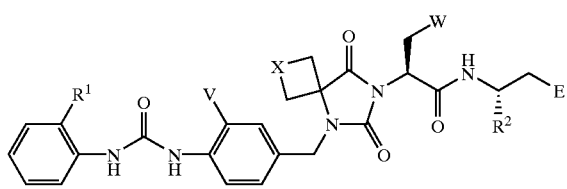

Ig

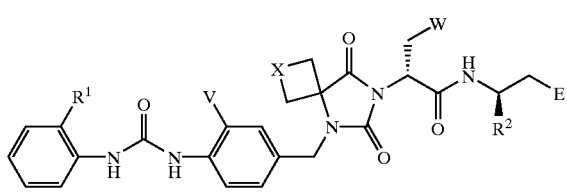

Ih

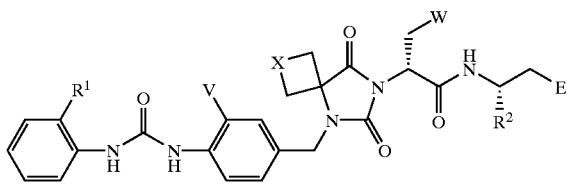

Ii

The individual stereoisomers can be prepared, if desired, by use of stereochemically uniform starting substances in the synthesis, by stereoselective synthesis or by separation of a mixture according to customary methods, for example by chromatography or crystallization, in the case of enantiomers for example by chromatography on chiral phases. Optionally, before separation of stereoisomers a derivatization can be carried out. The separation of a stereoisomer mixture can take place at the stage of the compounds of the formula I or at the stage of a starting substance or of an intermediate in the course of the synthesis.

The compounds of the formula I according to the invention can contain mobile hydrogen atoms, that is be present in various tautomeric forms. All tautomers of the compounds of the formula I are also a subject of the present invention. The present invention also includes solvates and addition compounds or adducts of compounds of the formula I, for example adducts with water, that is hydrates, or adducts with alcohols or amines. The invention furthermore includes derivatives of compounds of the formula I, for example esters, amides, prodrugs and other physiologically acceptable derivatives, and also active metabolites of compounds of the formula I. The invention also relates to prodrugs of the compounds of the formula I, which can be converted into compounds of the formula I under physiological conditions. Suitable prodrugs of the compounds of the formula I, that is chemically modified derivatives of the compounds of the formula I having desirably improved properties, are known to the person skilled in the art. Details of prodrugs are found, for example, in Fleisher et al., Advanced Drug Delivery Reviews 19 (1996) 115; Design of Prodrugs, H. Bundgaard, Ed., Elsevier, 1985; H. Bundgaard, Drugs of the Future 16 (1991) 443. Possible prodrugs of the compounds of the formula I are especially ester prodrugs, amide prodrugs, aldehyde prodrugs and alcohol prodrugs of carboxylic acid groups. Examples of ester prodrugs and amide prodrugs which may be mentioned are ($C_1$–$C_4$)-alkyl esters such as methyl esters, ethyl esters, isopropyl esters, isobutyl esters, substituted alkyl esters such as hydroxyalkyl esters, acyloxyalkyl esters, aminoalkyl esters, acylaminoalkyl esters, dialkylaminoalkyl esters, unsubstituted amides or N—($C_1$–$C_4$)-alkylamides such as methylamides or ethylamides.

With respect to the structural elements V and W, the present invention includes four embodiments each of which expressly is a subject of the present invention. In one of these embodiments, the group W in the formula I is isopropyl, that is the residue —$CH(CH_3)_2$, and at the same time V is hydrogen. This embodiment thus includes compounds of the formula Ik Ik

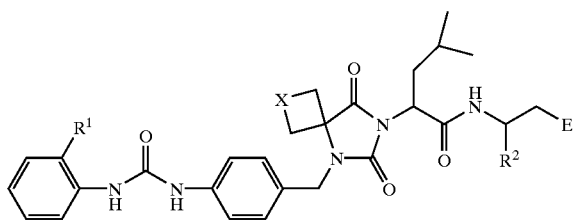

in which
- $R^1$ is hydrogen or methyl;
- $R^2$ is phenyl or $(C_1-C_4)$-alkyl;
- X is —$CH_2$—$CH_2$— or —$CH_2$—$CH_2$—$CH_2$—, where one of the $CH_2$ groups in these two residues can be replaced by a carbonyl group C=O;
- E is —CO—$R^3$, —CO—H, —$CH_2$—O—$R^4$, —$CH_2$—O—CO—$R^4$, —$CH_2$—O—CO—O—$R^5$ or 5-tetrazolyl;
- $R^3$ is hydroxy, $(C_1-C_{10})$-alkoxy, phenyl-$(C_1-C_8)$-alkoxy-, phenyloxy-, $(C_1-C_8)$-alkylcarbonyloxy-$(C_1-C_6)$-alkoxy-, phenylcarbonyloxy-$(C_1-C_6)$-alkoxy-, phenyl-$(C_1-C_6)$-alkylcarbonyloxy-$(C_1-C_6)$-alkoxy-, $(C_1-C_8)$-alkoxycarbonyloxy-$(C_1-C_6)$-alkoxy-, phenyloxycarbonyloxy-$(C_1-C_6)$-alkoxy-, phenyl-$(C_1-C_6)$-alkoxycarbonyloxy-$(C_1-C_6)$-alkoxy-, amino, mono-$((C_1-C_{10})$-alkyl)-amino-, di-$((C_1-C_{10})$-alkyl)-amino- or $R^4R^4N$—CO—$(C_1-C_6)$-alkoxy- in which the residues $R^4$ are independent of one another and can be identical or different;
- $R^4$ is hydrogen, $(C_1-C_{10})$-alkyl, phenyl or phenyl-$(C_1-C_8)$-alkyl-;
- $R^5$ has one of the meanings of $R^4$ with the exception of hydrogen;
- phenyl is an unsubstituted phenyl residue or a phenyl residue which is substituted by one or more identical or different substituents from the group consisting of $(C_1-C_4)$-alkyl, $(C_1-C_4)$-alkoxy, methylenedioxy, ethylenedioxy, halogen, trifluoromethyl and trifluoromethoxy;

in all their stereoisomeric forms and mixtures thereof in all ratios,
and their physiologically acceptable salts.

A second of these four embodiments relates to compounds of the formula I in which W is cyclopropyl, that is the residue

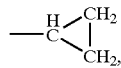

and at the same time V is hydrogen. A third embodiment relates to compounds of the formula I in which W is isopropyl and at the same time V is methoxy, that is the residue —$OCH_3$. A fourth embodiment relates to compounds of the formula I in which W is cyclopropyl and at the same time V is methoxy. A subgroup of the compounds according to the invention includes the compounds of the second, third and fourth embodiment described above, that is compounds of the formula I in which V is hydrogen or methoxy and W is isopropyl or cyclopropyl, but in which not at the same time V is hydrogen and W is isopropyl. Also the compounds of the second, third and fourth embodiment of the invention are a subject of the invention in all their stereoisomeric forms and mixtures thereof in all ratios and in the form of their physiologically acceptable salts.

The individual structural elements in the formula I preferably have the following meanings, which they can have independently of one another.

E is preferably —CO—$R^3$, —CO—H, —$CH_2$—O—$R^4$, —$CH_2$—O—CO—$R^4$ or —$CH_2$—O—CO—$OR^5$, particularly preferably —CO—$R^3$, —CO—H, —$CH_2$—O—$R^4$ or —$CH_2$—O—CO—$R^4$, very particularly preferably —CO—$R^3$, —$CH_2$—O—$R^4$ or —$CH_2$—O—CO—$R^4$, moreover preferably —CO—$R^3$ or —$CH_2$—O—$R^4$, especially preferably —CO—$R^3$. A residue —$CH_2$—O—$R^4$ representing the group E is preferably the hydroxymethyl residue —$CH_2$—OH. Especially preferred meanings of E are —CO—O—$(C_1-C_4)$-alkyl, —CO—OH, —CO—$NH_2$ and —$CH_2$—OH, preferably —CO—OH, —CO—$NH_2$ and —$CH_2$—OH, most preferably —CO—OH.

X is preferably —$CH_2$—$CH_2$— or —$CH_2$—$CH_2$—$CH_2$—, more preferably —$CH_2$—$CH_2$—$CH_2$—, where none of the $CH_2$ groups is replaced by a carbonyl group.

$R^2$ is preferably unsubstituted phenyl, phenyl which is substituted by a methylenedioxy residue or an ethylenedioxy residue, phenyl which is substituted by one or two $(C_1-C_4)$-alkoxy groups, preferably by methoxy groups, or $(C_1-C_4)$-alkyl, where the $(C_1-C_4)$-alkyl group preferably is methyl, ethyl or isobutyl, more preferably methyl or ethyl, particularly preferably methyl. Particularly preferably, $R^2$ is unsubstituted phenyl, phenyl which is substituted by a methylenedioxy residue or an ethylenedioxy residue, phenyl which is substituted by one or two methoxy groups, or methyl. Very particularly preferably, $R^2$ is unsubstituted phenyl, 3,4-methylene-dioxyphenyl, 3,4-ethylenedioxyphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl or methyl.

$R^3$ is preferably hydroxy, $(C_1-C_6)$-alkoxy or amino (—$NH_2$), particularly preferably hydroxy, $(C_1-C_4)$-alkoxy or amino, very particularly preferably hydroxy or amino, especially preferably hydroxy.

$R^4$ is preferably hydrogen or $(C_1-C_6)$-alkyl, particularly preferably hydrogen or $(C_1-C_4)$-alkyl. $R^5$ is preferably $(C_1-C_6)$-alkyl, particularly preferably $(C_1-C_4)$-alkyl.

Preferred compounds of the formula I are those which have a uniform configuration on one or on more chiral centers, for example on the carbon atom which carries the residue $R^2$, and/or on the carbon atom which carries the group —$CH_2$—W. That is, compounds are preferred which are present in uniform or in essentially uniform configuration on one or more chiral centers, either in the R configuration or in the S configuration, but not as an R/S mixture. As explained, the individual chiral centers in these compounds of the formula I, however, can independently of one another have the R configuration or the S configuration and can have identical or different configurations. Particularly preferred compounds of the formula I are those in which the carbon atom which carries the group —$CH_2$—W is present in the S configuration, that is in the configuration with respect to this stereocenter which is shown in the formulae If and Ig. Particularly preferred compounds of the formula I are also those in which the carbon atom which carries the group $R^2$ is present in the configuration shown in the formulae If and Ih. If $R^2$ is phenyl or substituted phenyl, in these particularly preferred compounds the carbon atom which carries the group $R^2$ has the S configuration, if $R^2$ is, for example, methyl, ethyl or isobutyl, it has the R configuration. Very particularly preferred compounds of the formula I are those in which the two abovementioned stereocenters are present in the configurations shown in the formula If.

Preferred compounds of the formula I are those compounds in which one or more of the residues have preferred meanings or have a specific meaning from the listed meanings, all combinations of preferred meanings of residues being a subject of the present invention.

Particularly preferred compounds include compounds of the formula I, in which $R^1$ is hydrogen or methyl;

$R^2$ is unsubstituted phenyl, phenyl which is substituted by a methylenedioxy residue or an ethylenedioxy residue, phenyl which is substituted by one or two $(C_1-C_4)$-alkoxy groups, or $(C_1-C_4)$-alkyl;

X is —$CH_2$—$CH_2$— or —$CH_2$—$CH_2$—$CH_2$—, where one of the $CH_2$ groups in these two residues can be replaced by a carbonyl group C=O;

W is isopropyl or cyclopropyl;

V is hydrogen or methoxy;

E is —CO—$R^3$, —CO—H, —$CH_2$—O—$R^4$, —$CH_2$—O—CO—$R^4$ or —$CH_2$—O—CO—O—$R^5$;

$R^3$ is hydroxy, $(C_1-C_{10})$-alkoxy, phenyl-$(C_1-C_8)$-alkoxy-, phenyloxy-, $(C_1-C_8)$-alkylcarbonyloxy-$(C_1-C_6)$-alkoxy-, phenylcarbonyloxy-$(C_1-C_6)$-alkoxy-, phenyl-$(C_1-C_6)$-alkylcarbonyloxy-$(C_1-C_6)$-alkoxy-, $(C_1-C_8)$-alkoxycarbonyloxy-$(C_1-C_6)$-alkoxy-, phenyloxycarbonyloxy-$(C_1-C_6)$-alkoxy-, phenyl-$(C_1-C_6)$-alkoxycarbonyloxy-$(C_1-C_6)$-alkoxy-, amino, mono-$((C_1-C_{10})$-alkyl)-amino-, di-$((C_1-C_{10})$-alkyl)-amino- or $R^4R^4N$—CO—$(C_1-C_6)$-alkoxy- in which the residues $R^4$ are independent of one another and can be identical or different;

$R^4$ is hydrogen, $(C_1-C_{10})$-alkyl, phenyl or phenyl-$(C_1-C_8)$-alkyl-;

$R^5$ has one of the meanings of $R^4$ with the exception of hydrogen;

phenyl which is contained in the group E is an unsubstituted phenyl residue or a phenyl residue which is substituted by one or more identical or different substituents from the group consisting of $(C_1-C_4)$-alkyl, $(C_1-C_4)$-alkoxy, methylenedioxy, ethylenedioxy, halogen, trifluoromethyl and trifluoromethoxy;

in all their stereoisomeric forms and mixtures thereof in all ratios, and their physiologically acceptable salts.

The most preferred compounds include compounds of the formula I in which $R^1$ is hydrogen or methyl;

$R^2$ is unsubstituted phenyl, phenyl which is substituted by a methylenedioxy residue or an ethylenedioxy residue, phenyl which is substituted by one or two methoxy groups, or $(C_1-C_4)$-alkyl;

X is —$CH_2$—$CH_2$— or —$CH_2$—$CH_2$—$CH_2$—, where one of the $CH_2$ groups in these two residues can be replaced by a carbonyl group C=O;

W is isopropyl or cyclopropyl;

V is hydrogen or methoxy;

E is —CO—OH, —CO—O—$(C_1-C_4)$-alkyl, —CO—$NH_2$ or —$CH_2$—OH;

in all their stereoisomeric forms and mixtures thereof in all ratios, and their physiologically acceptable salts.

A subgroup of these compounds is formed by the compounds of the formula I in which $R^1$ is hydrogen or methyl;

$R^2$ is phenyl which is substituted by a methylenedioxy residue or an ethylenedioxy residue, or phenyl which is substituted by one or two methoxy groups;

X is —$CH_2$—$CH_2$— or —$CH_2$—$CH_2$—$CH_2$—, where one of the $CH_2$ groups in these two residues can be replaced by a carbonyl group C=O;

W is isopropyl or cyclopropyl;

V is hydrogen or methoxy;

E is —CO—OH, —CO—O—$(C_1-C_4)$-alkyl, —CO—$NH_2$ or —$CH_2$—OH;

in all their stereoisomeric forms and mixtures thereof in all ratios, and their physiologically acceptable salts.

A further subgroup of these compounds is formed by compounds of the formula I in which $R^1$ is hydrogen or methyl;

$R^2$ is unsubstituted phenyl;

X is —$CH_2$—$CH_2$— or —$CH_2$—$CH_2$—$CH_2$—, where one of the $CH_2$ groups in these two residues can be replaced by a carbonyl group C=O;

W is isopropyl or cyclopropyl;

V is hydrogen or methoxy;

E is —CO—OH, —CO—O—$(C_1-C_4)$-alkyl, —CO—$NH_2$ or —$CH_2$—OH;

in all their stereoisomeric forms and mixtures thereof in all ratios, and their physiologically acceptable salts.

A further subgroup of these compounds is formed by compounds of the formula I in which $R^1$ is hydrogen or methyl;

$R^2$ is $(C_1-C_4)$-alkyl, preferably methyl;

X is —$CH_2$—$CH_2$— or —$CH_2$—$CH_2$—$CH_2$—, where one of the $CH_2$ groups in these two residues can be replaced by a carbonyl group C=O;

W is isopropyl or cyclopropyl;

V is hydrogen or methoxy;

E is —CO—OH, —CO—O—$(C_1-C_4)$-alkyl, —CO—$NH_2$ or —$CH_2$—OH;

in all their stereoisomeric forms and mixtures thereof in all ratios, and their physiologically acceptable salts.

For the abovementioned embodiment of the invention in which the group V in the compounds of the formula I is hydrogen and the group W is isopropyl, that is for the compounds of the formula Ik, examples of specific compounds are indicated below each of which expressly is a subject of the present invention. The following abbreviations are used in the names of the compounds.

IBU=2-methylpropyl=isobutyl=—CH—$CH_2$—CH($CH_3$)$_2$

4PM-3-PUB-DI=4,4-pentamethylene-3-(4-(3-phenylureido)benzyl)-2,5-dioxoimidazolidin-1-yl 4PM-3-MPUB-DI=4,4-pentamethylene-3-(4-(3-(2-methylphenyl)ureido)benzyl)-2,5-dioxoimidazolidin-1-yl 4TM-3-PUB-DI=4,4-tetramethylene-3-(4-(3-phenylureido)benzyl)-2,5-dioxoimidazolidin-1-yl 4TM-3-MPUB-DI=4,4-tetramethylene-3-(4-(3-(2-methylphenyl)ureido)benzyl)-2,5-dioxoimidazolidin-1-yl 4OPM-3-PUB-DI=4,4-(3-oxopentamethylene)-3-(4-(3-phenylureido)benzyl)-2,5-dioxoimidazolidin-1-yl 4OPM-3-MPUB-DI=4,4-(3-oxopentamethylene)-3-(4-(3-(2-methylphenyl)ureido)-benzyl)-2,5-dioxoimidazolidin-1-yl 4OTM-3-PUB-DI=4,4-(2-oxotetramethylene)-3-(4-(3-phenylureido)benzyl)-2,5-dioxoimidazolidin-1-yl 4OTM-3-MPUB-DI=4,4-(2-oxotetramethylene)-3-(4-(3-(2-methylphenyl)ureido)-benzyl)-2,5-dioxoimidazolidin-1-yl A name such as, for example, 3-(2-(4OPM-3-MPUB-DI)-2-(IBU)-acetylamino)-3-(3,4-dimethoxyphenyl) propionamide is thus to be understood as meaning the compound 3-(2-(4,4-(3-oxopentamethylene)-3-(4-(3-(2-methylphenyl)ureido)benzyl)-2,5-dioxoimidazolidin-1-yl)-2-(2-methylpropyl)acetylamino)-3-(3,4-dimethoxyphenyl) propionamide of the formula Im.

Im

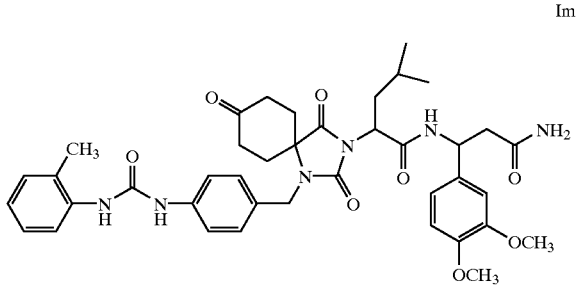

The present invention relates, for example, to the following compounds:

3-(2-(4PM-3-PUB-DI)-2-(IBU)-acetylamino)-3-methylpropionic acid
3-(2-(4PM-3-MPUB-DI)-2-(IBU)-acetylamino)-3-methylpropionic acid
3-(2-(4TM-3-PUB-DI)-2-(IBU)-acetylamino)-3-methylpropionic acid
3-(2-(4TM-3-MPUB-DI)-2-(IBU)-acetylamino)-3-methylpropionic acid
3-(2-(4OPM-3-PUB-DI)-2-(IBU)-acetylamino)-3-methylpropionic acid
3-(2-(4OPM-3-MPUB-DI)-2-(IBU)-acetylamino)-3-methylpropionic acid
3-(2-(4OTM-3-PUB-DI)-2-(IBU)-acetylamino)-3-methylpropionic acid
3-(2-(4OTM-3-MPUB-DI)-2-(IBU)-acetylamino)-3-methylpropionic acid 3-(2-(4PM-3-PUB-DI)-2-(IBU)-acetylamino)-3-methylpropionamide
3-(2-(4PM-3-MPUB-DI)-2-(IBU)-acetylamino)-3-methylpropionamide
3-(2-(4TM-3-PUB-DI)-2-(IBU)-acetylamino)-3-methylpropionamide
3-(2-(4TM-3-MPUB-DI)-2-(IBU)-acetylamino)-3-methylpropionamide
3-(2-(4OPM-3-PUB-DI)-2-(IBU)-acetylamino)-3-methylpropionamide
3-(2-(4OPM-3-MPUB-DI)-2-(IBU)-acetylamino)-3-methylpropionamide
3-(2-(4OTM-3-PUB-DI)-2-(IBU)-acetylamino)-3-methylpropionamide
3-(2-(4OTM-3-MPUB-DI)-2-(IBU)-acetylamino)-3-methylpropionamide 3-(2-(4PM-3-PUB-DI)-2-(IBU)-acetylamino)-3-methylpropanol
3-(2-(4PM-3-MPUB-DI)-2-(IBU)-acetylamino)-3-methylpropanol
3-(2-(4TM-3-PUB-DI)-2-(IBU)-acetylamino)-3-methylpropanol
3-(2-(4TM-3-MPUB-DI)-2-(IBU)-acetylamino)-3-methylpropanol
3-(2-(4OPM-3-PUB-DI)-2-(IBU)-acetylamino)-3-methylpropanol
3-(2-(4OPM-3-MPUB-DI)-2-(IBU)-acetylamino)-3-methylpropanol
3-(2-(4OTM-3-PUB-DI)-2-(IBU)-acetylamino)-3-methylpropanol
3-(2-(4OTM-3-MPUB-DI)-2-(IBU)-acetylamino)-3-methylpropanol 3-(2-(4PM-3-PUB-DI)-2-(IBU)-acetylamino)-3-(IBU)-propionic acid
3-(2-(4PM-3-MPUB-DI)-2-(IBU)-acetylamino)-3-(IBU)-propionic acid
3-(2-(4TM-3-PUB-DI)-2-(IBU)-acetylamino)-3-(IBU)-propionic acid
3-(2-(4TM-3-MPUB-DI)-2-(IBU)-acetylamino)-3-(IBU)-propionic acid
3-(2-(4OPM-3-PUB-DI)-2-(IBU)-acetylamino)-3-(IBU)-propionic acid
3-(2-(4OPM-3-MPUB-DI)-2-(IBU)-acetylamino)-3-(IBU)-propionic acid
3-(2-(4OTM-3-PUB-DI)-2-(IBU)-acetylamino)-3-(IBU)-propionic acid
3-(2-(4OTM-3-MPUB-DI)-2-(IBU)-acetylamino)-3-(IBU)-propionic acid 3-(2-(4PM-3-PUB-DI)-2-(IBU)-acetylamino)-3-(IBU)-propionamide
3-(2-(4PM-3-MPUB-DI)-2-(IBU)-acetylamino)-3-(IBU)-propionamide
3-(2-(4TM-3-PUB-DI)-2-(IBU)-acetylamino)-3-(IBU)-propionamide
3-(2-(4TM-3-MPUB-DI)-2-(IBU)-acetylamino)-3-(IBU)-propionamide
3-(2-(4OPM-3-PUB-DI)-2-(IBU)-acetylamino)-3-(IBU)-propionamide
3-(2-(4OPM-3-MPUB-DI)-2-(IBU)-acetylamino)-3-(IBU)-propionamide
3-(2-(4OTM-3-PUB-DI)-2-(IBU)-acetylamino)-3-(IBU)-propionamide
3-(2-(4OTM-3-MPUB-DI)-2-(IBU)-acetylamino)-3-(IBU)-propionamide 3-(2-(4PM-3-PUB-DI)-2-(IBU)-acetylamino)-3-(IBU)-propanol
3-(2-(4PM-3-MPUB-DI)-2-(IBU)-acetylamino)-3-(IBU)-propanol
3-(2-(4TM-3-PUB-DI)-2-(IBU)-acetylamino)-3-(IBU)-propanol
3-(2-(4TM-3-MPUB-DI)-2-(IBU)-acetylamino)-3-(IBU)-propanol
3-(2-(4OPM-3-PUB-DI)-2-(IBU)-acetylamino)-3-(IBU)-propanol
3-(2-(4OPM-3-MPUB-DI)-2-(IBU)-acetylamino)-3-(IBU)-propanol
3-(2-(4OTM-3-PUB-DI)-2-(IBU)-acetylamino)-3-(IBU)-propanol
3-(2-(4OTM-3-MPUB-DI)-2-(IBU)-acetylamino)-3-(IBU)-propanol 3-(2-(4PM-3-PUB-DI)-2-(IBU)-acetylamino)-3-phenylpropionic acid
3-(2-(4PM-3-MPUB-DI)-2-(IBU)-acetylamino)-3-phenylpropionic acid
3-(2-(4TM-3-PUB-DI)-2-(IBU)-acetylamino)-3-phenylpropionic acid 3-(2-(4TM-3-MPUB-DI)-2-(IBU)-acetylamino)-3-phenylpropionic acid
3-(2-(4OPM-3-PUB-DI)-2-(IBU)-acetylamino)-3-phenylpropionic acid
3-(2-(4OPM-3-MPUB-DI)-2-(IBU)-acetylamino)-3-phenylpropionic acid
3-(2-(4OTM-3-PUB-DI)-2-(IBU)-acetylamino)-3-phenylpropionic acid
3-(2-(4OTM-3-MPUB-DI)-2-(IBU)-acetylamino)-3-phenylpropionic acid 3-(2-(4PM-3-PUB-DI)-2-(IBU)-acetylamino)-3-phenylpropionamide
3-(2-(4PM-3-MPUB-DI)-2-(IBU)-acetylamino)-3-phenylpropionamide
3-(2-(4TM-3-PUB-DI)-2-(IBU)-acetylamino)-3-phenylpropionamide
3-(2-(4TM-3-MPUB-DI)-2-(IBU)-acetylamino)-3-phenylpropionamide
3-(2-(4OPM-3-PUB-DI)-2-(IBU)-acetylamino)-3-phenylpropionamide
3-(2-(4OPM-3-MPUB-DI)-2-(IBU)-acetylamino)-3-phenylpropionamide
3-(2-(4OTM-3-PUB-DI)-2-(IBU)-acetylamino)-3-phenylpropionamide
3-(2-(4OTM-3-MPUB-DI)-2-(IBU)-acetylamino)-3-phenylpropionamide 3-(2-(4PM-3-PUB-DI)-2-(IBU)-acetylamino)-3-phenylpropanol
3-(2-(4PM-3-MPUB-DI)-2-(IBU)-acetylamino)-3-phenylpropanol
3-(2-(4TM-3-PUB-DI)-2-(IBU)-acetylamino)-3-phenylpropanol
3-(2-(4TM-3-MPUB-DI)-2-(IBU)-acetylamino)-3-phenylpropanol
3-(2-(4OPM-3-PUB-DI)-2-(IBU)-acetylamino)-3-phenylpropanol
3-(2-(4OPM-3-MPUB-DI)-2-(IBU)-acetylamino)-3-phenylpropanol
3-(2-(4OTM-3-PUB-DI)-2-(IBU)-acetylamino)-3-phenylpropanol
3-(2-(4OTM-3-MPUB-DI)-2-(IBU)-acetylamino)-3-phenylpropanol 3-(2-(4PM-3-PUB-DI)-2-(IBU)-acetylamino)-3-(2-methoxyphenyl)propionic acid
3-(2-(4PM-3-MPUB-DI)-2-(IBU)-acetylamino)-3-(2-methoxyphenyl)propionic acid
3-(2-(4TM-3-PUB-DI)-2-(IBU)-acetylamino)-3-(2-methoxyphenyl)propionic acid
3-(2-(4TM-3-MPUB-DI)-2-(IBU)-acetylamino)-3-(2-methoxyphenyl)propionic acid
3-(2-(4OPM-3-PUB-DI)-2-(IBU)-acetylamino)-3-(2-methoxyphenyl)propionic acid
3-(2-(4OPM-3-MPUB-DI)-2-(IBU)-acetylamino)-3-(2-methoxyphenyl)propionic acid
3-(2-(4OTM-3-PUB-DI)-2-(IBU)-acetylamino)-3-(2-methoxyphenyl)propionic acid
3-(2-(4OTM-3-MPUB-DI)-2-(IBU)-acetylamino)-3-(2-methoxyphenyl)propionic acid 3-(2-(4PM-3-PUB-DI)-2-(IBU)-acetylamino)-3-(2-methoxyphenyl)propionamide
3-(2-(4PM-3-MPUB-DI)-2-(IBU)-acetylamino)-3-(2-methoxyphenyl)propionamide
3-(2-(4TM-3-PUB-DI)-2-(IBU)-acetylamino)-3-(2-methoxyphenyl)propionamide
3-(2-(4TM-3-MPUB-DI)-2-(IBU)-acetylamino)-3-(2-methoxyphenyl)propionamide
3-(2-(4OPM-3-PUB-DI)-2-(IBU)-acetylamino)-3-(2-methoxyphenyl)propionamide
3-(2-(4OPM-3-MPUB-DI)-2-(IBU)-acetylamino)-3-(2-methoxyphenyl)propionamide
3-(2-(4OTM-3-PUB-DI)-2-(IBU)-acetylamino)-3-(2-methoxyphenyl)propionamide
3-(2-(4OTM-3-MPUB-DI)-2-(IBU)-acetylamino)-3-(2-methoxyphenyl)propionamide 3-(2-(4PM-3-PUB-DI)-2-(IBU)-acetylamino)-3-(2-methoxyphenyl)propanol
3-(2-(4PM-3-MPUB-DI)-2-(IBU)-acetylamino)-3-(2-methoxyphenyl)propanol
3-(2-(4TM-3-PUB-DI)-2-(IBU)-acetylamino)-3-(2-methoxyphenyl)propanol
3-(2-(4TM-3-MPUB-DI)-2-(IBU)-acetylamino)-3-(2-methoxyphenyl)propanol
3-(2-(4OPM-3-PUB-DI)-2-(IBU)-acetylamino)-3-(2-methoxyphenyl)propanol
3-(2-(4OPM-3-MPUB-DI)-2-(IBU)-acetylamino)-3-(2-methoxyphenyl)propanol
3-(2-(4OTM-3-PUB-DI)-2-(IBU)-acetylamino)-3-(2-methoxyphenyl)propanol
3-(2-(4OTM-3-MPUB-DI)-2-(IBU)-acetylamino)-3-(2-methoxyphenyl)propanol 3-(2-(4PM-3-PUB-DI)-2-(IBU)-acetylamino)-3-(3-methoxyphenyl)propionic acid
3-(2-(4PM-3-MPUB-DI)-2-(IBU)-acetylamino)-3-(3-methoxyphenyl)propionic acid
3-(2-(4TM-3-PUB-DI)-2-(IBU)-acetylamino)-3-(3-methoxyphenyl)propionic acid
3-(2-(4TM-3-MPUB-DI)-2-(IBU)-acetylamino)-3-(3-methoxyphenyl)propionic acid
3-(2-(4OPM-3-PUB-DI)-2-(IBU)-acetylamino)-3-(3-methoxyphenyl)propionic acid
3-(2-(4OPM-3-MPUB-DI)-2-(IBU)-acetylamino)-3-(3-methoxyphenyl)propionic acid
3-(2-(4OTM-3-PUB-DI)-2-(IBU)-acetylamino)-3-(3-methoxyphenyl)propionic acid
3-(2-(4OTM-3-MPUB-DI)-2-(IBU)-acetylamino)-3-(3-methoxyphenyl)propionic acid 3-(2-(4PM-3-PUB-DI)-2-(IBU)-acetylamino)-3-(3-methoxyphenyl)propionamide
3-(2-(4PM-3-MPUB-DI)-2-(IBU)-acetylamino)-3-(3-methoxyphenyl)propionamide
3-(2-(4TM-3-PUB-DI)-2-(IBU)-acetylamino)-3-(3-methoxyphenyl)propionamide
3-(2-(4TM-3-MPUB-DI)-2-(IBU)-acetylamino)-3-(3-methoxyphenyl)propionamide
3-(2-(4OPM-3-PUB-DI)-2-(IBU)-acetylamino)-3-(3-methoxyphenyl)propionamide
3-(2-(4OPM-3-MPUB-DI)-2-(IBU)-acetylamino)-3-(3-methoxyphenyl)propionamide
3-(2-(4OTM-3-PUB-DI)-2-(IBU)-acetylamino)-3-(3-methoxyphenyl)propionamide
3-(2-(4OTM-3-MPUB-DI)-2-(IBU)-acetylamino)-3-(3-methoxyphenyl)propionamide 3-(2-(4PM-3-PUB-DI)-2-(IBU)-acetylamino)-3-(3-methoxyphenyl)propanol
3-(2-(4PM-3-MPUB-DI)-2-(IBU)-acetylamino)-3-(3-methoxyphenyl)propanol 3-(2-(4TM-3-PUB-DI)-2-(IBU)-acetylamino)-3-(3-methoxyphenyl)propanol
3-(2-(4TM-3-MPUB-DI)-2-(IBU)-acetylamino)-3-(3-methoxyphenyl)propanol
3-(2-(4OPM-3-PUB-DI)-2-(IBU)-acetylamino)-3-(3-methoxyphenyl)propanol
3-(2-(4OPM-3-MPUB-DI)-2-(IBU)-acetylamino)-3-(3-methoxyphenyl)propanol
3-(2-(4OTM-3-PUB-DI)-2-(IBU)-acetylamino)-3-(3-methoxyphenyl)propanol
3-(2-(4OTM-3-MPUB-DI)-2-(IBU)-acetylamino)-3-(3-methoxyphenyl)propanol 3-(2-(4PM-3-PUB-DI)-2-(IBU)-acetylamino)-3-(4-methoxyphenyl)propionic acid
3-(2-(4PM-3-MPUB-DI)-2-(IBU)-acetylamino)-3-(4-methoxyphenyl)propionic acid
3-(2-(4TM-3-PUB-DI)-2-(IBU)-acetylamino)-3-(4-methoxyphenyl)propionic acid
3-(2-(4TM-3-MPUB-DI)-2-(IBU)-acetylamino)-3-(4-methoxyphenyl)propionic acid
3-(2-(4OPM-3-PUB-DI)-2-(IBU)-acetylamino)-3-(4-methoxyphenyl)propionic acid
3-(2-(4OPM-3-MPUB-DI)-2-(IBU)-acetylamino)-3-(4-methoxyphenyl)propionic acid
3-(2-(4OTM-3-PUB-DI)-2-(IBU)-acetylamino)-3-(4-methoxyphenyl)propionic acid
3-(2-(4OTM-3-MPUB-DI)-2-(IBU)-acetylamino)-3-(4-methoxyphenyl)propionic acid 3-(2-(4PM-3-PUB-DI)-2-(IBU)-acetylamino)-3-(4-methoxyphenyl)propionamide
3-(2-(4PM-3-MPUB-DI)-2-(IBU)-acetylamino)-3-(4-methoxyphenyl)propionamide
3-(2-(4TM-3-PUB-DI)-2-(IBU)-acetylamino)-3-(4-methoxyphenyl)propionamide
3-(2-(4TM-3-MPUB-DI)-2-(IBU)-acetylamino)-3-(4-methoxyphenyl)propionamide
3-(2-(4OPM-3-PUB-DI)-2-(IBU)-acetylamino)-3-(4-methoxyphenyl)propionamide
3-(2-(4OPM-3-MPUB-DI)-2-(IBU)-acetylamino)-3-(4-methoxyphenyl)propionamide
3-(2-(4OTM-3-PUB-DI)-2-(IBU)-acetylamino)-3-(4-methoxyphenyl)propionamide
3-(2-(4OTM-3-MPUB-DI)-2-(IBU)-acetylamino)-3-(4-methoxyphenyl)propionamide 3-(2-(4PM-3-PUB-DI)-2-(IBU)-acetylamino)-3-(4-methoxyphenyl)propanol
3-(2-(4PM-3-MPUB-DI)-2-(IBU)-acetylamino)-3-(4-methoxyphenyl)propanol
3-(2-(4TM-3-PUB-DI)-2-(IBU)-acetylamino)-3-(4-methoxyphenyl)propanol
3-(2-(4TM-3-MPUB-DI)-2-(IBU)-acetylamino)-3-(4-methoxyphenyl)propanol
3-(2-(4OPM-3-PUB-DI)-2-(IBU)-acetylamino)-3-(4-methoxyphenyl)propanol
3-(2-(4OPM-3-MPUB-DI)-2-(IBU)-acetylamino)-3-(4-methoxyphenyl)propanol
3-(2-(4OTM-3-PUB-DI)-2-(IBU)-acetylamino)-3-(4-methoxyphenyl)propanol
3-(2-(4OTM-3-MPUB-DI)-2-(IBU)-acetylamino)-3-(4-methoxyphenyl)propanol 3-(2-(4PM-3-PUB-DI)-2-(IBU)-acetylamino)-3-(2,3-dimethoxyphenyl)propionic acid
3-(2-(4PM-3-MPUB-DI)-2-(IBU)-acetylamino)-3-(2,3-dimethoxyphenyl)propionic acid
3-(2-(4TM-3-PUB-DI)-2-(IBU)-acetylamino)-3-(2,3-dimethoxyphenyl)propionic acid
3-(2-(4TM-3-MPUB-DI)-2-(IBU)-acetylamino)-3-(2,3-dimethoxyphenyl)propionic acid
3-(2-(4OPM-3-PUB-DI)-2-(IBU)-acetylamino)-3-(2,3-dimethoxyphenyl)propionic acid
3-(2-(4OPM-3-MPUB-DI)-2-(IBU)-acetylamino)-3-(2,3-dimethoxyphenyl)propionic acid
3-(2-(4OTM-3-PUB-DI)-2-(IBU)-acetylamino)-3-(2,3-dimethoxyphenyl)propionic acid
3-(2-(4OTM-3-MPUB-DI)-2-(IBU)-acetylamino)-3-(2,3-dimethoxyphenyl)propionic acid 3-(2-(4PM-3-PUB-DI)-2-(IBU)-acetylamino)-3-(2,3-dimethoxyphenyl)propionamide
3-(2-(4PM-3-MPUB-DI)-2-(IBU)-acetylamino)-3-(2,3-dimethoxyphenyl)propionamide
3-(2-(4TM-3-PUB-DI)-2-(IBU)-acetylamino)-3-(2,3-dimethoxyphenyl)propionamide
3-(2-(4TM-3-MPUB-DI)-2-(IBU)-acetylamino)-3-(2,3-dimethoxyphenyl)propionamide
3-(2-(4OPM-3-PUB-DI)-2-(IBU)-acetylamino)-3-(2,3-dimethoxyphenyl)propionamide
3-(2-(4OPM-3-MPUB-DI)-2-(IBU)-acetylamino)-3-(2,3-dimethoxyphenyl)propionamide
3-(2-(4OTM-3-PUB-DI)-2-(IBU)-acetylamino)-3-(2,3-dimethoxyphenyl)propionamide
3-(2-(4OTM-3-MPUB-DI)-2-(IBU)-acetylamino)-3-(2,3-dimethoxyphenyl)propionamide 3-(2-(4PM-3-PUB-DI)-2-(IBU)-acetylamino)-3-(2,3-dimethoxyphenyl)propanol
3-(2-(4PM-3-MPUB-DI)-2-(IBU)-acetylamino)-3-(2,3-dimethoxyphenyl)propanol
3-(2-(4TM-3-PUB-DI)-2-(IBU)-acetylamino)-3-(2,3-dimethoxyphenyl)propanol
3-(2-(4TM-3-MPUB-DI)-2-(IBU)-acetylamino)-3-(2,3-dimethoxyphenyl)propanol
3-(2-(4OPM-3-PUB-DI)-2-(IBU)-acetylamino)-3-(2,3-dimethoxyphenyl)propanol
3-(2-(4OPM-3-MPUB-DI)-2-(IBU)-acetylamino)-3-(2,3-dimethoxyphenyl)propanol
3-(2-(4OTM-3-PUB-DI)-2-(IBU)-acetylamino)-3-(2,3-dimethoxyphenyl)propanol
3-(2-(4OTM-3-MPUB-DI)-2-(IBU)-acetylamino)-3-(2,3-dimethoxyphenyl)propanol 3-(2-(4PM-3-MPUB-DI)-2-(IBU)-acetylamino)-3-(2,4-dimethoxyphenyl)propionic acid
3-(2-(4PM-3-MPUB-DI)-2-(IBU)-acetylamino)-3-(2,4-dimethoxyphenyl)propionic acid
3-(2-(4TM-3-PUB-DI)-2-(IBU)-acetylamino)-3-(2,4-dimethoxyphenyl)propionic acid
3-(2-(4TM-3-MPUB-DI)-2-(IBU)-acetylamino)-3-(2,4-dimethoxyphenyl)propionic acid
3-(2-(4OPM-3-PUB-DI)-2-(IBU)-acetylamino)-3-(2,4-dimethoxyphenyl)propionic acid
3-(2-(4OPM-3-PUB-DI)-2-(IBU)-acetylamino)-3-(2,4-dimethoxyphenyl)propionic acid
3-(2-(4OTM-3-PUB-DI)-2-(IBU)-acetylamino)-3-(2,4-dimethoxyphenyl)propionic acid
3-(2-(4OTM-3-MPUB-DI)-2-(IBU)-acetylamino)-3-(2,4-dimethoxyphenyl)propionic acid 3-(2-(4PM-3-PUB-DI)-2-(IBU)-acetylamino)-3-(2,4-dimethoxyphenyl)propionamide
3-(2-(4PM-3-MPUB-DI)-2-(IBU)-acetylamino)-3-(2,4-dimethoxyphenyl)propionamide 3-(2-(4TM-3-PUB-DI)-2-(IBU)-acetylamino)-3-(2,4-dimethoxyphenyl)propionamide
3-(2-(4TM-3-MPUB-DI)-2-(IBU)-acetylamino)-3-(2,4-dimethoxyphenyl)propionamide
3-(2-(4OPM-3-PUB-DI)-2-(IBU)-acetylamino)-3-(2,4-dimethoxyphenyl)propionamide
3-(2-(4OPM-3-MPUB-DI)-2-(IBU)-acetylamino)-3-(2,4-dimethoxyphenyl)propionamide
3-(2-(4OTM-3-PUB-DI)-2-(IBU)-acetylamino)-3-(2,4-dimethoxyphenyl)propionamide
3-(2-(4OTM-3-MPUB-DI)-2-(IBU)-acetylamino)-3-(2,4-dimethoxyphenyl)propionamide 3-(2-(4PM-3-PUB-DI)-2-(IBU)-acetylamino)-3-(2,4-dimethoxyphenyl)propanol
3-(2-(4PM-3-MPUB-DI)-2-(IBU)-acetylamino)-3-(2,4-dimethoxyphenyl)propanol
3-(2-(4TM-3-PUB-DI)-2-(IBU)-acetylamino)-3-(2,4-dimethoxyphenyl)propanol
3-(2-(4TM-3-MPUB-DI)-2-(IBU)-acetylamino)-3-(2,4-dimethoxyphenyl)propanol
3-(2-(4OPM-3-PUB-DI)-2-(IBU)-acetylamino)-3-(2,4-dimethoxyphenyl)propanol
3-(2-(4OPM-3-MPUB-DI)-2-(IBU)-acetylamino)-3-(2,4-dimethoxyphenyl)propanol
3-(2-(4OTM-3-PUB-DI)-2-(IBU)-acetylamino)-3-(2,4-dimethoxyphenyl)propanol
3-(2-(4OTM-3-MPUB-DI)-2-(IBU)-acetylamino)-3-(2,4-dimethoxyphenyl)propanol 3-(2-(4PM-3-PUB-DI)-2-(IBU)-acetylamino)-3-(2,5-dimethoxyphenyl)propionic acid
3-(2-(4PM-3-MPUB-DI)-2-(IBU)-acetylamino)-3-(2,5-dimethoxyphenyl)propionic acid
3-(2-(4TM-3-PUB-DI)-2-(IBU)-acetylamino)-3-(2,5-dimethoxyphenyl)propionic acid
3-(2-(4TM-3-MPUB-DI)-2-(IBU)-acetylamino)-3-(2,5-dimethoxyphenyl)propionic acid
3-(2-(4OPM-3-PUB-DI)-2-(IBU)-acetylamino)-3-(2,5-dimethoxyphenyl)propionic acid
3-(2-(4OPM-3-MPUB-DI)-2-(IBU)-acetylamino)-3-(2,5-dimethoxyphenyl)propionic acid
3-(2-(4OTM-3-PUB-DI)-2-(IBU)-acetylamino)-3-(2,5-dimethoxyphenyl)propionic acid
3-(2-(4OTM-3-MPUB-DI)-2-(IBU)-acetylamino)-3-(2,5-dimethoxyphenyl)propionic acid 3-(2-(4PM-3-PUB-DI)-2-(IBU)-acetylamino)-3-(2,5-dimethoxyphenyl)propionamide
3-(2-(4PM-3-MPUB-DI)-2-(IBU)-acetylamino)-3-(2,5-dimethoxyphenyl)propionamide
3-(2-(4TM-3-PUB-DI)-2-(IBU)-acetylamino)-3-(2,5-dimethoxyphenyl)propionamide
3-(2-(4TM-3-MPUB-DI)-2-(IBU)-acetylamino)-3-(2,5-dimethoxyphenyl)propionamide
3-(2-(4OPM-3-PUB-DI)-2-(IBU)-acetylamino)-3-(2,5-dimethoxyphenyl)propionamide
3-(2-(4OPM-3-MPUB-DI)-2-(IBU)-acetylamino)-3-(2,5-dimethoxyphenyl)propionamide
3-(2-(4OTM-3-PUB-DI)-2-(IBU)-acetylamino)-3-(2,5-dimethoxyphenyl)propionamide
3-(2-(4OTM-3-MPUB-DI)-2-(IBU)-acetylamino)-3-(2,5-dimethoxyphenyl)propionamide 3-(2-(4PM-3-PUB-DI)-2-(IBU)-acetylamino)-3-(2,5-dimethoxyphenyl)propanol
3-(2-(4PM-3-MPUB-DI)-2-(IBU)-acetylamino)-3-(2,5-dimethoxyphenyl)propanol
3-(2-(4TM-3-PUB-DI)-2-(IBU)-acetylamino)-3-(2,5-dimethoxyphenyl)propanol
3-(2-(4TM-3-MPUB-DI)-2-(IBU)-acetylamino)-3-(2,5-dimethoxyphenyl)propanol
3-(2-(4OPM-3-PUB-DI)-2-(IBU)-acetylamino)-3-(2,5-dimethoxyphenyl)propanol
3-(2-(4OPM-3-MPUB-DI)-2-(IBU)-acetylamino)-3-(2,5-dimethoxyphenyl)propanol
3-(2-(4OTM-3-PUB-DI)-2-(IBU)-acetylamino)-3-(2,5-dimethoxyphenyl)propanol
3-(2-(4OTM-3-MPUB-DI)-2-(IBU)-acetylamino)-3-(2,5-dimethoxyphenyl)propanol 3-(2-(4PM-3-PUB-DI)-2-(IBU)-acetylamino)-3-(2,6-dimethoxyphenyl)propionic acid
3-(2-(4PM-3-MPUB-DI)-2-(IBU)-acetylamino)-3-(2,6-dimethoxyphenyl)propionic acid
3-(2-(4TM-3-PUB-DI)-2-(IBU)-acetylamino)-3-(2,6-dimethoxyphenyl)propionic acid
3-(2-(4TM-3-MPUB-DI)-2-(IBU)-acetylamino)-3-(2,6-dimethoxyphenyl)propionic acid
3-(2-(4OPM-3-PUB-DI)-2-(IBU)-acetylamino)-3-(2,6-dimethoxyphenyl)propionic acid
3-(2-(4OPM-3-MPUB-DI)-2-(IBU)-acetylamino)-3-(2,6-dimethoxyphenyl)propionic acid
3-(2-(4OTM-3-PUB-DI)-2-(IBU)-acetylamino)-3-(2,6-dimethoxyphenyl)propionic acid
3-(2-(4OTM-3-MPUB-DI)-2-(IBU)-acetylamino)-3-(2,6-dimethoxyphenyl)propionic acid 3-(2-(4PM-3-PUB-DI)-2-(IBU)-acetylamino)-3-(2,6-dimethoxyphenyl)propionamide
3-(2-(4PM-3-MPUB-DI)-2-(IBU)-acetylamino)-3-(2,6-dimethoxyphenyl)propionamide
3-(2-(4TM-3-PUB-DI)-2-(IBU)-acetylamino)-3-(2,6-dimethoxyphenyl)propionamide
3-(2-(4TM-3-MPUB-DI)-2-(IBU)-acetylamino)-3-(2,6-dimethoxyphenyl)propionamide
3-(2-(4OPM-3-PUB-DI)-2-(IBU)-acetylamino)-3-(2,6-dimethoxyphenyl)propionamide
3-(2-(4OPM-3-MPUB-DI)-2-(IBU)-acetylamino)-3-(2,6-dimethoxyphenyl)propionamide
3-(2-(4OTM-3-PUB-DI)-2-(IBU)-acetylamino)-3-(2,6-dimethoxyphenyl)propionamide
3-(2-(4OTM-3-MPUB-DI)-2-(IBU)-acetylamino)-3-(2,6-dimethoxyphenyl)propionamide 3-(2-(4PM-3-PUB-DI)-2-(IBU)-acetylamino)-3-(2,6-dimethoxyphenyl)propanol
3-(2-(4PM-3-MPUB-DI)-2-(IBU)-acetylamino)-3-(2,6-dimethoxyphenyl)propanol
3-(2-(4TM-3-PUB-DI)-2-(IBU)-acetylamino)-3-(2,6-dimethoxyphenyl)propanol
3-(2-(4TM-3-MPUB-DI)-2-(IBU)-acetylamino)-3-(2,6-dimethoxyphenyl)propanol
3-(2-(4OPM-3-PUB-DI)-2-(IBU)-acetylamino)-3-(2,6-dimethoxyphenyl)propanol
3-(2-(4OPM-3-MPUB-DI)-2-(IBU)-acetylamino)-3-(2,6-dimethoxyphenyl)propanol
3-(2-(4OTM-3-PUB-DI)-2-(IBU)-acetylamino)-3-(2,6-dimethoxyphenyl)propanol
3-(2-(4OTM-3-MPUB-DI)-2-(IBU)-acetylamino)-3-(2,6-dimethoxyphenyl)propanol 3-(2-(4PM-3-PUB-DI)-2-(IBU)-acetylamino)-3-(3,4-dimethoxyphenyl)propionic acid 3-(2-(4PM-3-MPUB-DI)-2-(IBU)-acetylamino)-3-(3,4-dimethoxyphenyl)propionic acid
3-(2-(4TM-3-PUB-DI)-2-(IBU)-acetylamino)-3-(3,4-dimethoxyphenyl)propionic acid
3-(2-(4TM-3-MPUB-DI)-2-(IBU)-acetylamino)-3-(3,4-dimethoxyphenyl)propionic acid
3-(2-(4OPM-3-PUB-DI)-2-(IBU)-acetylamino)-3-(3,4-dimethoxyphenyl)propionic acid
3-(2-(4OPM-3-MPUB-DI)-2-(IBU)-acetylamino)-3-(3,4-dimethoxyphenyl)propionic acid
3-(2-(4OTM-3-PUB-DI)-2-(IBU)-acetylamino)-3-(3,4-dimethoxyphenyl)propionic acid
3-(2-(4OTM-3-MPUB-DI)-2-(IBU)-acetylamino)-3-(3,4-dimethoxyphenyl)propionic acid 3-(2-(4PM-3-PUB-DI)-2-(IBU)-acetylamino)-3-(3,4-dimethoxyphenyl)propionamide
3-(2-(4PM-3-MPUB-DI)-2-(IBU)-acetylamino)-3-(3,4-dimethoxyphenyl)propionamide
3-(2-(4TM-3-PUB-DI)-2-(IBU)-acetylamino)-3-(3,4-dimethoxyphenyl)propionamide
3-(2-(4TM-3-MPUB-DI)-2-(IBU)-acetylamino)-3-(3,4-dimethoxyphenyl)propionamide
3-(2-(4OPM-3-PUB-DI)-2-(IBU)-acetylamino)-3-(3,4-dimethoxyphenyl)propionamide
3-(2-(4OPM-3-MPUB-DI)-2-(IBU)-acetylamino)-3-(3,4-dimethoxyphenyl)propionamide
3-(2-(4OTM-3-PUB-DI)-2-(IBU)-acetylamino)-3-(3,4-dimethoxyphenyl)propionamide
3-(2-(4OTM-3-MPUB-DI)-2-(IBU)-acetylamino)-3-(3,4-dimethoxyphenyl)propionamide 3-(2-(4PM-3-PUB-DI)-2-(IBU)-acetylamino)-3-(3,4-dimethoxyphenyl)propanol
3-(2-(4PM-3-MPUB-DI)-2-(IBU)-acetylamino)-3-(3,4-dimethoxyphenyl)propanol
3-(2-(4TM-3-PUB-DI)-2-(IBU)-acetylamino)-3-(3,4-dimethoxyphenyl)propanol
3-(2-(4TM-3-MPUB-DI)-2-(IBU)-acetylamino)-3-(3,4-dimethoxyphenyl)propanol
3-(2-(4PM-3-PUB-DI)-2-(IBU)-acetylamino)-3-(3,4-dimethoxyphenyl)propanol
3-(2-(4OPM-3-MPUB-DI)-2-(IBU)-acetylamino)-3-(3,4-dimethoxyphenyl)propanol
3-(2-(4OTM-3-PUB-DI)-2-(IBU)-acetylamino)-3-(3,4-dimethoxyphenyl)propanol
3-(2-(4OTM-3-MPUB-DI)-2-(IBU)-acetylamino)-3-(3,4-dimethoxyphenyl)propanol 3-(2-(4PM-3-PUB-DI)-2-(IBU)-acetylamino)-3-(3,5-dimethoxyphenyl)propionic acid
3-(2-(4PM-3-MPUB-DI)-2-(IBU)-acetylamino)-3-(3,5-dimethoxyphenyl)propionic acid
3-(2-(4TM-3-PUB-DI)-2-(IBU)-acetylamino)-3-(3,5-dimethoxyphenyl)propionic acid
3-(2-(4TM-3-MPUB-DI)-2-(IBU)-acetylamino)-3-(3,5-dimethoxyphenyl)propionic acid
3-(2-(4OPM-3-PUB-DI)-2-(IBU)-acetylamino)-3-(3,5-dimethoxyphenyl)propionic acid
3-(2-(4OPM-3-MPUB-DI)-2-(IBU)-acetylamino)-3-(3,5-dimethoxyphenyl)propionic acid
3-(2-(4OTM-3-PUB-DI)-2-(IBU)-acetylamino)-3-(3,5-dimethoxyphenyl)propionic acid
3-(2-(4OTM-3-MPUB-DI)-2-(IBU)-acetylamino)-3-(3,5-dimethoxyphenyl)propionic acid 3-(2-(4PM-3-PUB-DI)-2-(IBU)-acetylamino)-3-(3,5-dimethoxyphenyl)propionamide
3-(2-(4PM-3-MPUB-DI)-2-(IBU)-acetylamino)-3-(3,5-dimethoxyphenyl)propionamide
3-(2-(4TM-3-PUB-DI)-2-(IBU)-acetylamino)-3-(3,5-dimethoxyphenyl)propionamide
3-(2-(4TM-3-MPUB-DI)-2-(IBU)-acetylamino)-3-(3,5-dimethoxyphenyl)propionamide
3-(2-(4OPM-3-PUB-DI)-2-(IBU)-acetylamino)-3-(3,5-dimethoxyphenyl)propionamide
3-(2-(4OPM-3-MPUB-DI)-2-(IBU)-acetylamino)-3-(3,5-dimethoxyphenyl)propionamide
3-(2-(4OTM-3-PUB-DI)-2-(IBU)-acetylamino)-3-(3,5-dimethoxyphenyl)propionamide
3-(2-(4OPM-3-MPUB-DI)-2-(IBU)-acetylamino)-3-(3,5-dimethoxyphenyl)propionamide 3-(2-(4PM-3-PUB-DI)-2-(IBU)-acetylamino)-3-(3,5-dimethoxyphenyl)propanol
3-(2-(4PM-3-MPUB-DI)-2-(IBU)-acetylamino)-3-(3,5-dimethoxyphenyl)propanol
3-(2-(4TM-3-PUB-DI)-2-(IBU)-acetylamino)-3-(3,5-dimethoxyphenyl)propanol
3-(2-(4TM-3-MPUB-DI)-2-(IBU)-acetylamino)-3-(3,5-dimethoxyphenyl)propanol
3-(2-(4OPM-3-PUB-DI)-2-(IBU)-acetylamino)-3-(3,5-dimethoxyphenyl)propanol
3-(2-(4OPM-3-MPUB-DI)-2-(IBU)-acetylamino)-3-(3,5-dimethoxyphenyl)propanol
3-(2-(4OTM-3-PUB-DI)-2-(IBU)-acetylamino)-3-(3,5-dimethoxyphenyl)propanol
3-(2-(4OTM-3-MPUB-DI)-2-(IBU)-acetylamino)-3-(3,5-dimethoxyphenyl)propanol 3-(2-(4PM-3-PUB-DI)-2-(IBU)-acetylamino)-3-(3,4-methylenedioxyphenyl)propionic acid
3-(2-(4PM-3-MPUB-DI)-2-(IBU)-acetylamino)-3-(3,4-methylenedioxyphenyl)propionic acid
3-(2-(4TM-3-PUB-DI)-2-(IBU)-acetylamino)-3-(3,4-methylenedioxyphenyl)propionic acid
3-(2-(4TM-3-MPUB-DI)-2-(IBU)-acetylamino)-3-(3,4-methylenedioxyphenyl)propionic acid
3-(2-(4OPM-3-PUB-DI)-2-(IBU)-acetylamino)-3-(3,4-methylenedioxyphenyl)propionic acid
3-(2-(4OPM-3-MPUB-DI)-2-(IBU)-acetylamino)-3-(3,4-methylenedioxyphenyl)propionic acid
3-(2-(4OTM-3-PUB-DI)-2-(IBU)-acetylamino)-3-(3,4-methylenedioxyphenyl)propionic acid
3-(2-(4OTM-3-MPUB-DI)-2-(IBU)-acetylamino)-3-(3,4-methylenedioxyphenyl)propionic acid 3-(2-(4PM-3-PUB-DI)-2-(IBU)-acetylamino)-3-(3,4-methylenedioxyphenyl)propionamide
3-(2-(4PM-3-MPUB-DI)-2-(IBU)-acetylamino)-3-(3,4-methylenedioxyphenyl)propionamide
3-(2-(4TM-3-PUB-DI)-2-(IBU)-acetylamino)-3-(3,4-methylenedioxyphenyl)propionamide
3-(2-(4TM-3-MPUB-DI)-2-(IBU)-acetylamino)-3-(3,4-methylenedioxyphenyl)propionamide
3-(2-(4OPM-3-PUB-DI)-2-(IBU)-acetylamino)-3-(3,4-methylenedioxyphenyl)propionamide
3-(2-(4OPM-3-MPUB-DI)-2-(IBU)-acetylamino)-3-(3,4-methylenedioxyphenyl)propionamide
3-(2-(4OTM-3-PUB-DI)-2-(IBU)-acetylamino)-3-(3,4-methylenedioxyphenyl)propionamide
3-(2-(4OTM-3-MPUB-DI)-2-(IBU)-acetylamino)-3-(3,4-methylenedioxyphenyl)propionamide 3-(2-(4PM-3-PUB-DI)-2-(IBU)-acetylamino)-3-(3,4-methylenedioxyphenyl)propanol
3-(2-(4PM-3-MPUB-DI)-2-(IBU)-acetylamino)-3-(3,4-methylenedioxyphenyl)propanol 3-(2-(4TM-3-PUB-DI)-2-(IBU)-acetylamino)-3-(3,4-methylenedioxyphenyl)propanol
3-(2-(4TM-3-MPUB-DI)-2-(IBU)-acetylamino)-3-(3,4-methylenedioxyphenyl)propanol
3-(2-(4OPM-3-PUB-DI)-2-(IBU)-acetylamino)-3-(3,4-methylenedioxyphenyl)propanol
3-(2-(4OPM-3-MPUB-DI)-2-(IBU)-acetylamino)-3-(3,4-methylenedioxyphenyl)propanol
3-(2-(4OTM-3-PUB-DI)-2-(IBU)-acetylamino)-3-(3,4-methylenedioxyphenyl)propanol
3-(2-(4OTM-3-MPUB-DI)-2-(IBU)-acetylamino)-3-(3,4-methylenedioxyphenyl)propanol 3-(2-(4PM-3-PUB-DI)-2-(IBU)-acetylamino)-3-(3,4-ethylenedioxyphenyl)propionic acid
3-(2-(4PM-3-MPUB-DI)-2-(IBU)-acetylamino)-3-(3,4-ethylenedioxyphenyl)propionic acid
3-(2-(4TM-3-PUB-DI)-2-(IBU)-acetylamino)-3-(3,4-ethylenedioxyphenyl)propionic acid
3-(2-(4TM-3-MPUB-DI)-2-(IBU)-acetylamino)-3-(3,4-ethylenedioxyphenyl)propionic acid
3-(2-(4OPM-3-PUB-DI)-2-(IBU)-acetylamino)-3-(3,4-ethylenedioxyphenyl)propionic acid
3-(2-(4OPM-3-MPUB-DI)-2-(IBU)-acetylamino)-3-(3,4-ethylenedioxyphenyl)propionic acid
3-(2-(4OTM-3-PUB-DI)-2-(IBU)-acetylamino)-3-(3,4-ethylenedioxyphenyl)propionic acid
3-(2-(4OTM-3-MPUB-DI)-2-(IBU)-acetylamino)-3-(3,4-ethylenedioxyphenyl)propionic acid 3-(2-(4PM-3-PUB-DI)-2-(IBU)-acetylamino)-3-(3,4-ethylenedioxyphenyl)propionamide
3-(2-(4PM-3-MPUB-DI)-2-(IBU)-acetylamino)-3-(3,4-ethylenedioxyphenyl)propionamide
3-(2-(4TM-3-PUB-DI)-2-(IBU)-acetylamino)-3-(3,4-ethylenedioxyphenyl)propionamide
3-(2-(4TM-3-MPUB-DI)-2-(IBU)-acetylamino)-3-(3,4-ethylenedioxyphenyl)propionamide
3-(2-(4OPM-3-PUB-DI)-2-(IBU)-acetylamino)-3-(3,4-ethylenedioxyphenyl)propionamide
3-(2-(4OPM-3-MPUB-DI)-2-(IBU)-acetylamino)-3-(3,4-ethylenedioxyphenyl)propionamide
3-(2-(4OTM-3-PUB-DI)-2-(IBU)-acetylamino)-3-(3,4-ethylenedioxyphenyl)propionamide
3-(2-(4OTM-3-MPUB-DI)-2-(IBU)-acetylamino)-3-(3,4-ethylenedioxyphenyl)propionamide 3-(2-(4PM-3-PUB-DI)-2-(IBU)-acetylamino)-3-(3,4-ethylenedioxyphenyl)propanol
3 (2-(4PM-3-MPUB-DI)-2-(IBU)-acetylamino)-3-(3,4-ethylenedioxyphenyl)propanol
3-(2-(4TM-3-PUB-DI)-2-(IBU)-acetylamino)-3-(3,4-ethylenedioxyphenyl)propanol
3-(2-(4TM-3-MPUB-DI)-2-(IBU)-acetylamino)-3-(3,4-ethylenedioxyphenyl)propanol
3-(2-(4OPM-3-PUB-DI)-2-(IBU)-acetylamino)-3-(3,4-ethylenedioxyphenyl)propanol
3-(2-(4OPM-3-MPUB-DI)-2-(IBU)-acetylamino)-3-(3,4-ethylenedioxyphenyl)propanol
3-(2-(4OTM-3-PUB-DI)-2-(IBU)-acetylamino)-3-(3,4-ethylenedioxyphenyl)propanol
3-(2-(4OTM-3-MPUB-DI)-2-(IBU)-acetylamino)-3-(3,4-ethylenedioxyphenyl)propanol All abovementioned compounds are a subject of the present invention in all their stereoisomeric forms and in the form of mixtures thereof in all ratios. The compound 3-(2-(4,4-(3-oxopentamethylene)-3-(4-(3-(2-methylphenyl)ureido)benzyl)-2,5-dioxoimidazolidin-1-yl)-2-(2-methylpropyl)acetylamino)-3-(3,4-dimethoxyphenyl)propionamide mentioned above as an example is thus a subject of the invention, inter alia, in the form of (RS)-3-((RS)-2-(4,4-(3-oxopentamethylene)-3-(4-(3-(2-methylphenyl)ureido)benzyl)-2,5-dioxoimidazolidin-1-yl)-2-(2-methylpropyl)acetyl-amino)-3-(3,4-dimethoxyphenyl)propionamide, in the form of (S)-3-((S)-2-(4,4-(3-oxopentamethylene)-3-(4-(3-(2-methylphenyl)ureido)benzyl)-2,5-dioxoimidazolidin-1-yl)-2-(2-methylpropyl)acetylamino)-3-(3,4-dimethoxyphenyl)propionamide, in the form of (S)-3-((R)-2-(4,4-(3-oxopentamethylene)-3-(4-(3-(2-methylphenyl)ureido)benzyl)-2,5-dioxoimidazolidin-1-yl)-2-(2-methylpropyl)acetylamino)-3-(3,4-dimethoxyphenyl)propionamide, in the form of (R)-3-((S)-2-(4,4-(3-oxopentamethylene)-3-(4-(3-(2-methylphenyl)ureido)benzyl)-2,5-dioxoimidazolidin-1-yl)-2-(2-methylpropyl)acetylamino)-3-(3,4-dimethoxyphenyl)propionamide, in the form of (R)-3-((R)-2-(4,4-(3-oxopentamethylene)-3-(4-(3-(2-methylphenyl)ureido)benzyl)-2,5-dioxoimidazolidin-1-yl)-2-(2-methylpropyl)acetylamino)-3-(3,4-dimethoxyphenyl)propionamide, in the form of (S)-3-((RS)-2-(4,4-(3-oxopentamethylene)-3-(4-(3-(2-methylphenyl)ureido)benzyl)-2,5-dioxoimidazolidin-1-yl)-2-(2-methylpropyl)acetylamino)-3-(3,4-dimethoxyphenyl)propionamide, in the form of (R)-3-((RS)-2-(4,4-(3-oxopentamethylene)-3-(4-(3-(2-methylphenyl)ureido)benzyl)-2,5-dioxoimidazolidin-1-yl )-2-(2-methylpropyl)acetylamino)-3-(3,4-dimethoxyphenyl)propionamide, in the form of (RS)-3-((R)-2-(4,4-(3-oxopentamethylene)-3-(4-(3-(2-methylphenyl)ureido)benzyl)-2,5-dioxoimidazolidin-1-yl)-2-(2-methylpropyl)acetylamino)-3-(3,4-dimethoxyphenyl)propionamide and in the form of (RS)-3-((S)-2-(4,4-(3-oxopentamethylene)-3-(4-(3-(2-methylphenyl)ureido)-benzyl)-2,5-dioxoimidazolidin-1-yl)-2-(2-methylpropyl)acetylamino)-3-(3,4-dimethoxyphenyl)propionamide, and this applies expressly to all compounds mentioned. In another way of looking at the situation, with respect to the individual stereoisomers all compounds mentioned are a subject of the invention in the stereochemical arrangement which is shown in formula If, as well as in the arrangement which is shown in formula Ig, as well as in the arrangement which is shown in formula Ih, as well as in the arrangement which is shown in formula Ii, preferably in the stereochemical arrangement which is shown in formula If. Also all above-listed compounds are a subject of the invention in the form of their physiologically acceptable salts and in the form of their prodrugs and other physiologically acceptable derivatives, for example their esters.

The present invention furthermore expressly relates to all compounds analogous to the listed individual compounds which instead of the isobutyl-substituted acetylamino group contain a cyclopropylmethyl-substituted acetylamino group, and to all compounds analogous to the listed individual compounds which instead of the 4-(3-arylureido)benzyl group contain a 4-(3-arylureido)-3-methoxybenzyl group, and to all compounds analogous to the listed individual compounds which at the same time instead of the isobutyl-substituted acetylamino group contain a cyclopropylmethyl-substituted acetylamino group and instead of the 4-(3-arylureido)benzyl group contain a 4-(3-arylureido)-3-methoxybenzyl group, where also all these compounds are a subject of the present invention in all their stereoisomeric forms and in the form of mixtures thereof in all ratios and in the form of their physiologically acceptable salts and in the form of their prodrugs.

The compounds of the formula I can be prepared, for example, by condensation of a compound of the formula II

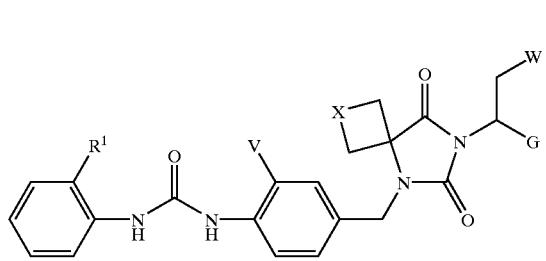

with a compound of the formula III

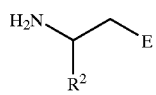

where, in the formulae II and III the groups X, W, V, E, $R^1$ and $R^2$ are defined as indicated above or also functional groups in these groups can be present in protected form or in the form of precursors, and where G is hydroxycarbonyl, $(C_1-C_6)$-alkoxycarbonyl or an activated carboxylic acid derivative such as an acid chloride or an active ester.

In the condensation of the compounds of the formulae II and III, usually it is necessary that a carboxylic acid group which is present but which is not involved in the condensation reaction is protected by a reversible protective group, for example as a suitable $(C_1-C_6)$-alkyl ester such as the tert-butyl ester or as a benzyl ester. If compounds of the formula I are to be prepared in which the group E is, for example, hydroxycarbonyl or a group which is to be prepared from a hydroxycarbonyl group, in the compounds of the formula III, for example, the group E can initially be a hydroxycarbonyl group which is present in protected form and then, after the condensation of the compounds of the formulae II and III, in one or more further steps, the hydroxycarbonyl group can be liberated or the desired final group E can be synthesized.

Precursors of functional groups are groups which can be converted into the desired functional group by the customary synthesis processes known to the person skilled in the art. For example, a cyano group which can be converted into an acid amide group or a carboxylic acid group by hydrolysis or can be converted into a tetrazole by reaction with an azide can be designated as a precursor for these groups. An alcohol group which can be oxidized to an aldehyde group can be designated as a precursor for this group. Examples of protective groups which are introduced into a molecule before carrying out a reaction or a reaction sequence and are later removed again have already been mentioned.

For the condensation of the compounds of the formulae II and III, the coupling methods of peptide chemistry which are well-known to the person skilled in the art are advantageously used (see, for example, Houben-Weyl, Methoden der Organischen Chemie, Volume 15/1 and 15/2, Georg Thieme Verlag, Stuttgart, 1974). Suitable condensing agents or coupling reagents are, for example, carbonyldiimidazole, carbodiimides such as dicyclohexylcarbodiimide (DCC) or diisopropylcarbodiimide, O-((cyano(ethoxycarbonyl)methylene)amino)-N,N,N',N'-tetramethyluronium tetrafluoroborate (TOTU) or propylphosphonic anhydride (PPA). The condensations can be carried out under the standard conditions well-known to the person skilled in the art. In general, they are carried out in an inert solvent or diluent, for example in an aprotic solvent such as N,N-dimethylformamide (DMF), dimethyl sulfoxide (DMSO), N-methyl-2-pyrrolidone (NMP), tetrahydrofuran (THF) or dimethoxyethane (DME). Depending on the condensation carried out in the individual case, it may be advantageous to add a base such as a tertiary amine or auxiliary reagents, for example an N-hydroxy compound such as 1-hydroxybenzotriazole (HOBT). The working-up of the reaction mixture and a purification of the product can be carried out by customary standard processes. After the condensation, the protective groups present are removed in a suitable manner. For example, benzyl groups in benzyl esters can be removed by hydrogenation or protective groups of the tert-butyl type can be removed acidically. The compounds of the formula I can also be prepared, for example, by synthesizing the compounds stepwise on a solid phase according to customary methods, it being possible to introduce the individual structural elements of the molecule in different sequences.

The amino compounds of the formula III are commercially available or can be synthesized by or analogously to well-known standard processes from starting compounds which are commercially available or, in turn, are obtainable by or analogously to literature procedures. For example, optically active 3-substituted 3-aminopropionic acids of the formula III or their esters, preferably 3-phenyl-3-aminopropionic acid esters, can be prepared from the corresponding 3-substituted acrylic acids, which in turn are obtainable from the corresponding aldehydes. The 3-substituted acrylic acids are converted into the acid chlorides using oxalyl chloride, and the acid chlorides are converted into the esters using an alcohol, for example into the tert-butyl esters using tert-butanol. For the introduction of the amino group, the ester is then reacted with the lithium salt of an optically active amine, for example the lithium salt of (R)-(+)-N-benzyl-N-(1-phenylethyl)amine, and subsequently, in the 3-substituted tert-butyl 3-(N-benzyl-N-(1-phenylethyl)amino)propionate obtained, the benzyl group and the phenylethyl group are removed by catalytic hydrogenation. For the preparation of compounds of the formula III in which E is the hydroxymethyl group $CH_2OH$ or an etherified or esterified hydroxymethyl group, 3-substituted 3-aminopropanols or their esters or ethers which are obtainable from the 3-substituted 3-aminopropionic acids or their esters by reduction of the acid group (or of the ester group), for example from the ethyl ester or tert-butyl ester using lithium aluminum hydride or lithium aluminum hydride/aluminum trichloride, can be employed in the condensation reaction.

Compounds of the formula II can be prepared, for example, by first reacting compounds of the formula IV

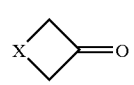

in a Bucherer reaction, for example with ammonium carbonate and potassium cyanide, to give compounds of the formula V

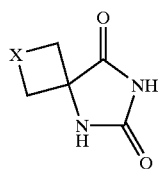

V where, in the formulae IV and V, the group X is defined as indicated above or a functional group can be present in protected form or in the form of a precursor. Compounds of the formula VI

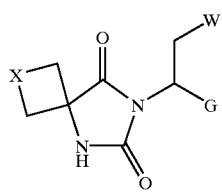

VI in which W, X and G are defined as indicated above or functional groups can be present in protected form or in the form of precursors, can then be obtained by reacting the compounds of the formula V, for example, with a first alkylating reagent of the formula LG—CH(G)—CH$_2$—W which introduces the residue —CH(G)—CH$_2$—W into the molecule. The reaction of compounds of the formula VI with a second alkylating reagent of the formula VIII

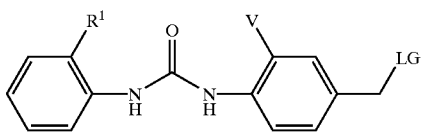

VII in which V and R$^1$ are defined as indicated above, then leads to the corresponding compounds of the formula II. The group LG is a nucleophilically substitutable leaving group, for example halogen such as chlorine or bromine, or sulfonyloxy such as tosyloxy, methylsulfonyloxy or trifluoromethylsulfonyloxy.

Compounds of the formula II can also be prepared, for example, by reacting a compound of the formula VI first with a reagent of the formula 4-(PG—NH)—C$_6$VH$_3$—CH$_2$—LG, in which LG in turn is a nucleophilically substitutable leaving group and the group V in the 3-position is hydrogen or methoxy, to give a compound of the formula VIII

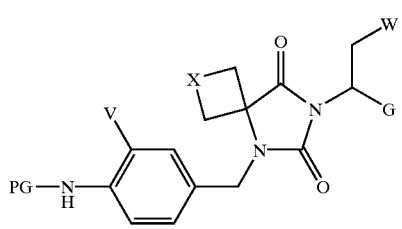

VIII where the meanings indicated above apply to G, V, W and X and PG is an amino protective group, for example tert-butoxycarbonyl or benzyloxycarbonyl. After removal of the protective group PG, the compounds of the formula II are obtained by reaction of the resulting amino group H$_2$N with phenyl isocyanate or with 2-methylphenyl isocyanate. Like compounds of the formula VIII, also compounds can be prepared and employed in which the group PG—NH— in the formula VIII is replaced by a group which is a precursor for an amino group and which is then converted into an amino group in a further reaction step. For example a compound of the formula VI can first be reacted with a nitro compound of the formula 4-O$_2$N—C$_6$VH$_3$—CH$_2$—LG to give a compound corresponding to the compound of the formula VIII, then the nitro group can be converted into the amino group, for example by catalytic hydrogenation, and then the amino group can be converted into the desired compound of the formula II using phenyl isocyanate or 2-methylphenyl isocyanate.

In case a compound of the formula I is to be prepared in which one of the CH$_2$ groups in the group X in the spiro-linked ring is replaced by a C=O group, it is expedient first to protect this carbonyl group, for example as a ketal, and to carry out the Bucherer reaction with the protected compound of the formula IV, for example the monoketal of the cycloalkanedione. The alkylations of the protected compound of the formula V to give the compounds of the formulae VI and VII are then carried out as explained and thereafter, or otherwise at a later time during the synthesis, the carbonyl group in the group X is liberated again. In the case of a ketal protective group, the liberation of the protected carbonyl group can be carried out by treating with an acid analogously to literature processes.

In general, the individual steps in the preparation of the compounds of the formula I can be carried out according to or analogously to known methods familiar to the person skilled in the art. As already mentioned and as is known to the person skilled in the art, depending on the individual case it may be appropriate in all steps in the synthesis of the compounds of the formula I temporarily to block functional groups which could lead to side reactions or undesired reactions by a protective group strategy tailored to the synthesis problem.

Compounds of the formula I can also be obtained as follows. By reaction of N-substituted amino acids obtainable by standard processes or preferably of their esters, for example the methyl esters, ethyl esters, tert-butyl esters or benzyl esters, for example of compounds of the formula IX

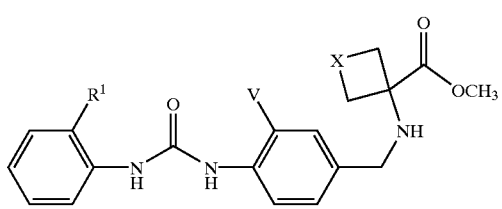

IX in which R$^1$, V and X are defined as indicated above, with an isocyanate of the formula X

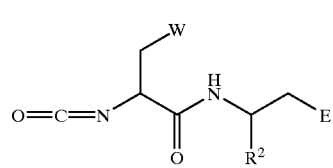

X for which the above definitions apply and which is obtainable according to standard processes from the corresponding compound which instead of the isocyanate group contains an H₂N group, urea derivatives, for example of the formula XI

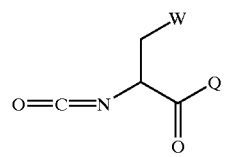
XI for which the definitions indicated above apply, are obtained. The compounds of the formula XI can then be cyclized to the compounds of the formula I by heating with acid. The cyclization of the compounds of the formula XI to the compounds of the formula I can also be carried out by treatment with bases in inert solvents, for example by treating with sodium hydride in an aprotic solvent such as dimethylformamide. During the reaction, functional groups can be present in protected form.

Compounds of the formula I can also be obtained by reacting a compound of the formula IX with an isocyanate of the formula XII XII
O=C=N—CH(Q)—W (structure)

in which Q, for example, is an alkoxy group, for example a (C₁–C₄)-alkoxy group such as methoxy, ethoxy or tert-butoxy, or a (C₆–C₁₄)-aryl-(C₁–C₄)-alkoxy group, for example benzyloxy, and W has the meanings indicated above. In this case, a compound of the formula XIII is obtained XIII
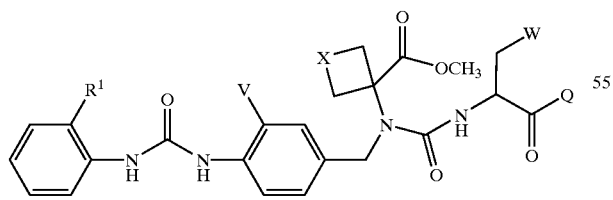

in which X, W, V, Q and R¹ are defined as indicated above, which is then cyclized under the influence of an acid or of a base, as described above for the cyclization of the compounds of the formula XI, to a compound of the formula XIV XIV
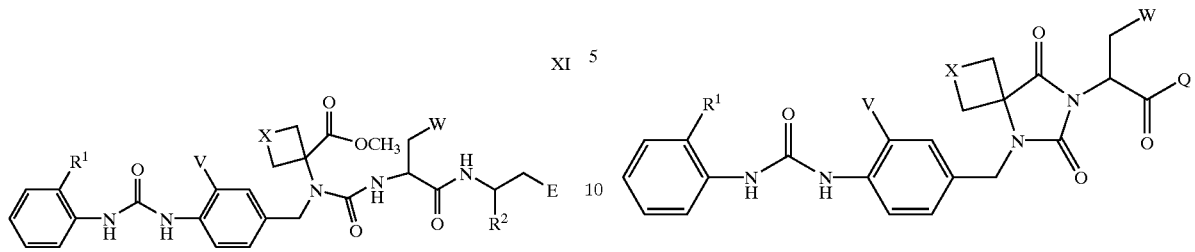

in which Q, W, V, X and R¹ are defined as indicated above. In the compound of the formula XIV, it is then possible, for example by means of hydrolysis, to convert the group CO—Q into the carboxylic acid group COOH. If the cyclization of the compound of the formula XII to the compound of the formula XIV is carried out using an acid, the conversion of the group CO—Q into the group COOH can also be carried out simultaneously with the cyclization. By subsequent coupling with a compound of the formula III, as described above for the coupling of the compounds of the formulae II and III, a compound of the formula I is then obtained. In this synthesis process too, functional groups can be present in protected form or in the form of precursors.

A further method for the preparation of compounds of the formula I is, for example, the reaction of compounds of the formula XV XV
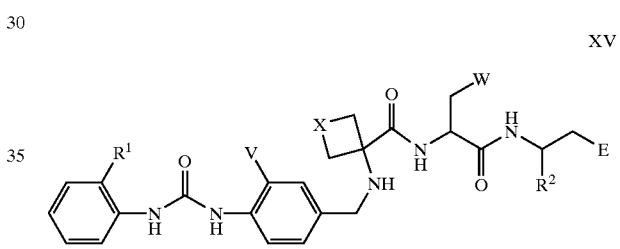

for which the definitions indicated above apply, with phosgene or corresponding equivalents (analogously to S. Goldschmidt and M. Wick, Liebigs Ann. Chem. 575 (1952), 217 and C. Tropp, Chem. Ber. 61 (1928), 1431).

Compounds of the formula I can also be prepared by first coupling a compound of the formula XVI XVI
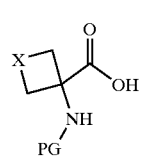

in which X has the meanings indicated above and PG is an amino protective group such as, for example, a benzyloxycarbonyl group, to a compound of the formula XVII XVII
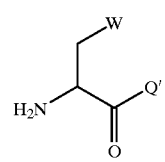

in which Q' is a protected carboxylic acid hydroxy group, for example an alkoxy group such as tert-butoxy, and W has the meanings indicated above, to give a compound of the formula XVIII

XVII

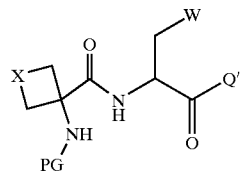

in which X, W, PG and Q' have the meanings indicated above. In the compound of the formula XVIII, it is then possible to remove the protective group PG from the amino group selectively, for example by hydrogenation in the case of a benzyloxycarbonyl group, and by introduction of a CO group a ring closure can be carried out to give a compound of the formula XIX

XIX

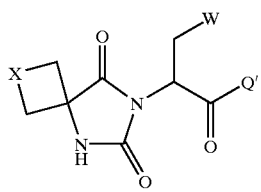

in which X, W and Q' have the meanings indicated above. For the introduction of the carbonyl group, it is possible to use, for example, phosgene or a phosgene equivalent (analogously to the reaction of the compounds of the formula XV illustrated above). An intermediate which can occur or can be specifically prepared in the conversion of the compound of the formula XVIII into the compound of the formula XIX is, for example, an isocyanate. The conversion of the compound of the formula XVIII into that of the formula XIX can be carried out in one or more steps. For example, the carbonyl group can first be introduced into the molecule and in a separate step the cyclization can then be carried out in the presence of a base such as sodium hydride, like the cyclizations described above. Compounds of the formula XVIII, in which PG is the benzyloxycarbonyl group, can also be converted directly into compounds of the formula XIX without an additional synthesis component such as phosgene being employed for the introduction of the carbonyl group. If compounds of the formula XVIII in which PG is benzyloxycarbonyl are treated with a base such as sodium hydride, the compounds of the formula XIX can be obtained directly.

The compounds of the formula XIX can then be alkylated on the NH group using a reagent of the formula VII, for example, as illustrated above for the compounds of the formula VI, and after conversion of the protected carboxylic acid group CO—Q' into the carboxylic acid group COOH, the desired compounds of the formula I can be synthesized as described above for the compounds of the formulae VI and II. In this synthesis process too, functional groups can be present in protected form or in the form of precursors.

Compounds of the formula I can furthermore be prepared by first reacting a compound of the formula XX

X

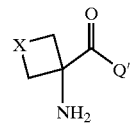

in which X and Q' have the meanings indicated above, with an isocyanate of the formula XII to give a compound of the formula XXI

XXI

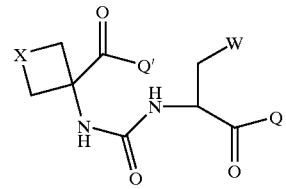

in which X, W, Q and Q' have the meanings indicated above. The compound of the formula XXI is then cyclized by treating with a strong acid, for example half-concentrated hydrochloric acid, to a compound of the formula XXII.

XXII

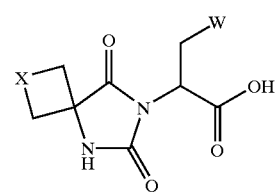

Compounds of the formula XXII can also be prepared by first preparing a compound of the formula XVIII in which X, W and Q' have the meanings indicated and PG is an alkoxycarbonyl group such as $(C_1-C_4)$-alkoxycarbonyl, an arylalkoxycarbonyl group such as phenyl-$(C_1-C_4)$-alkoxycarbonyl, or an aryloxycarbonyl group such as phenyloxycarbonyl, converting it by liberating the protected carboxylic acid group CO—Q' into a compound of the formula XVIII in which CO—Q' is the free carboxylic acid group CO—OH, PG is alkoxycarbonyl, arylalkoxycarbonyl or aryloxycarbonyl and X and W have the meanings indicated, and cyclizing this compound with a base such as, for example, sodium carbonate to the compound of the formula XXII.

Compounds of the formula IIa,

IIa

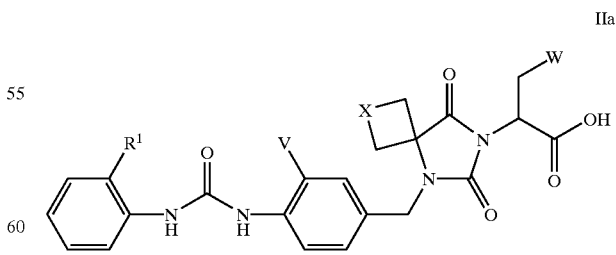

in which $R^1$, V, W and X have the meanings indicated above, can then be obtained by reacting the compounds of the formula XXII with an alkylating reagent of the formula VII in the presence of excess base, for example in the presence of an excess of n-butyllithium, and then acidifying. The 4-(3-arylureido)benzyl group can also be introduced into the compounds of the formula XXII stepwise, analogously to the preparation of the compounds of the formula VII and the compounds of the formula II obtained therefrom. If, in the compounds of the formula XXII, a $CH_2$ group in the group X is replaced by a carbonyl group, it is expedient to protect this carbonyl group for the alkylation reactions to give the compounds of the formula IIa and to liberate it again after the alkylation, as has been explained above.

The compounds of the formula I in which E, for example, is hydroxycarbonyl or hydroxymethyl can be converted by standard processes into compounds of the formula I in which E has other meanings, or into other prodrugs or derivatives of the compounds of the formula I. Thus, for the preparation of esters the compounds of the formula I in which E is hydroxycarbonyl can be esterified with the corresponding alcohols, for example in the presence of a condensing reagent such as DCC, or the compounds of the formula I in which E is hydroxycarbonyl can be alkylated using alkyl halides such as alkyl chlorides or alkyl bromides, for example using chloroalkanamides to give compounds of the formula I in which E is $R^4R^4N$—CO-alkoxy-CO—, or with acyloxyalkyl halides to give compounds of the formula I in which E is acyloxyalkoxy-CO—. Compounds of the formula I in which E is hydroxycarbonyl can be converted into amides using ammonia or organic amines in the presence of a condensing reagent. Compounds of the formula I in which E is CO—$NH_2$ can advantageously also be obtained on the solid phase, by coupling the compound in which E is COOH to Rink amide resin in the presence of a condensing agent such as TOTU and then removing it again from the resin using trifluoroacetic acid. Compounds of the formula I in which E is the hydroxymethyl group $CH_2OH$ can be etherified or esterified on the hydroxymethyl group according to standard processes. According to standard processes for the selective oxidation of alcohols to aldehydes, for example using sodium hypochlorite in the presence of 4-acetamido-2,2,6,6-tetramethylpiperidin-1-oxyl (4-acetamido-TEMPO), compounds of the formula I in which E is $CH_2OH$ can be converted into compounds of the formula I in which E is the aldehyde group CO—H.

The compounds of the formula I are valuable pharmaceutical active compounds which are suitable, for example, for treating subjects in need of treatment. As used herein, "treating" or "treatment" includes the therapy and/or amelioration of a condition. However, "treating" or "treatment" also includes the prophylaxis or prevention of a condition. Such conditions include, but are not limited to diseases (or illnesses), such as, for example, inflammatory diseases, allergic diseases or asthma. In one embodiment, the invention relates to a method of treating a subject having asthma or an allergy, thereby preventing an acute asthma attack or allergic reaction. The compounds of the formula I and their physiologically acceptable salts and derivatives can be administered according to the invention to treat animals, preferably mammals, and most preferably to humans, as pharmaceuticals for therapy and/or prophylaxis. They can be administered on their own, in mixtures with one another or in the form of pharmaceutical preparations which allow enteral or parenteral use and which, as active constituent, contain an efficacious dose of at least one compound of the formula I and/or its physiologically acceptable salts and derivatives in addition to pharmaceutically innocuous vehicles and/or additives. The compounds of the formula I are administered in an amount effective for the treatment and/or prophylaxis of the condition.

The present invention therefore also relates to the compounds of the formula I and/or their physiologically acceptable salts and derivatives for use as pharmaceuticals, the use of the compounds of the formula I and/or their physiologically acceptable salts and derivatives for the production of pharmaceuticals for the treatment, such as therapy and prophylaxis, of the illnesses illustrated above and in the following, for example for the treatment, such as therapy and prophylaxis, of inflammatory diseases, and the use of the compounds of the formula I and/or their physiologically acceptable salts and derivatives in the treatment, such as therapy and prophylaxis, of these illnesses. The present invention furthermore relates to pharmaceutical preparations (or pharmaceutical compositions) which contain an efficacious dose of at least one compound of the formula I and/or its physiologically acceptable salts and derivatives and a pharmaceutically acceptable carrier, that is one or more pharmaceutically innocuous vehicles and/or additives.

The pharmaceuticals can be administered systemically or locally. They can be administered, for example, orally in the form of pills, tablets, film-coated tablets, sugar-coated tablets, granules, hard and soft gelatin capsules, powders, solutions, syrups, emulsions, suspensions and in other pharmaceutical forms. The administration can also be carried out vaginally or rectally, for example in the form of suppositories, or parenterally or by implantation, for example in the form of injection solutions or infusion solutions, microcapsules or rods, or topically or percutaneously, for example in the form of creams, ointments, powders, solutions, emulsions or tinctures, or in other ways, for example in the form of nasal sprays or aerosol mixtures. Parenteral administration of solutions can occur, for example, intravenously, intramuscularly, subcutaneously, intraarticularly, intrasynovially or in other ways.

The pharmaceutical preparations according to the invention are produced in a known manner, the compound or the compounds of the formula I and/or its physiologically acceptable salts and derivatives being mixed with pharmaceutically inert inorganic and/or organic vehicles and/or additives. For the production of pills, tablets, coated tablets and hard gelatin capsules, for example lactose, corn starch or derivatives thereof, talc, stearic acid or its salts, polyethylene glycols, etc. may be used. For soft gelatin capsules and suppositories, for example, fats, waxes, semisolid and liquid polyols, polyethylene glycols, natural or hardened oils etc. may be used. Suitable vehicles for the production of solutions, for example injection solutions, or of emulsions or syrups are, for example, water, alcohols, glycerol, diols, polyols, sucrose, invert sugar, glucose, vegetable oils etc. Suitable vehicles for microcapsules, implants or rods are, for example, copolymers of glycolic acid and lactic acid. The pharmaceutical preparations normally contain about 0.5 to about 90% by weight of the compounds of the formula I and/or their physiologically acceptable salts and derivatives. The amount of active compound of the formula I and/or its physiologically acceptable salts and derivatives in the pharmaceutical preparations is normally about 0.2 to about 1000 mg, preferably about 1 to about 500 mg, but depending on the nature of the pharmaceutical preparation the amount of the active compound can also be larger.

In addition to the active compounds and vehicles, the pharmaceutical preparations can additionally contain excipients or additives, for example fillers, disintegrants, binders, lubricants, wetting agents, stabilizing agents, emulsifiers, preservatives, sweeteners, colorants, flavorings, aromatizers, thickening agents, diluents, buffer substances, solvents, solubilizers, agents for achieving a depot effect, salts for changing the osmotic pressure, coating agents or antioxidants. They can also contain two or more compounds of the formula I and/or their physiologically acceptable salts and derivatives. Furthermore, in addition to at least one compound of the formula I and/or its physiologically acceptable salts and derivatives they can contain one or more other pharmaceutical active compounds, for example substances having antiinflammatory action.

If the compounds of the formula I or pharmaceutical preparations comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the formula I as an aerosol can be prepared by processes well-known to the person skilled in the art. For their preparation, for example, solutions or dispersions of the compounds of the formula I in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example chlorofluorohydrocarbons and/or fluorohydrocarbons.

Suitable other pharmaceutical active compounds which can be contained in addition to compounds of the formula I in the pharmaceutical preparations according to the invention, but with which the compounds of the formula I can also be combined in other ways in the context of a combination therapy or combination prophylaxis, are preferably such active compounds which are suitable for the therapy or prophylaxis of the illnesses mentioned above or in the following for whose therapy or prophylaxis the compounds of the formula I are suitable. Examples of classes of active compound of this type which may be mentioned are steroids, nonsteroidal antiinflammatory substances, nonsteroidal antiinflammatory acetic acid derivatives, nonsteroidal antiinflammatory propionic acid derivatives, nonsteroidal antiasthmatics, salicylic acid derivatives, pyrazolones, oxicams, leukotriene antagonists, inhibitors of leukotriene biosynthesis, cyclooxygenase inhibitors, cyclooxygenase-2 inhibitors, (COX-2 inhibitors), antihistamines, H1-histamine antagonists, nonsedating antihistamines, gold compounds, β2 agonists, anticholinergics, muscarine antagonists, antihyperlipidemics, antihypercholesterolemics, HMG-CoA reductase inhibitors, statins, nicotinic acid derivatives, immunosuppressants, cyclosporins, β-interferons, tumor therapeutics, cytostatics, metastasis inhibitors, antimetabolites, 5-aminosalicylic acid derivatives, antidiabetics, insulins, sulfonylureas, biguanides, glitazones, α-glucosidase inhibitors, and others. Examples of suitable active compounds which may be mentioned are acetylsalicylic acid, benorilate, sulfasalazine, phenylbutazone, oxyphenbutazone, metamizole, mofebutazone, feprazone, celecoxib, rofecoxib, diclofenac, fentiazac, sulindac, zomepirac, tolmetin, indometacin, acemetacin, ibuprofen, naproxen, carprofen, fenbufen, indoprofen, ketoprofen, pirprofen, tiaprofenic acid, diflunisal, flufenamic acid, meclofenamic acid, mefenamic acid, niflumic acid, tolfenamic acid, piroxicam, isoxicam, tenoxicam, nicotinic acid, prednisone, dexamethasone, hydrocortisone, methylprednisolone, betamethasone, beclomethasone, budesonide, montekulast, prankulast, zafirkulast, zileutone, ciclosporin, rapamycin, tacrolimus, methotrexate, 6-mercaptopurine, azathioprine, interferon-beta-1a, interferon-beta-1b, 5-aminosalicylic acid, leflunomide, D-penicillamine, chloroquine, glibenclamide, glimepiride, troglitazone, metformin, acarbose, atorvastatin, fluvastatin, lovastatin, simvastatin, pravastatin, colestipol, colestyramine, probucol, clofibrate, fenofibrate, bezafibrate, gemfibrozil, ipatropium bromide, clenbuterol, fenoterol, metaproterenol, pirbuterol, tulobuterol, salbutamol, salmeterol, terbutalin, isoetarine, ketotifen, ephedrine, oxitropium bromide, atropine, cromoglycic acid, theophylline, fexofenadine, terfenadine, cetirizine, dimetindene, diphenhydramine, diphenylpyraline, pheniramine, bromopheniramine, chlorpheniramine, dexchlorpheniramine, alimemazine, antazoline, astemizole, azatadine, clemastine, cyproheptadine, hydroxyzine, loratidine, mepyramine, promethazine, tripelennamine, triprolidine and others.

If compounds of the formula I and/or their physiologically acceptable salts or prodrugs are to be employed in a combination therapy or combination prophylaxis together with one or more other active compounds, this can be carried out as mentioned by administering all active compounds together in a single pharmaceutical preparation, for example a tablet or capsule. Pharmaceutical preparations of this type, for which all explanations above correspondingly apply, are expressly likewise a subject of the present invention. The amount of the active compounds in these pharmaceutical preparations is in general such that an efficacious amount of each active compound is present. A combination therapy or combination prophylaxis, however, can also be carried out by the active compounds being present in two or more separate pharmaceutical preparations which can be in a single pack or in two or more separate packs. The administration of the compounds of the formula I and/or their physiologically acceptable salts or products and the other active compounds can be carried out jointly or separately and can be carried out simultaneously or sequentially, in any order. The administration can also be carried out in different ways, for example one active compound can be administered orally and the other by injection, inhalation or topical application.

The compounds of the formula I have, for example, the ability to inhibit cell-cell interaction processes and cell-matrix interaction processes in which interactions between VLA-4 and its ligands play a role. The activity of the compounds of the formula I can be demonstrated, for example, in an assay in which the binding of cells which contain the VLA-4 receptor, for example of leukocytes, to ligands of this receptor, for example to VCAM-1 which advantageously can also be prepared for this purpose by genetic engineering, is measured. Details of such an assay are described below. In particular, the compounds of the formula I are able to inhibit the adhesion and the migration of leukocytes, for example the adhesion of leukocytes to endothelial cells which—as explained above—is controlled via the VCAM-1VLA-4 adhesion mechanism. Apart from as antiinflammatory substances, the compounds of the formula I and their physiologically acceptable salts and derivatives are therefore generally suitable for the therapy and prophylaxis of illnesses which are based on the interaction between the VLA-4 receptor and its ligands or can be affected by an inhibition of this interaction, and they are preferably suitable for the therapy and prophylaxis of illnesses which are at least partially caused by an undesired extent of leukocyte adhesion and/or leukocyte migration or are associated therewith, and for whose prevention, alleviation or cure the adhesion and/or migration of leukocytes should be decreased.

The present invention therefore also relates to the compounds of the formula I and their physiologically acceptable salts and derivatives for the inhibition of the adhesion and/or migration of leukocytes or for the inhibition of the VLA-4 receptor, and to the use of the compounds of the formula I for the production of pharmaceuticals for this, that is of pharmaceuticals for the therapy or prophylaxis of illnesses in which leukocyte adhesion and/or leukocyte migration exhibits an undesired extent, or for the therapy or prophylaxis of illnesses in which VLA-4-dependent adhesion processes play a part, and to the use of the compounds of the formula I and/or their physiologically acceptable salts and derivatives in the therapy and prophylaxis of illnesses of this type.

The compounds of the formula I can be employed as antiinflammatories in the case of inflammatory symptoms of very different causes in order to prevent, to decrease or to suppress the undesired or harmful consequences of inflammation. They are used, for example, for the therapy or prophylaxis of arthritis, of rheumatoid arthritis, of polyarthritis, of inflammatory bowel disease (ulcerative colitis), of systemic lupus erythematosus, for the therapy or prophylaxis of inflammatory disorders of the central nervous system such as, for example, of multiple sclerosis, or for the therapy or prophylaxis of asthma or of allergies, for example allergies of the delayed type (type IV allergy). They are furthermore suitable for the therapy or prophylaxis of cardiovascular disorders, of arteriosclerosis, of restenoses, of diabetes, of damage to organ transplants, of immune disorders, of autoimmune disorders, of tumor growth or tumor metastasis in various malignancies, of malaria as well as of further illnesses in which blocking of the integrin VLA-4 and/or influencing of the leukocyte activity appears appropriate for prevention, alleviation or cure.

The dose when using the compounds of the formula I can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the formula I. In general, in the case of oral administration, a daily dose of about 0.01 to about 100 mg/kg, preferably about 0.1 to about 10 mg/kg (in each case mg of the compound per kg of body weight) is appropriate in an adult weighing about 75 kg to achieve effective results. In the case of intravenous administration, the daily dose is in general about 0.01 to about 50 mg/kg of body weight, preferably about 0.01 to about 10 mg/kg. The daily dose can be divided, especially when relatively large amounts are administered, into several, for example 2, 3 or 4, part administrations. If appropriate, depending on individual behavior, it may be necessary to deviate upward or downward from the daily dose indicated.

Apart from as pharmaceutical active compounds in human medicine and veterinary medicine, the compounds of the formula I and their salts and derivatives suitable for the use concerned can furthermore be employed for diagnostic purposes, for example in in-vitro diagnoses of cell samples or tissue samples, and as auxiliaries or as a scientific tool in biochemical investigations in which VLA-4 blocking or influencing of cell-cell or cell-matrix interactions is demanded. Furthermore, the compounds of the formula I and their salts can be used as intermediates for the preparation of other compounds, in particular of other pharmaceutical active compounds which are obtainable from compounds of the formula I, for example by modification or introduction of residues or functional groups, for example by esterification, reduction, oxidation or other conversions of functional groups.

EXAMPLES

The invention will now be described with reference to the following examples. It should be understood that these examples are provided merely for illustration and should not be construed as limiting the present invention.

Example 1

(S)-3-((S)-2-(4,4-Pentamethylene-3-(4-(3-phenylureido)benzyl)-2,5-dioxoimidazolidin-1-yl)-2-(2-methylpropyl)acetylamino)-3-phenylpropionic acid

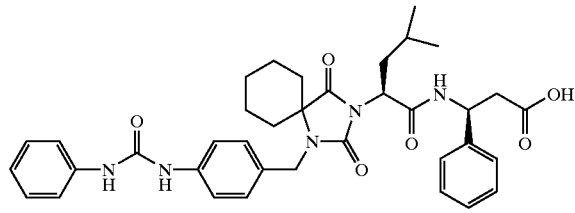

a) 4-(3-Phenylureido)benzyl alcohol 30.6 g (200 mmol) of 4-nitrobenzyl alcohol were hydrogenated over 1.0 g of palladium/carbon (10% strength; 50% water) in 500 ml of methyl tert-butyl ether. After the absorption of hydrogen was complete, the catalyst was filtered off. 24 g (200 mmol) of phenyl isocyanate were added to the filtrate at 15° C. with stirring in the course of 30 minutes. The precipitated solid was filtered off with suction and washed with methyl tert-butyl ether. Yield: 43 g (89%).

b) 4-(3-Phenylureido)benzyl chloride 42 g (354 mmol) of thionyl chloride were added dropwise at 30° C. to a suspension of 42.8 g (177 mmol) of 4-(3-phenylureido)benzyl alcohol in 500 ml of dichloromethane. The mixture was subsequently stirred at 40° C. for 1 hour. After completion of the evolution of gas, the mixture was allowed to cool to room temperature. The precipitated product was filtered off with suction and washed with dichloromethane. Yield: 44.26 g (96%).

c) Methyl 1-aminocyclohexane-1-carboxylate 51 ml of thionyl chloride were added in portions at −5° C. to 50 g (350 mmol) of 1-aminocyclohexane-1-carboxylic acid in 1.25 l of methanol. The reaction mixture was subsequently stirred at room temperature for 5 hours and allowed to stand overnight at room temperature. The methanol was removed in vacuo, the residue was mixed with water, and the aqueous solution was adjusted to pH 9 using saturated sodium carbonate solution and extracted twice with dichloromethane. The organic phase was dried over sodium sulfate and, after filtration, the solvent was removed in vacuo. Yield: 36.35 g (66%).

d) Methyl 1-(3-((S)-1-tert-butoxycarbonyl-3-methylbutyl)ureido)cyclohexanecarboxylate A solution of 28 g (179 mmol) of methyl 1-aminocyclohexane-1-carboxylate was added to a solution of 38 g (179 mmol) of L-leucine tert-butyl ester isocyanate (prepared analogously to J. S. Nowick et al., J. Org. Chem. 1996, 61, 3929) in 300 ml of absolute DMF. After stirring at room temperature for 2 hours, the reaction mixture was allowed to stand overnight. The solvent was removed in vacuo, the residue was treated with heptane and the mixture was stirred at room temperature for 2 hours. The precipitate was filtered off with suction and washed with heptane. Yield: 45.94 g (69%).

e) (S)-2-(4,4-Pentamethylene-2,5-dioxoimidazolidin-1-yl)-2-(2-methylpropyl)acetic acid 11.4 g (30.8 mmol) of methyl 1-(3-((S)-1-tert-butoxycarbonyl-3-methylbutyl)ureido)cyclohexanecarboxylate were heated at 60° C. for 8 hours in 200 ml of 6 N hydrochloric acid, and the mixture was allowed to stand at room temperature overnight and then extracted with diethyl ether. The combined extracts were concentrated in vacuo, and the residue was taken up with a little acetonitrile, treated with water and freeze-dried. Yield: 8.28 g (95%).

f) (S)-2-(4,4-Pentamethylene-3-(4-(3-phenylureido)benzyl)-2,5-dioxoimidazolidin-1-yl)-2-(2-methylpropyl)acetic acid 21 ml of an n-butyllithium solution (2.5 M in hexane) were added at −76° C. under argon to a solution of 7.4 g (26.24 mmol) of (S)-2-(4,4-pentamethylene-2,5-dioxoimidazolidin-1-yl)-2-(2-methylpropyl)acetic acid in 150 ml of absolute THF. After stirring at −76° C. for 30 minutes, the reaction mixture was allowed to warm to 0° C. and 6.82 g (26.24 mmol) of 4-(3-phenylureido)benzyl chloride were added in portions. After stirring at 0° C. for 30 minutes, the mixture was adjusted to pH 1 by addition of 1 N hydrochloric acid, diluted with water and extracted with ethyl acetate. After separating the phases, the organic phase was dried over sodium sulfate and, after filtration, the solvent was removed in vacuo. The residue thus obtained was purified by means of preparative HPLC. Yield: 2.18 g (16%).

g) Ethyl (S)-3-((S)-2-(4,4-pentamethylene-3-(4-(3-phenylureido)benzyl)-2,5-dioxoimidazolidin-1-yl)-2-(2-methylpropyl)acetylamino)-3-phenylpropionate 525 mg (1.42 mmol) of TOTU and 230 µl (1.35 mmol) of N,N-diisopropylethylamine were added successively with ice-cooling to a solution of 720 mg (1.42 mmol) of (S)-2-(4,4-pentamethylene-3-(4-(3-phenylureido)benzyl)-2,5-dioxoimidazolidin-1-yl)-2-(2-methylpropyl)acetic acid and 274 mg (1.42 mmol) of ethyl (S)-3-amino-3-phenylpropionate (prepared from the hydrochloride) in 20 ml of absolute DMF. After 1 hour at room temperature, the solvent was removed in vacuo, the residue was dissolved in ethyl acetate and the ethyl acetate solution was successively washed twice in each case with an aqueous KHSO$_4$/K$_2$SO$_4$ solution, a saturated NaHCO$_3$ solution and a saturated sodium chloride solution. After drying the organic phase over sodium sulfate and filtering, the solvent was removed in vacuo and the residue was chromatographed on silica gel using ethyl acetate/heptane (1/1). After concentrating the product fractions, 826 mg (85%) of the title compound were obtained.

h) (S)-3-((S)-2-(4,4-Pentamethylene-3-(4-(3-phenylureido)benzyl)-2,5-dioxoimidazolidin-1-yl)-2-(2-methylpropyl)acetylamino)-3-phenylpropionic acid 3.61 ml of a 1 M lithium hydroxide solution were added to 820 mg (1.2 mmol) of ethyl (S)-3-((S)-2-(4,4-pentamethylene-3-(4-(3-phenylureido)benzyl)-2,5-dioxoimidazolidin-1-yl)-2-(2-methylpropyl)acetylamino)-3-phenylpropionate in 30 ml of methanol and the mixture was stirred at room temperature overnight. After fresh addition of 10 ml of methanol and 1.2 ml of 1 M lithium hydroxide solution and stirring overnight, 30 ml of water were added and the methanol was largely removed in vacuo. The residual aqueous phase was adjusted to pH 1 by addition of 1 N hydrochloric acid and extracted twice with ethyl acetate. The combined organic phases were washed with water, dried over sodium sulfate and concentrated. 760 mg of the crude product obtained were dissolved in acetonitrile/water and freeze dried. 639 mg of the title compound were obtained.

ES(+)-MS: 654.4 (M+H)$^+$.

Process for the Preparation of the Starting Compound ethyl (S)-3-amino-3-phenylpropionate hydrochloride i) (R)-2-Amino-2-phenylethanol 20 g (920 mmol) of lithium borohydride were dissolved in 420 ml of absolute THF. 233.5 ml (1.84 mol) of trimethylchlorosilane were added dropwise with stirring and 69.5 g (0.46 mol) of (R)-phenylglycine were then added in portions in the course of 4 hours. The reaction mixture was stirred overnight at room temperature. 690 ml of methanol were then added, and the mixture was stirred at room temperature for 2 hours and concentrated in vacuo. The residue was dissolved in 690 ml of 20% strength aqueous potassium hydroxide solution with stirring. The aqueous phase was extracted three times with ethyl acetate. The combined organic phases were washed with water, dried over magnesium sulfate and concentrated in vacuo. Yield: 41.2 g (65.3%).

FAB-MS: 138 (M+H)$^+$.

j) (R)-2-Benzyloxycarbonylamino-2-phenylethanol 40.5 g (295 mol) of (R)-2-amino-2-phenylethanol were dissolved in 385 ml of absolute DMF. 73.5 g of N-(benzyloxycarbonyloxy)succinimide (295 mmol) were added at 0° C. with stirring and the mixture was stirred at 0° C. for 1 hour. The ice bath was removed and the batch was allowed to stand at room temperature for 48 hours. The reaction solution was concentrated in vacuo and the residue was then taken up in 500 ml of ethyl acetate. The organic phase was washed twice with 10% strength aqueous citric acid solution and once with water. It was dried over anhydrous sodium sulfate and concentrated. The crystalline crude product obtained (82.3 g) was dissolved again in ethyl acetate. The organic phase was washed twice with 10% strength aqueous citric acid solution and once with water and concentrated. The residue was then recrystallized from ethyl acetate/petroleum ether. Yield: 74.6 g (93.3%).

FAB-MS: 272 (M+H)$^+$.

k) (R)-2-Benzyloxycarbonylamino-2-phenylethyl 4-methylphenylsulfonate 53.9 g of (R)-2-benzyloxycarbonylamino-2-phenylethanol (198.7 mmol) were dissolved in a mixture of 500 ml of methylene chloride and 80.3 ml (993.5 mmol) of pyridine. 45.5 g (238.4 mmol) of tosyl chloride in 240 ml of methylene chloride were added at 0° C. with stirring and the mixture was stirred at room temperature for 7 hours. A further 11.36 g of tosyl chloride (59.61 mmol) were added. The mixture was stirred at 0° C. for 5 hours. The batch was then allowed to stand overnight at room temperature and concentrated in vacuo. The residue was taken up in ethyl acetate. The organic phase was washed three times with 10% strength aqueous citric acid solution and twice with water, dried over magnesium sulfate and concentrated in vacuo. The residue was triturated with diethyl ether, filtered off with suction, washed with diethyl ether and dried over phosphorus pentoxide. Yield: 60.9 g (72%). The mother liquor was concentrated, taken up in n-heptane/ethyl acetate (6/4) and chromatographed on silica gel to give an additional yield of 3.5 g (4.2%).

Total yield: 64.4 g (76.2%).

FAB-MS: 426 (M+H)$^+$.

l) (S)-3-Benzyloxycarbonylamino-3-phenylpropionitrile 60.5 g of (R)-2-benzyloxycarbonylamino-2-phenylethyl 4-methylphenylsulfonate (142.2 mmol) were dissolved in 675 ml of DMF. 13.9 g of potassium cyanide (213.3 mmol), 5.64 g of 18-crown-6 (21.33 mmol) and 520 mg of potassium iodide (3.13 mmol) were added and the mixture was stirred at 50° C. for 20 hours. The reaction solution was poured into 500 ml of ice water and then stirred at 0° C. for 5 hours. The precipitate was filtered off with suction and dissolved in ethyl acetate. The organic phase was washed three times with water, dried over magnesium sulfate and concentrated in vacuo. The residue was triturated with diethyl ether, filtered off with suction, washed with diethyl ether and dried over phosphorus pentoxide. Yield: 25.3 g (63.5%).

FAB-MS: 281 (M+H)$^+$.

m) Ethyl (S)-3-benzyloxycarbonylamino-3-phenylpropionate 15 g of (S)-3-benzyloxycarbonylamino-3-phenylpropionitrile (53.51 mmol) were suspended in a mixture of 110 ml of absolute ethanol and 30 ml of dioxane. HCl gas was passed in at 10–15° C. with stirring and cooling. After a short time, a clear solution was formed. Further HCl gas was passed in with cooling until starting material was no longer detectable in the thin-layer chromatogram. Nitrogen was then passed through the reaction solution for 15 minutes and it was then concentrated in vacuo. The residue was treated with water until turbidity persisted. The mixture was stirred at room temperature for 30 minutes and the aqueous phase was then extracted three times with ethyl acetate. The combined organic phases were washed with water, dried over magnesium sulfate and concentrated in vacuo. The residue was taken up in ethyl acetate/petroleum ether (1/1) and chromatographed on silica gel. Yield: 10.55 g (60%).

FAB-MS: 328 (M+H)$^+$.

n) Ethyl (S)-3-amino-3-phenylpropionate hydrochloride 10.29 g of ethyl (S)-benzyloxycarbonylamino-3-phenylpropionate (31.44 mmol) were dissolved in 125 ml of ethanol and catalytically hydrogenated over palladium/carbon at a pH of 4 in an autoburette with addition of 2 N ethanolic HCl. The catalyst was filtered off with suction through kieselguhr and the filtrate was concentrated. The residue was triturated with diethyl ether, filtered off with suction, washed with diethyl ether and dried over phosphorus pentoxide. Yield: 5.05 g (70%).

FAB-MS: 194 (M+H)$^+$.

Example 2

(S)-3-((S)-2-(4,4-Pentamethylene-3-(4-(3-phenylureido)benzyl)-2,5-dioxoimidazolidin-1-yl)-2-(2-methylpropyl)acetylamino)-3-phenylpropionic acid tromethamine salt

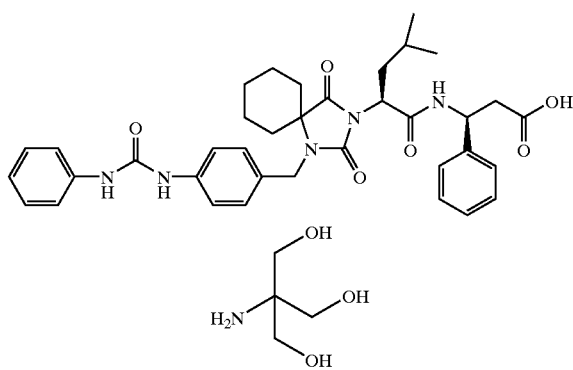

100 mg of (S)-3-((S)-2-(4,4-pentamethylene-3-(4-(3-phenylureido)benzyl)-2,5-dioxoimidazolidin-1-yl)-2-(2-methylpropyl)acetylamino)-3-phenylpropionic acid were suspended in 15 ml of water, treated with 20.4 mg of α,α,α-tris(hydroxymethyl)methylamine and the mixture was stirred at room temperature for 30 minutes. Insoluble components were filtered off and the filtrate was freeze dried. 105 mg of an (S)-3-((S)-2-(4,4-pentamethylene-3-(4-(3-phenylureido)benzyl)-2,5-dioxoimidazolidin-1-yl)-2-(2-methylpropyl)acetylamino)-3-phenylpropionic acid tromethamine salt were obtained, which according to the $^1$H-NMR spectrum contained 1.3 mol of tromethamine per mole of (S)-3-((S)-2-(4,4-pentamethylene-3-(4-(3-phenylureido)benzyl)-2,5-dioxoimidazolidin-1-yl)-2-(2-methylpropyl)acetylamino)-3-phenylpropionic acid.

ES(+)-MS: 122.0 (α,α,α-tris(hydroxymethyl)methylamine+H)$^+$; 654.4 (3-(2-(4,4-pentamethylene-3-(4-(3-phenylureido)benzyl)-2,5-dioxoimidazolidin-1-yl)-2-(2-methylpropyl)acetylamino)-3-phenylpropionic acid+H)$^+$; 775.4.

Example 3

(R)-3-((S)-2-(4,4-Pentamethylene-3-(4-(3-phenylureido)benzyl)-2,5-dioxoimidazolidin-1-yl)-2-(2-methylpropyl)acetylamino)-3-methylpropionic acid

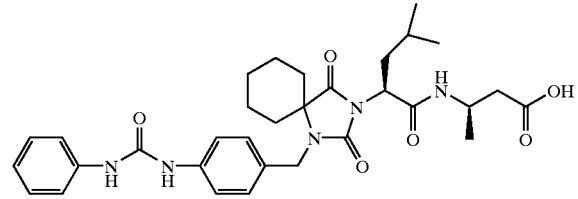

132 mg (0.988 mmol) of HOBT and 245 mg (1.18 mmol) of DCC were added with ice cooling to a solution of 500 mg (0.988 mmol) of (S)-2-(4,4-pentamethylene-3-(4-(3-phenylureido)benzyl)-2,5-dioxoimidazolidin-1-yl)-2-(2-methylpropyl)acetic acid in 15 ml of absolute DMF. After stirring with ice cooling for 1 hour, 157 mg (0.988 mmol) of tert-butyl (R)-3-aminobutanoate were added. After stirring at room temperature for 3 hours and allowing to stand overnight, the reaction mixture was filtered and the filtrate was concentrated in vacuo. The residue was taken up in ethyl acetate and in each case washed twice with an aqueous KHSO$_4$/K$_2$SO$_4$ solution and water. After drying the organic phase over sodium sulfate and filtering, the solvent was removed in vacuo. The residue was taken up in acetonitrile/water and freeze dried. The residue thus obtained was chromatographed on silica gel using ethyl acetate/heptane (1/3 and 1/1). After concentrating the product fractions, the residue was taken up in acetonitrile/water and freeze dried. For the cleavage of the tert-butyl ester, 10 ml of 95% strength trifluoroacetic acid were added and the mixture was allowed to stand at room temperature for 15 minutes. After removal of the volatile components in vacuo, the residue was taken up in acetonitrile/water and freeze dried. Yield: 463 mg (79%).

ES(+)-MS: 592.4 (M+H)$^+$.

Example 4

(R)-3-((S)-2-(4,4-Pentamethylene-3-(4-(3-phenylureido)benzyl)-2,5-dioxoimidazolidin-1-yl)-2-(2-methylpropyl)acetylamino)-3-(2-methylpropyl)propionic acid

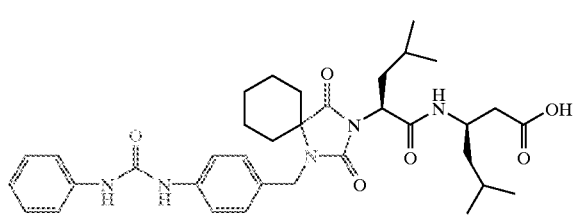

132 mg (0.988 mmol) of HOBT and 245 mg (1.18 mmol) of DCC were added with ice cooling to a solution of 500 mg (0.988 mmol) of (S)-2-(4,4-pentamethylene-3-(4-(3-phenylureido)benzyl)-2,5-dioxoimidazolidin-1-yl)-2-(2-methylpropyl)acetic acid in 15 ml of absolute DMF. After stirring with ice cooling for 1 hour, 199 mg (0.988 mmol) of tert-butyl (R)-3-amino-5-methylhexanoate were added. After stirring at room temperature for 3 hours and allowing to stand overnight, the reaction mixture was filtered and the filtrate was concentrated in vacuo. The residue was taken up in ethyl acetate and washed twice in each case with an aqueous $KHSO_4/K_2SO_4$ solution and water. After drying the organic phase over sodium sulfate and filtering, the solvent was removed in vacuo. The residue was chromatographed on silica gel using ethyl acetate/heptane (1/3 and 1/1). After concentrating the product fractions, the residue was taken up in acetonitrile/water and freeze dried. For the cleavage of the tert-butyl ester, 10 ml of 95% strength trifluoroacetic acid were added and the mixture was stirred at room temperature for 30 minutes. After removal of the volatile components in vacuo, the residue was taken up in acetonitrile/water and freeze dried. Yield: 447 mg (71%).

ES(+)-MS: 634.4 (M+H)$^+$.

Analogously to Examples 1, 3 and 4, the compounds of Examples 5, 6 and 7 can be prepared starting from 1-aminocyclopentane-1-carboxylic acid.

Example 5

(S)-3-((S)-2-(4,4-Tetramethylene-3-(4-(3-phenylureido)benzyl)-2,5-dioxoimidazolidin-1-yl)-2-(2-methylpropyl)acetylamino)-3-phenylpropionic acid

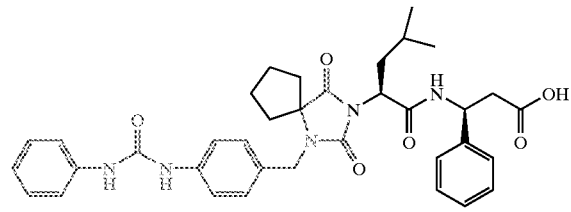

Example 6

(R)-3-((S)-2-(4,4-Tetramethylene-3-(4-(3-phenylureido)benzyl )-2, 5-dioxoimidazolidin-1-yl)-2-(2-methylpropyl)acetylamino)-3-methylpropionic acid

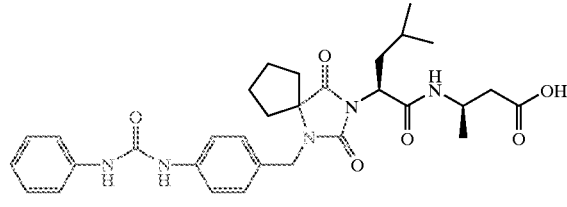

Example 7

(R)-3-((S)-2-(4,4-Tetramethylene-3-(4-(3-phenylureido)benzyl)-2,5-dioxoimidazolidin-1-yl)-2-(2-methylpropyl)acetylamino)-3-(2-methylpropyl)propionic acid

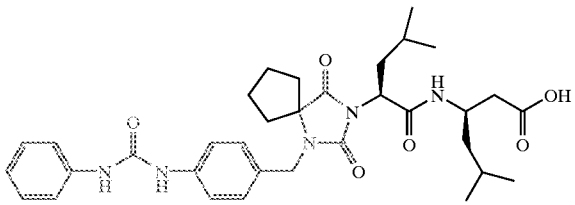

Example 8

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-phenylpropionic acid

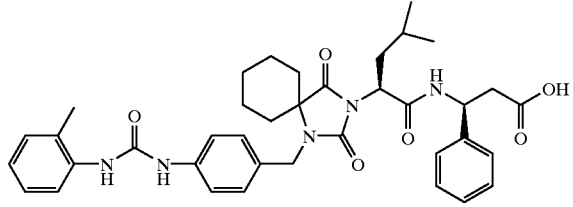

a) 4-(3-(2-Methylphenyl)ureido)benzyl alcohol 30.6 g (200 mmol) of 4-nitrobenzyl alcohol were hydrogenated with ice cooling over 1.0 g of palladium/carbon (10% strength; 50% water) in 500 ml of methyl tert-butyl ether. After the absorption of hydrogen was complete, the catalyst was filtered off and 24.8 ml (200 mmol) of 2-methylphenyl isocyanate were added to the filtrate at 15° C. with stirring in the course of 30 minutes. The precipitated solid was filtered off with suction and washed with methyl tert-butyl ether. Yield: 46.9 g (92%).

b) 4-(3-(2-Methylphenyl)ureido)benzyl chloride 5.66 ml (78.12 mmol) of thionyl chloride were added dropwise with ice cooling to a suspension of 10 g (39.06 mmol) of 4-(3-(2-methylphenyl)ureido)benzyl alcohol in 150 ml of dichloromethane. The reaction mixture was subsequently stirred at room temperature for 1.5 hours and poured onto 200 ml of n-heptane. The heptane was decanted off from the deposited oil and the oil was stirred with diisopropyl ether. The solid obtained was filtered off and washed with diisopropyl ether. Yield: 8.32 g (78%).

c) (S)-2-(4,4-Pentamethylene-3-(4-(3-(2-methylphenyl)ureido)benzyl)-2,5-dioxoimidazolidin-1-yl)-2-(2-methylpropyl)acetic acid 26.6 ml of an n-butyllithium solution (2.5 M in hexane) were added at −76° C. under argon to a solution of 9.5 g (33.6 mmol) of (S)-2-(4,4-pentamethylene-2,5-dioxoimidazolidin-1-yl)-2-(2-methylpropyl)acetic acid in 190 ml of absolute THF. After stirring at −76° C. for 30 minutes, the reaction mixture was allowed to warm to 0° C. and a solution of 9 g (33.6 mmol) of 4-(3-(2-methylphenyl)ureido)benzyl chloride in 95 ml of NMP was added. After stirring at room temperature for 60 minutes, 38 ml of 2 N hydrochloric acid were added and the THF was removed in vacuo. After addition of dichloromethane, the mixture was adjusted to pH 1 using 1 N hydrochloric acid. The phases were separated and the aqueous phase was extracted with dichloromethane. The combined organic phases were dried over sodium sulfate and, after filtration, concentrated in vacuo. The residue was poured into ice water and the precipitate was filtered off with suction. After chromatography on silica gel using dichloromethane/methanol/acetic acid/water (95/5/0.5/0.5), concentration of the product fractions and subsequent freeze drying, 5.05 g (29%) of the title compound were obtained.

d) Ethyl (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-phenylpropionate 566 mg (4.26 mmol) of HOBT and 1.05 g (5.11 mmol) of DCC were added with ice cooling to a solution of 2.22 g (4.26 mmol) of (S)-2-(4,4-pentamethylene-3-(4-(3-(2-methylphenyl)ureido)benzyl)-2,5-dioxoimidazolidin-1-yl)-2-(2-methylpropyl)acetic acid in 30 ml of absolute DMF. After stirring at 0° C. for 1 hour, 823 mg (4.26 mmol) of ethyl 3-amino-3-phenylpropionate (prepared from the hydrochloride) were added. After stirring at room temperature for 4 hours, the reaction mixture was allowed to stand overnight. The urea was filtered off with suction and the filtrate was concentrated in vacuo. The residue was dissolved in ethyl acetate and the ethyl acetate solution was successively washed twice in each case with an aqueous KHSO$_4$/K$_2$SO$_4$ solution, a saturated NaHCO$_3$ solution and water. After drying the organic phase over sodium sulfate and filtering, the solvent was removed in vacuo and the residue was chromatographed on silica gel using ethyl acetate/heptane (1/3 and 1/1). After concentrating the product fractions, 1.98 g (67%) of the title compound were obtained.

e) (S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-phenylpropionic acid 8.5 ml of a 1 M lithium hydroxide solution were added to 1.97 g (2.83 mmol) of ethyl (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-phenylpropionate in 120 ml of methanol and the mixture was allowed to stand at room temperature for 3 days. The methanol was removed in vacuo, and the residual aqueous phase was adjusted to pH 1 by addition of 1 N hydrochloric acid and extracted twice with ethyl acetate. The organic phase was washed with water and dried over sodium sulfate. After filtration, the solvent was removed in vacuo, and the residue was taken up in acetonitrile/water and freeze dried. Yield: 1.69 g (89%).

ES(+)-MS: 668.4 (M+H)$^+$.

Example 9

(R)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-methylpropionic acid

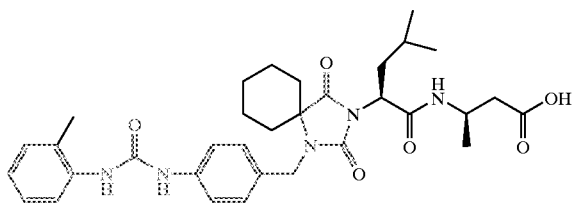

The compound can be prepared by coupling of (S)-2-(4,4-pentamethylene-3-(4-(3-(2-methylphenyl)ureido)benzyl)-2,5-dioxoimidazolidin-1-yl)-2-(2-methylpropyl)acetic acid with tert-butyl (R)-3-aminobutanoate analogously to Example 3.

Example 10

(R)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(2-methylpropyl)propionic acid

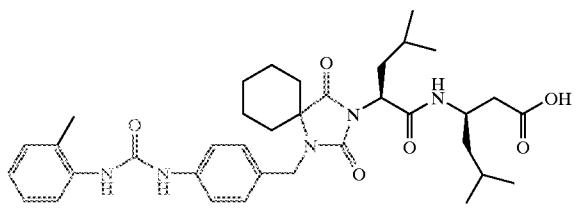

The compound can be prepared by coupling of (S)-2-(4,4-pentamethylene-3-(4-(3-(2-methylphenyl)ureido)benzyl)-2,5-dioxoimidazolidin-1-yl)-2-(2-methylpropyl)acetic acid with tert-butyl (R)-3-amino-5-methylhexanoate analogously to Example 4.

Analogously to Examples 8, 9 and 10, the compounds of Examples 11, 12 and 13 can be prepared starting from 1-aminocyclopentane-1-carboxylic acid.

Example 11

(S)-3-((S)-2-(4,4-Tetramethylene-3-(4-(3-(2-methylphenyl)ureido)benzyl)-2,5-dioxoimidazolidin-1-yl)-2-(2-methylpropyl)acetylamino)-3-phenylpropionic acid

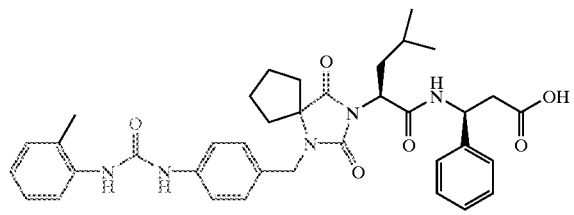

Example 12

(R)-3-((S)-2-(4,4-Tetramethylene-3-(4-(3-(2-methylphenyl)ureido)benzyl)-2,5-dioxoimidazolidin-1-yl)-2-(2-methylpropyl)acetylamino)-3-methylpropionic acid

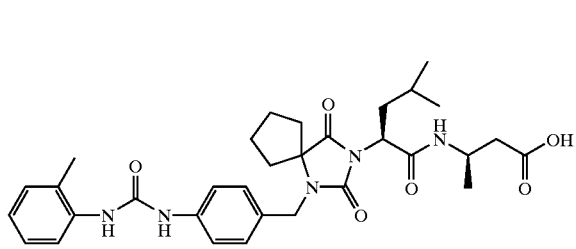

Example 13

(R)-3-((S)-2-(4,4-Tetramethylene-3-(4-(3-(2-methylphenyl)ureido)benzyl)-2,5-dioxoimidazolidin-1-yl)-2-(2-methylpropyl)acetylamino)-3-(2-methylpropyl)propionic acid

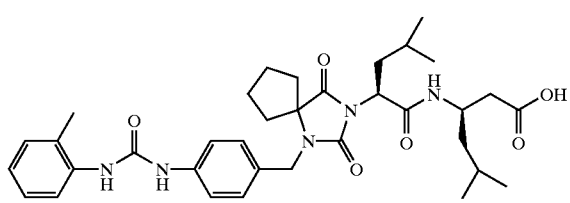

Example 14

(R)-3-((S)-2-(4,4-Pentamethylene-3-(4-(3-phenylureido)benzyl)-2,5-dioxoimidazolidin-1-yl)-2-(2-methylpropyl)acetylamino)-3-methylpropionamide

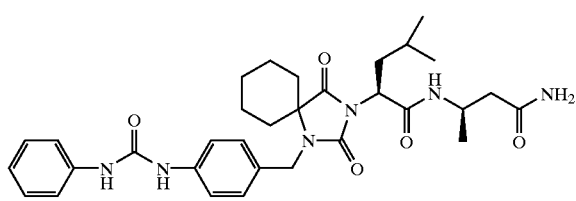

The compound was prepared from 1.012 g (2 mmol) of (S)-2-(4,4-pentamethylene-3-(4-(3-phenylureido)benzyl)-2,5-dioxoimidazolidin-1-yl)-2-(2-methylpropyl)acetic acid and 204 mg (2 mmol) of (R)-3-aminobutanamide as described in Example 1. After chromatographic purification of the coupling product, 392 mg (33%) of the title compound were obtained.

ES(+)-MS: 591.4 (M+H)+.

Example 15

(S)-3-((S)-2-(4,4-Pentamethylene-3-(4-(3-phenylureido)benzyl)-2,5-dioxoimidazolidin-1-yl)-2-(2-methylpropyl)acetylamino)-3-phenylpropionamide

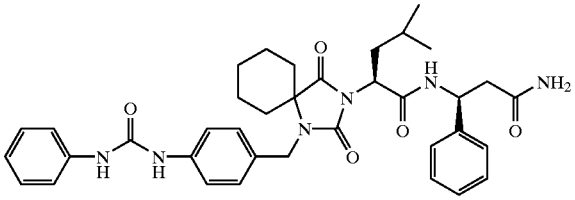

271 mg (2.04 mmol) of HOBT and 290 mg (1.4 mmol) of DCC were added with ice cooling to a solution of 800 mg (1.22 mmol) of (S)-3-((S)-2-(4,4-pentamethylene-3-(4-(3-phenylureido)benzyl)-2,5-dioxoimidazolidin-1-yl)-2-(2-methylpropyl)acetylamino)-3-phenylpropionic acid (see Example 1) in 10 ml of DMF. After stirring at room temperature for 1 h, 101 μl of a 25% strength aqueous ammonia solution were added and the mixture was allowed to stand overnight at room temperature. After filtration, the filtrate was concentrated in vacuo, the residue was dissolved in dichloromethane and the organic phase was washed twice using an aqueous $KHSO_4/K_2SO_4$ solution, twice using saturated $NaHCO_3$ solution and twice with water. After drying the organic phase over magnesium sulfate, filtration, removal of the solvent in vacuo and chromatographic purification of the residue on silica gel (eluent: ethyl acetate/heptane, 9/1), 543 mg (68%) of the title compound were obtained.

ES(+)-MS: 653.4 (M+H)+.

Example 16

(S)-3-((S)-2-(4,4-Pentamethylene-3-(4-(3-phenylureido)benzyl)-2,5-dioxoimidazolidin-1-yl)-2-(2-methylpropyl)acetylamino)-3-(4-methoxyphenyl)propionic acid

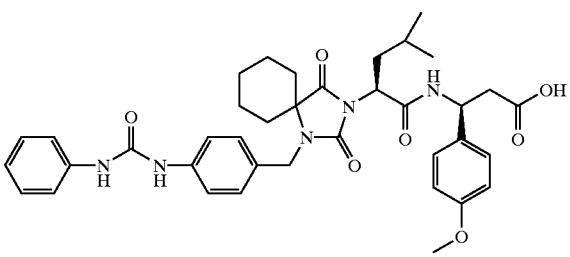

The compound was prepared analogously to Example 1 from 2.02 g (3.98 mmol) of (S)-2-(4,4-pentamethylene-3-(4-(3-phenylureido)benzyl)-2,5-dioxoimidazolidin-1-yl)-2-(2-methyl propyl)acetic acid and 1 g (3.98 mmol) of tert-butyl (S)-3-amino-3-(4-methoxyphenyl)propionate (for the preparation of this β-amino acid ester and of the other β-amino acid esters employed in the preparation of the example compounds see S. G. Davies et al., Tetrahedron: Asymmetry 2, 183 (1991) and J. Chem. Soc. Perkin Trans 1, 1129 (1994)). After coupling, chromatographic purification of the coupling product, cleavage of the tert-butyl ester and subsequent chromatographic purification, 1.116 g (41%) of the title compound were obtained.

ES(+)-MS: 684.4 (M+H)+.

Example 17

(S)-3-((S)-2-(4,4-Pentamethylene-3-(4-(3-phenylureido)benzyl)-2,5-dioxoimidazolidin-1-yl)-2-(2-methylpropyl)acetylamino)-3-(4-methoxyphenyl) propionic acid tromethamine salt

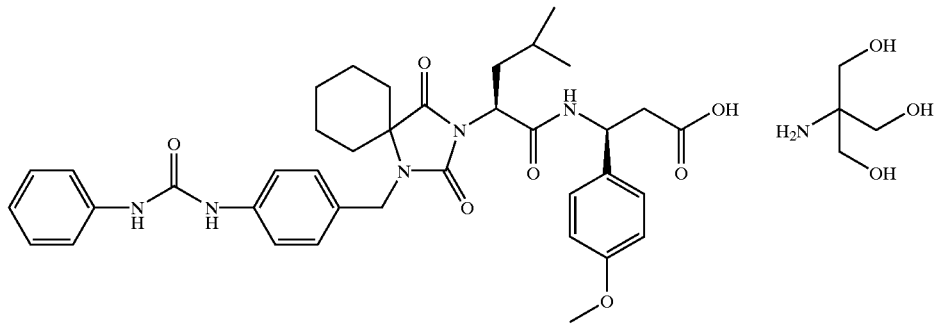

The compound was prepared analogously to Example 2. Starting from 550 mg of (S)-3-((S)-2-(4,4-pentamethylene-3-(4-(3-phenylureido)benzyl)-2,5-dioxoimidazolidin-1-yl)-2-(2-methylpropyl)acetylamino)-3-(4-methoxyphenyl) propionic acid, 632 mg of the corresponding tromethamine salt were obtained (stoichiometry: (S)-3-((S)-2-(4,4-pentamethylene-3-(4-(3-phenylureido)benzyl)-2,5-dioxoimidazolidin-1-yl)-2-(2-methylpropyl)acetylamino)-3-(4-methoxyphenyl)propionic acid/tromethamine about 1/1.5).

ES(+)-MS: 122.0 ($\alpha,\alpha,\alpha$-tris(hydroxymethyl)methylamine+H)$^+$, 684.5 (S)-3-((S)-2-(4,4-pentamethylene-3-(4-(3-phenylureido)benzyl)-2,5-dioxoimidazolidin-1-yl)-2-(2-methylpropyl)acetylamino)-3-(4-methoxyphenyl) propionic acid+H)$^+$, 805.5 (M+H)$^+$.

Example 18

(S)-3-((S)-2-(4,4-Pentamethylene-3-(4-(3-phenylureido)benzyl)-2,5-dioxoimidazolidin-1-yl)-2-(2-methylpropyl)acetylamino)-3-(2,4-dimethoxyphenyl)propionic acid

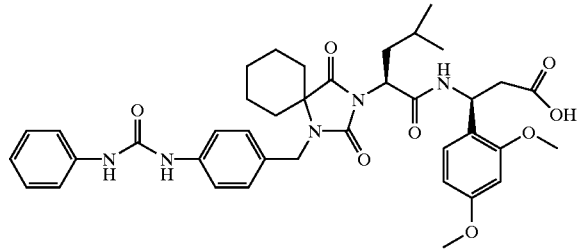

The compound was prepared analogously to Example 1 from 1.08 g (2.14 mmol) of (S)-2-(4,4-pentamethylene-3-(4-(3-phenylureido)benzyl)-2,5-dioxoimidazolidin-1-yl)-2-(2-methylpropyl)acetic acid and 600 mg (2.14 mmol) of tert-butyl (S)-3-amino-3-(2,4-dimethoxyphenyl)propionate. After coupling, chromatographic purification of the coupling product, cleavage of the tert-butyl ester and subsequent chromatographic purification, 341 mg (22%) of the title compound were obtained.
ES(+)-MS: 714.4 (M+H)$^+$.

Example 19

(S)-3-((S)-2-(4,4-Pentamethylene-3-(4-(3-phenylureido)benzyl)-2,5-dioxoimidazolidin-1-yl)-2-(2-methylpropyl)acetylamino)-3-(2,4-dimethoxyphenyl)propionic acid tromethamine salt

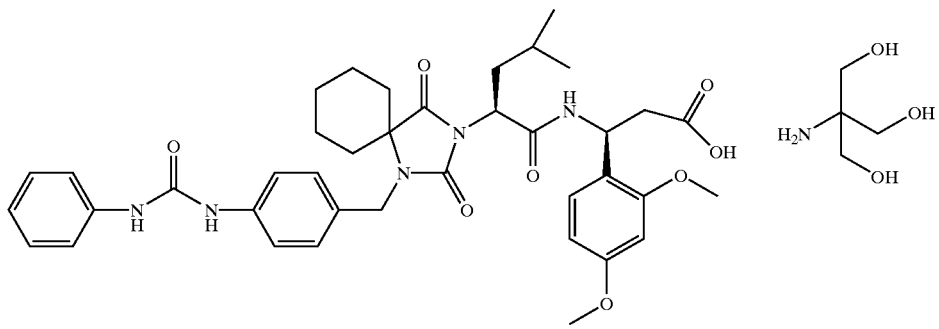

The compound was prepared analogously to Example 2. Starting from 160 mg of (S)-3-((S)-2-(4,4-pentamethylene-3-(4-(3-phenylureido)benzyl)-2,5-dioxoimidazolidin- 1-yl)-2-(2-methylpropyl)acetylamino)-3-(2,4-dimethoxyphenyl) propionic acid, 188 mg of the corresponding tromethamine salt were obtained (stoichiometry: (S)-3-((S)-2-(4,4-pentamethylene-3-(4-(3-phenylureido)benzyl)-2,5-dioxoimidazolidin-1-yl)-2-(2-methylpropyl)acetylamino)-3-(2,4-dimethoxyphenyl)propionic acid/tromethamine about 1/2.1).

ES(+)-MS: 122.0 (α,α,α-tris(hydroxymethyl)methylamine+H)$^+$, 714.4 (S)-3-((S)-2-(4,4-pentamethylene-3-(4-(3-phenylureido)benzyl)-2,5-dioxoimidazolidin-1-yl)-2-(2-methylpropyl)acetylamino)-3-(2,4-dimethoxyphenyl) propionic acid+H)$^+$, 835.5 (M+H)$^+$.

Example 20

(S)-3-((S)-2-(4,4-Pentamethylene-3-(4-(3-phenylureido)benzyl)-2,5-dioxoimidazolidin-1-yl)-2-(2-methylpropyl)acetylamino)-3-(3,4-dimethoxyphenyl)propionic acid

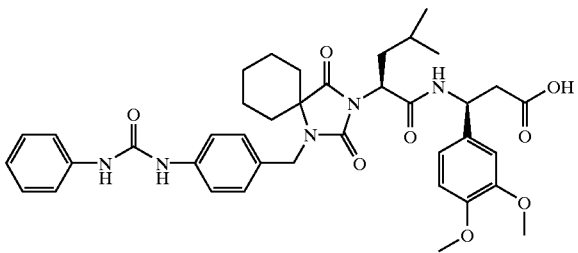

The compound was prepared analogously to Example 1 from 1.5 g (2.96 mmol) of (S)-2-(4,4-pentamethylene-3-(4-(3-phenylureido)benzyl)-2,5-dioxoimidazolidin-1-yl)-2-(2-methylpropyl)acetic acid and 833 mg (2.96 mmol) of tert-butyl (S)-3-amino-3-(3,4-dimethoxyphenyl)propionate. After coupling, chromatographic purification of the coupling product, cleavage of the tert-butyl ester and trituration with water and then pentane, 1.17 g (55%) of the title compound were obtained.

ES(+)-MS: 714.4 (M+H)$^+$.

Example 21

(S)-3-((S)-2-(4,4-Pentamethylene-3-(4-(3-phenylureido)benzyl)-2,5-dioxoimidazolidin-1-yl)-2-(2-methylpropyl)acetylamino)-3-(3,4-dimethoxyphenyl)propionic acid tromethamine salt

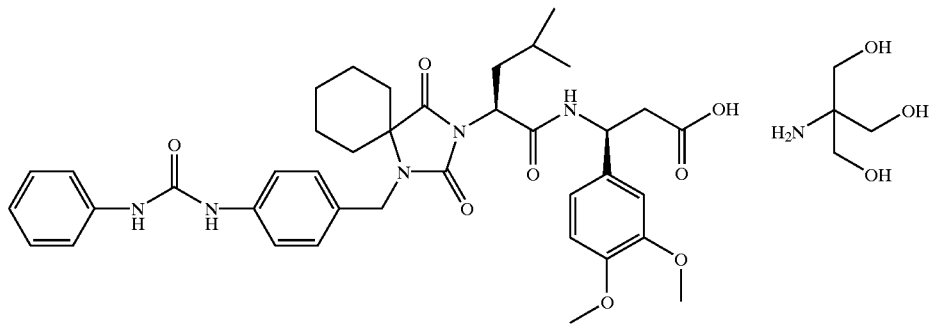

The compound was prepared analogously to Example 2. Starting from 200 mg of (S)-3-((S)-2-(4,4-pentamethylene-3-(4-(3-phenylureido)benzyl)-2,5-dioxoimidazolidin-1-yl)-2-(2-methylpropyl)acetylamino)-3-(3,4-dimethoxyphenyl) propionic acid, 235 mg of the corresponding tromethamine salt were obtained (stoichiometry: (S)-3-((S)-2-(4,4-pentamethylene-3-(4-(3-phenylureido)benzyl)-2,5-dioxoimidazolidin-1-yl)-2-(2-methylpropyl)acetylamino)-3-(3,4-dimethoxyphenyl)propionic acid/tromethamine about 1/1.4).

ES(+)-MS: 122.0 (α,α,α-tris(hydroxymethyl)methylamine+H)$^+$, 714.4 (S)-3-((S)-2-(4,4-pentamethylene-3-(4-(3-phenylureido)benzyl)-2,5-dioxoimidazolidin-1-yl)-2-(2-methylpropyl)acetylamino)-3-(3,4-dimethoxyphenyl) propionic acid+H)$^+$, 835.4 (M+H)$^+$.

Example 22

(S)-3-((S)-2-(4,4-Pentamethylene-3-(4-(3-phenylureido)benzyl)-2,5-dioxoimidazolidin-1-yl)-2-(2-methylpropyl)acetylamino)-3-(3-methoxyphenyl)propionic acid

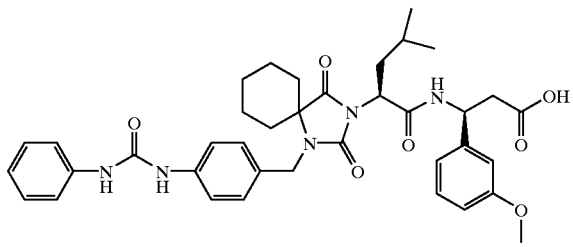

The compound was prepared analogously to Example 1 from 1.5 g (2.96 mmol) of (S)-2-(4,4-pentamethylene-3-(4-(3-phenylureido)benzyl)-2,5-dioxoimidazolidin-1-yl)-2-(2-methylpropyl)acetic acid and 1.48 g (2.96 mmol) of tert-butyl (S)-3-amino-3-(3-methoxyphenyl)propionate. After coupling, chromatographic purification of the coupling product, cleavage of the tert-butyl ester and trituration with water and then pentane, 1.01 g (50%) of the title compound were obtained.

ES(+)-MS: 684.4 (M+H)$^+$.

Example 23

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-phenylpropionic acid tromethamine salt

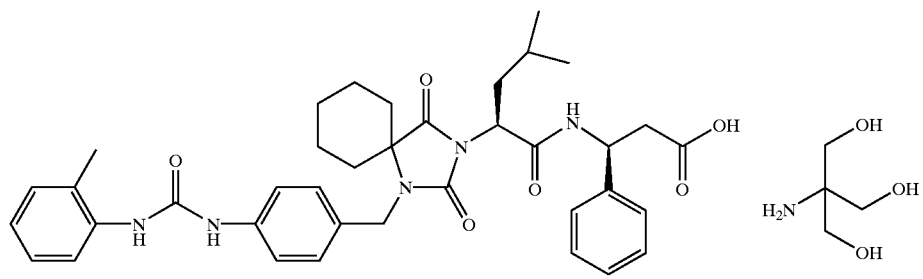

The compound was prepared analogously to Example 2. Starting from 216 mg of (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-phenylpropionic acid (see Example 8), 235 mg of the corresponding tromethamine salt were obtained (stoichiometry: (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-phenylpropionic acid/tromethamine about 1/1.5).

ES(+)-MS: 122.0 ($\alpha,\alpha,\alpha$-tris(hydroxymethyl)methylamine+H)$^+$, 668.4 ((S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-phenylpropionic acid+H)$^+$, 789.5 (M+H)$^+$.

Example 24

(R)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-methylpropionic acid tromethamine salt

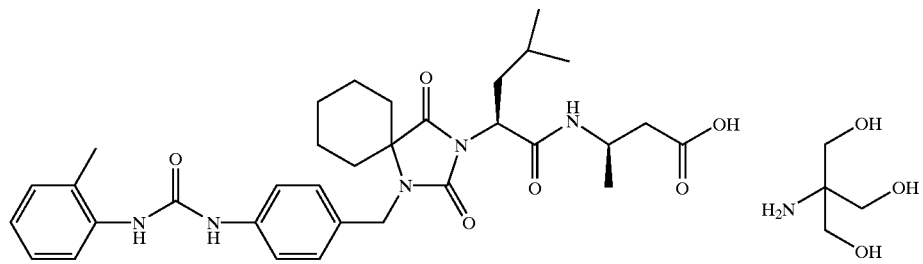

The compound was prepared analogously to Example 2. Starting from 250 mg of (R)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-methylpropionic acid (see Example 9), 315 mg of the corresponding tromethamine salt were obtained (stoichiometry: (R)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-methylpropionic acid/tromethamine about 1/1.3).

ES(+)-MS: 122.0 (α,α,α-tris(hydroxymethyl) methylamine+H)$^+$, 606.4 ((R)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-methylpropionic acid+H)$^+$, 727.5 (M+H)$^+$.

Example 25

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(3-methoxyphenyl)propionic acid

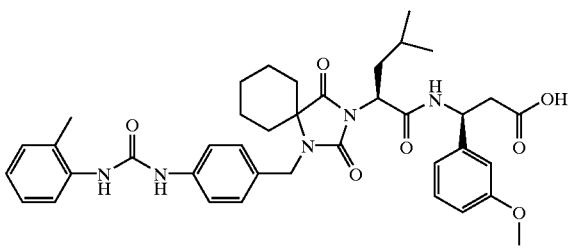

The compound was prepared analogously to Example 1 from 1 g (1.92 mmol) of (S)-2-(4,4-pentamethylene-3-(4-(3-(2-methylphenyl)ureido)benzyl)-2,5-dioxoimidazolidin-1-yl)-2-(2-methylpropyl)acetic acid (see Example 8) and 963 mg (3.84 mmol) of tert-butyl (S)-3-amino-3-(3-methoxyphenyl)propionate. After coupling, chromatographic purification of the coupling product, cleavage of the tert-butyl ester and trituration with water and then pentane, 555 mg (40%) of the title compound were obtained.

ES(+)-MS: 698.4 (M+H)$^+$.

Example 26

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(4-methoxyphenyl)propionic acid

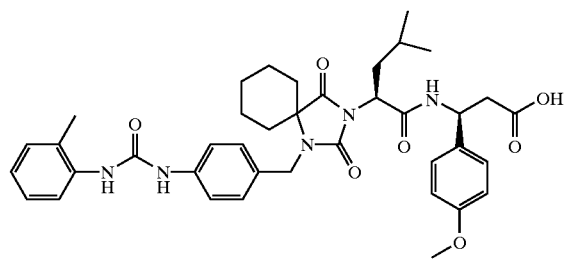

The compound was prepared analogously to Example 1 from 900 mg (1.73 mmol) of (S)-2-(4,4-pentamethylene-3-(4-(3-(2-methylphenyl)ureido)benzyl)-2,5-dioxoimidazolidin-1-yl)-2-(2-methylpropyl)acetic acid (see Example 8) and 434 mg (1.73 mmol) of tert-butyl (S)-3-amino-3-(4-methoxyphenyl)propionate. After coupling, chromatographic purification of the coupling product, cleavage of the tert-butyl ester and trituration with water and pentane, 348 mg (29%) of the title compound were obtained.

ES(+)-MS: 698.4 (M+H)$^+$.

Example 27

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(4-methoxyphenyl)propionic acid tromethamine salt

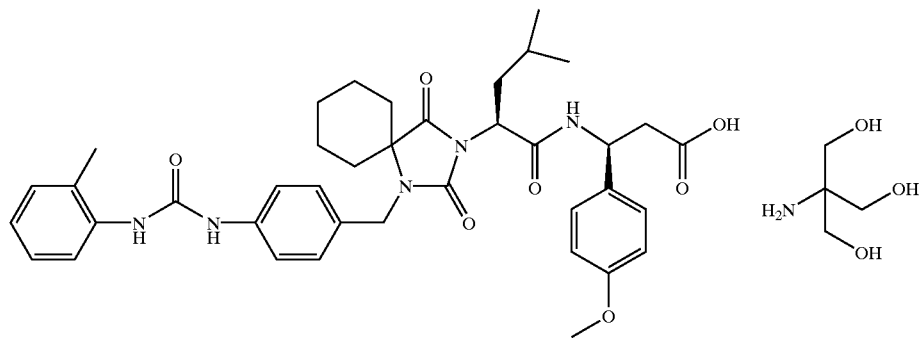

The compound was prepared analogously to Example 2. Starting from 170 mg of (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(4-methoxyphenyl)propionic acid (see Example 26), 173 mg of the corresponding tromethamine salt were obtained (stoichiometry: (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(4-methoxyphenyl)propionic acid/tromethamine about 1/1.6).

ES(+)-MS: 122.0 (α,α,α-tris(hydroxymethyl)methylamine+H)⁺, 698.4 ((S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(4-methoxyphenyl)propionic acid+H)⁺, 819.5 (M+H)⁺.

Example 28

(S)-3-((S)-2-(4,4-Pentamethylene-3-(4-(3-(2-methyphenyl)ureido)benzyl)-2,5-dioxoimidazolidin-1-yl)-2-(2-methylpropyl)acetylamino)-3-(2,4-dimethoxyphenyl)propionic acid

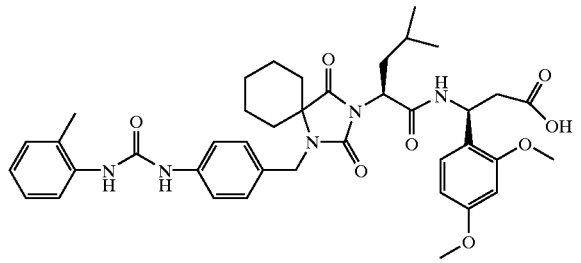

The compound was prepared analogously to Example 1 from 900 mg (1.73 mmol) of (S)-2-(4,4-pentamethylene-3-(4-(3-(2-methylphenyl)ureido)benzyl-2,5-dioxoimidazolidin-1-yl)-2-(2-methylpropyl)acetic acid (see Example 8) and 486 mg (1.73 mmol) of tert-butyl (S)-3-amino-3-(2,4-dimethoxyphenyl)propionic acid. After coupling, chromatographic purification of the coupling product, cleavage of the tert-butyl ester and trituration with water and pentane, 330 mg (26%) of the title compound were obtained.

ES(+)-MS: 728.4 (M+H)⁺.

Example 29

(S)-3-((S)-2-(4,4-Pentamethylene-3-(4-(3-(2-methylphenyl)ureido)benzyl-2,5-dioxoimidazolidin-1-yl)-2-(2-methylpropyl)acetylamino)-3-(2,4-dimethoxyphenyl)propionic acid tromethamine salt

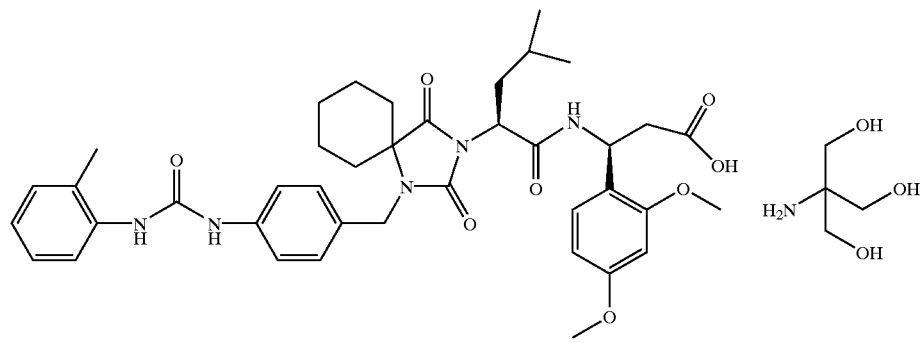

The compound was prepared analogously to Example 2. Starting from 160 mg of (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(2,4-dimethoxyphenyl)propionic acid (see Example 28), 82 mg of the corresponding tromethamine salt were obtained (stoichiometry: (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(2,4-dimethoxyphenyl)propionic acid/tromethamine about 1/4.2).

ES(+)-MS: 122.0 (α,α,α-tris(hydroxymethyl)methylamine+H)⁺, 728.5 ((S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(2,4-dimethoxyphenyl)propionic acid+H)⁺, 849.5 (M+H)⁺.

Example 30

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(2,4-dimethoxyphenyl)propionic acid sodium salt

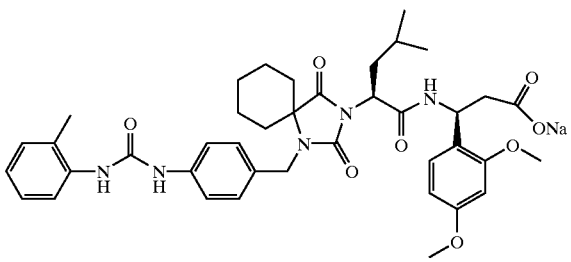

1 mole equivalent of 1 N sodium hydroxide solution was added to a solution of 292 mg of (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(2,4-dimethoxyphenyl)propionic acid (see Example 28) in THF. After stirring for 30 minutes, the THF was removed in vacuo and the solution was diluted with water and freeze dried. After purification on Sephadex using water, 216 mg of the title compound were obtained.

ES(+)-MS: 728.3 ((S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(2,4-dimethoxyphenyl)propionic acid+H)$^+$, 750.3 (M+H)$^+$.

Example 31

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid

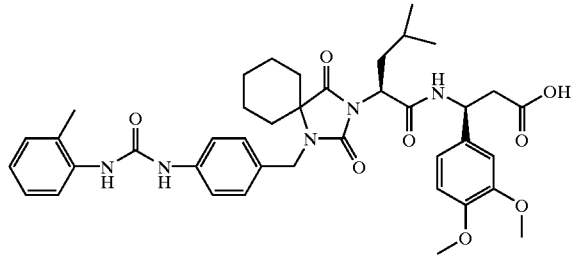

The compound was prepared analogously to Example 1 from 1 g (1.92 mmol) of (S)-2-(4,4-pentamethylene-3-(4-(3-(2-methylphenyl)ureido)benzyl)-2,5-dioxoimidazolidin-1-yl)-2-(2-methylpropyl)acetic acid (see Example 8) and 540 mg (1.92 mmol) of tert-butyl (S)-3-amino-3-(3,4-dimethoxyphenyl)propionate. After coupling, chromatographic purification of the coupling product, cleavage of the tert-butyl ester, chromatographic purification by means of preparative HPLC, concentration of the product fractions, freeze drying and trituration of the product with water and pentane, 480 mg (34%) of the title compound were obtained.

ES(+)-MS: 728.4 (M+H)$^+$.

Example 32

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid tromethamine salt

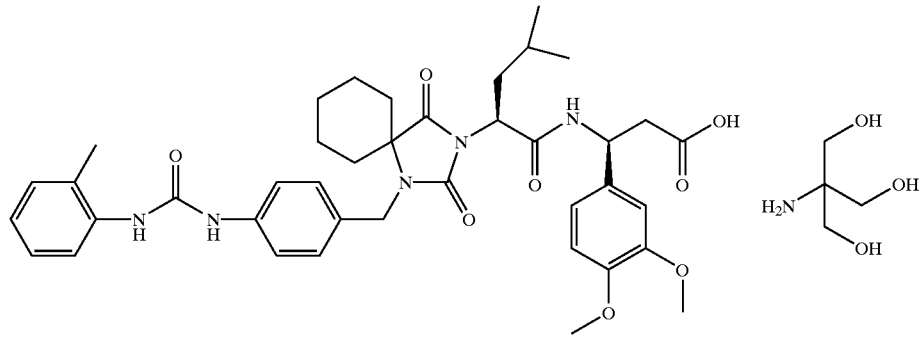

The compound was prepared analogously to Example 2. Starting from 150 mg of (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid (see Example 31), 175 mg of the corresponding tromethamine salt were obtained (stoichiometry: (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid/tromethamine about 1/1.3).

ES(+)-MS: 122.0 ($\alpha,\alpha,\alpha$-tris(hydroxymethyl)methylamine+H)$^+$, 728.5 ((S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid+H)$^+$, 849.6 (M+H)$^+$.

Example 33

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid sodium salt

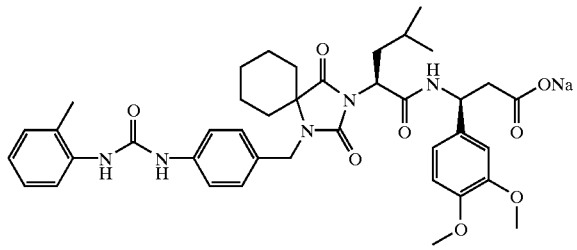

1 mole equivalent of 1 N sodium hydroxide solution was added to a solution of 300 mg of (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid (see Example 31) in THF. After stirring for 30 minutes, the THF was removed in vacuo and the solution was diluted with water and freeze dried. After purification on Sephadex using water, 154 mg of the title compound were obtained.

ES(+)-MS: 728.3 ((S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid+H)$^+$, 750.3 (M+H)$^+$.

Example 34

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(3,4-ethylenedioxyphenyl)propionic acid

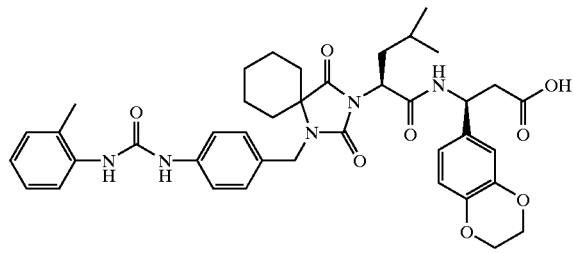

The compound was prepared analogously to Example 1 from 590 mg (1.1 mmol) of ((S)-2-(4,4-pentamethylene-3-(4-(3-(2-methyl phenyl)ureido)benzyl-2,5-dioxoimidazolidin-1-yl)-2-(2-methylpropyl)acetic acid (see Example 8) and 475 mg (1.7 mmol) of tert-butyl (S)-3-amino-3-(3,4-ethylenedioxyphenyl)propionate. After coupling, chromatographic purification of the coupling product and cleavage of the tert-butyl ester, 650 mg (81%) of the title compound were obtained.

ES(+)-MS: 726.2 (M+H)$^+$.

Example 35

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(3,4-ethylenedioxyphenyl)propionic acid sodium salt

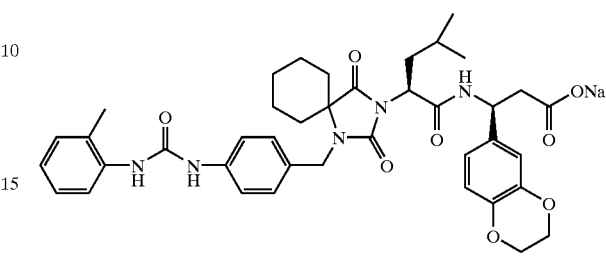

0.95 mole equivalent of 1 N sodium hydroxide solution was added to a suspension of 600 mg (0.83 mmol) of (S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(3,4-ethylenedioxyphenyl)propionic acid (see Example 34) in water. After stirring for 30 minutes, the mixture was filtered and the filtrate was freeze dried. 610 mg (98%) of the title compound were obtained.

ES(+)-MS: 726.2 ((S)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-(3,4-ethylenedioxyphenyl)propionic acid+H)$^+$, 748.2 (M+H)$^+$.

Example 36

(R)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-methylpropionamide

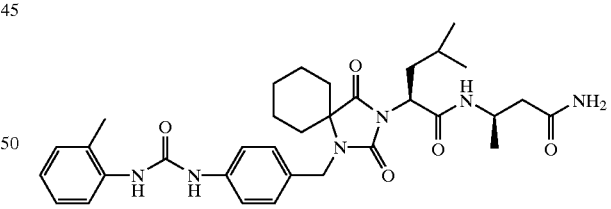

The compound was prepared analogously to Example 15. Starting from 150 mg (0.247 mmol) of (R)-3-((S)-2-(4,4-pentamethylene-3-(4-(3-(2-methylphenyl)ureido)benzyl)-2,5-dioxoimidazolidin-1-yl)-2-(2-methylpropyl)acetylamino)-3-methylpropionic acid (see Example 9), after chromatographic purification of the crude product on silica gel using ethyl acetate as eluent, concentration of the product fractions, trituration of the residue with water and then pentane and freeze drying, 74 mg (50%) of the title compound were obtained.

ES(+)-MS: 605.4 (M+H)$^+$.

Example 37

(S)-3-((S)-2-(4,4-Pentamethylene-3-(4-(3-(2-methylphenyl)ureido)-3-methoxybenzyl)-2,5-dioxoimidazolidin-1-yl)-2-(2-methylpropyl)acetylamino)-3-(3,4-dimethoxyphenyl)propionic acid

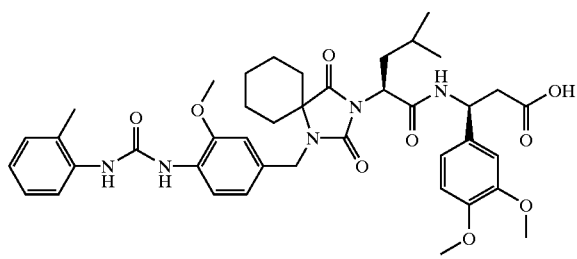

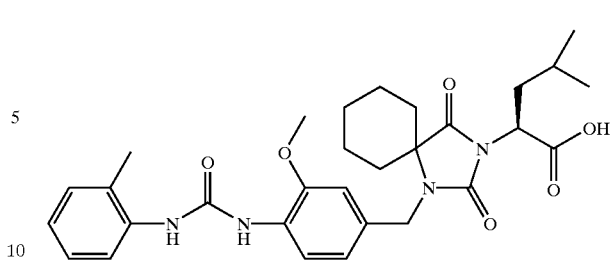

a) 4-(3-(2-Methylphenyl)ureido)-3-methoxybenzyl alcohol 15 g (81.8 mmol) of 3-methoxy-4-nitrobenzyl alcohol were hydrogenated with ice cooling on 1.3 g of palladium/carbon (10% strength; 50% water) in 500 ml of methyl tert-butyl ether. After the absorption of hydrogen was complete, the catalyst was filtered off and 10.14 ml (81.8 mmol) of 2-methylphenyl isocyanate were added to the filtrate with stirring in the course of 30 minutes. The reaction mixture was allowed to stand overnight, and the precipitated solid was filtered off with suction and washed with methyl tert-butyl ether. 20.5 g (88%) of 4-(3-(2-methylphenyl)ureido)-3-methoxybenzyl alcohol were obtained.

b) 4-(3-(2-Methylphenyl)ureido)-3-methoxybenzyl chloride 7.65 ml (104.8 mmol) of thionyl chloride were added dropwise with ice cooling to a suspension of 15 g (52.4 mmol) of 4-(3-(2-methylphenyl)ureido)-3-methoxybenzyl alcohol in 300 ml of dichloromethane. The reaction mixture was subsequently stirred at room temperature for 3 hours, allowed to stand overnight and then poured onto 1000 ml of n-heptane. The heptane was decanted off from the deposited oil, the residue was again suspended with n-heptane and the heptane was decanted off. This process was repeated a further two times. The residue was then dissolved in dichloromethane and poured into 800 ml of ice-cold diisopropyl ether. It was subsequently stirred with ice cooling for 2 hours, and the product was filtered off with suction and washed with diisopropyl ether. After drying over phosphorus pentoxide, 12 g (75%) of the title compound were obtained.

c) (S)-2-(4,4-Pentamethylene-3-(4-(3-(2-methylphenyl)ureido)-3-methoxybenzyl)-2,5-dioxoimidazolidin-1-yl)-2-(2-methylpropyl)acetic acid 6.6 ml of an n-butyllithium solution (2.5 M in hexane) were added at –40° C. under argon to a solution of 1.98 g (8.21 mmol) of (S)-2-(4,4-pentamethylene-2,5-dioxoimidazolidin-1-yl)-2-(2-methylpropyl)acetic acid in 40 ml of absolute THF. After stirring at –40° C. for 30 minutes, the reaction mixture was allowed to warm to 0° C. and a solution of 2.5 g (8.21 mmol) of 4-(3-(2-methylphenyl)ureido)-3-methoxybenzyl chloride in 10 ml of NMP was added. The reaction mixture was allowed to warm to 0° C. and was subsequently stirred at 0° C. for 2 hours. 15 ml of 1 N hydrochloric acid were added and the THF was removed in vacuo. The residue was poured onto 300 ml of methyl tert-butyl ether. The phases were separated, and the organic phase was washed with water, dried over sodium sulfate and, after filtration, concentrated in vacuo. The residue was purified by preparative HPLC. After concentration of the product fractions and subsequent freeze drying, 716 mg (17%) of the title compound were obtained.

d) (S)-3-((S)-2-(4,4-Pentamethylene-3-(4-(3-(2-methylphenyl)ureido)-3-methoxybenzyl)-2,5-dioxoimidazolidin-1-yl)-2-(2-methylpropyl)acetylamino)-3-(3,4-dimethoxyphenyl)propionic acid The compound was prepared analogously to Example 1 from 300 mg (0.55 mmol) of (S)-2-(4,4-pentamethylene-3-(4-(3-(2-methylphenyl)ureido)-3-methoxybenzyl)-2,5-dioxoimidazolidin-1-yl)-2-(2-methylpropyl)acetic acid and 154 mg (0.55 mmol) of tert-butyl (S)-3-amino-3-(3,4-dimethoxyphenyl)propionate. After coupling, chromatographic purification of the coupling product, cleavage of the tert-butyl ester, chromatographic purification by means of preparative HPLC, concentration of the product fractions and freeze drying, 205 mg (49%) of the title compound were obtained.

ES(+)-MS: 758.3 (M+H)$^+$.

Example 38

(S)-3-((S)-2-(4,4-Pentamethylene-3-(4-(3-(2-methylphenyl)ureido)-3-methoxybenzyl)-2,5-dioxoimidazolidin-1-yl)-2-(2-methyl propyl)acetylamino)-3-(3,4-dimethoxyphenyl)propionic acid tromethamine salt

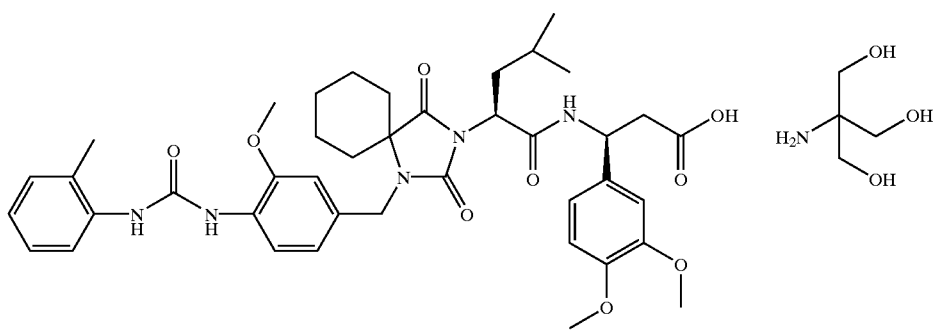

The compound was prepared analogously to Example 2. Starting from 100 mg of (S)-3-((S)-2-(4,4-pentamethylene-3-(4-(3-(2-methylphenyl)ureido)-3-methoxybenzyl)-2,5-dioxoimidazolidin-1-yl)-2-(2-methylpropyl)acetylamino)-3-(3,4-dimethoxyphenyl)propionic acid (see Example 37), 123 mg of the corresponding tromethamine salt were obtained (stoichiometry: (S)-3-((S)-2-(4,4-pentamethylene-3-(4-(3-(2-methylphenyl)ureido)-3-methoxybenzyl)-2,5-dioxoimidazolidin-1-yl)-2-(2-methylpropyl)acetylamino)-3-(3,4-dimethoxyphenyl)propionic acid/tromethamine about 1/1.3).

ES(+)-MS: 122.0 ($\alpha,\alpha,\alpha$-tris(hydroxymethyl)methylamine+H)$^+$, 758.3 ((S)-3-((S)-2-(4,4-pentamethylene-3-(4-(3-(2-methylphenyl)ureido)-3-methoxybenzyl)-2,5-dioxoimidazolidin-1-yl)-2-(2-methylpropyl)acetylamino)-3-(3,4-dimethoxyphenyl)propionic acid+H)$^+$, 879.4 (M+H)$^+$.

Example 39

(S)-3-((S)-2-(4,4-Pentamethylene-3-(4-(3-(2-methylphenyl)ureido)benzyl)-2,5-dioxoimidazolidin-1-yl)-2-cyclopropylmethylacetylamino)-3-(3,4-dimethoxyphenyl)propionic acid

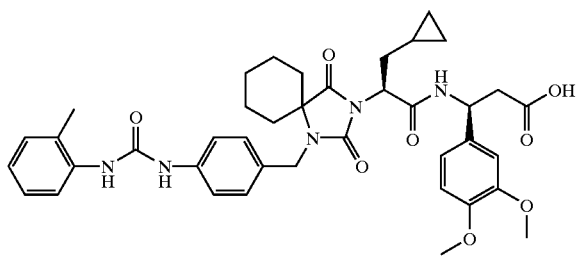

The compound was prepared analogously to Example 1 from 257 mg (0.496 mmol) of (S)-2-(4,4-pentamethylene-3-(4-(3-(2-methylphenyl)ureido)benzyl)-2,5-dioxoimidazolidin-1-yl)-2-cyclopropylmethylacetic acid and 140 mg (0.496 mmol) of tert-butyl (S)-3-amino-3-(3,4-dimethoxyphenyl)propionate. After coupling, chromatographic purification of the coupling product, cleavage of the tert-butyl ester and freeze drying, 296 mg (82%) of the title compound were obtained.

ES(+)-MS: 726.3 (M+H)$^+$.

The (S)-2-(4,4-pentamethylene-3-(4-(3-(2-methylphenyl)ureido)benzyl)-2,5-dioxoimidazolidin-1-yl)-2-cyclopropylmethylacetic acid was prepared analogously to Example 37 from (S)-2-(4,4-pentamethylene-2,5-dioxoimidazolidin-1-yl)-2-cyclopropylmethylacetic acid and 4-(3-(2-methylphenyl)ureido)benzyl chloride (see Example 8).

The (S)-2-(4,4-pentamethylene-2,5-dioxoimidazolidin-1-yl)-2-cyclopropylmethylacetic acid was prepared from (S)-2-amino-3-cyclopropylpropionic acid by the following process.

1 N sodium hydroxide solution was added to a suspension of 10 g (77.5 mmol) of (S)-2-amino-3-cyclopropylpropionic acid in 160 ml of dioxane at 0° C. until a pH of 8 to 9 was reached. 16.9 g (77.5 mmol) of di-tert-butyl dicarbonate were then added, the ice bath was removed and the pH was kept at 8 to 9 by further addition of 1 N sodium hydroxide solution. After allowing to stand overnight, the dioxane was removed in vacuo, ethyl acetate was added to the aqueous phase and the phases were separated. The aqueous phase was adjusted to a pH of 4.5 using 1 N hydrochloric acid and extracted with ethyl acetate. The ethyl acetate phase thus obtained was dried over sodium sulfate, the drying agent was filtered off and the filtrate was concentrated in vacuo. The residue was dissolved in 1000 ml of dichloromethane and treated with 53.4 ml of benzyl alcohol, 8.37 g of 4-dimethylaminopyridine and 18.8 g of DCC. After stirring for 6 hours and standing overnight, the mixture was filtered, the filtrate was concentrated and the residue was treated with 300 ml of 90% strength trifluoroacetic acid. After stirring at room temperature for 10 minutes, the trifluoroacetic acid was removed in vacuo and the residue was chromatographed twice on silica gel (eluent: dichloromethane/methanol, 95/5). 11.48 g (68%) of benzyl (S)-2-amino-3-cyclopropylpropionate were obtained.

A suspension of 39.9 g (279 mmol) of 1-aminocyclohexane-1-carboxylic acid in a mixture of 75 ml of THF and 75 ml of water was treated dropwise with 23.8 ml of methyl chloroformate, dissolved in 40 ml of THF, such that the temperature of the suspension did not rise above 50° C. In the course of this, the pH of the solution was kept between 8.5 and 9.5 by addition of 25% strength sodium hydroxide solution. After stirring at pH 8 for 30 minutes, the mixture was diluted with water, the THF was removed in vacuo and the aqueous phase was washed twice with methyl tert-butyl ether. The aqueous phase was adjusted to pH 2 using 6 N hydrochloric acid and extracted successively with methyl tert-butyl ether and dichloromethane. The combined organic phases were concentrated in vacuo. The residue was triturated with diethyl ether and the product was filtered off. 47.85 g (85%) of 1-methoxycarbonylaminocyclohexane-1-carboxylic acid were obtained.

216 mg of HOBT and 3.2 g (16 mmol) of DCC were added to a solution of 3.2 g (16 mmol) of 1-methoxycarbonylaminocyclohexane-1-carboxylic acid and 3.5 g (16 mmol) of benzyl (S)-2-amino-3-cyclopropylpropionate in 40 ml of THF and the mixture was stirred at room temperature for 1 hour. After allowing to stand overnight and filtering, the THF was removed in vacuo, the residue was taken up in methyl tert-butyl ether and the solution was washed twice in each case with saturated NaHCO$_3$ solution and with KHSO$_4$/K$_2$SO$_4$ solution. The organic phase was dried over sodium sulfate and, after filtration, the solvent was removed in vacuo. The residue was dissolved in ethyl acetate and hydrogenated in the presence of palladium/carbon (10% strength; 50% water). The catalyst was filtered off and the organic phase was treated with 500 ml of water and 4.5 g of NaHCO$_3$. After extraction by shaking and phase separation, the aqueous phase was stirred at 100° C. for 2 hours. 3.39 g of Na$_2$CO$_3$ were added and the solution was stirred at 100° C. for 8 hours. After allowing to stand overnight, 500 ml of 6 N hydrochloric acid were added and the aqueous phase was extracted with methyl tert-butyl ether. The phases were separated and the organic phase was washed with water, dried over sodium sulfate and, after filtration, concentrated in vacuo. The residue was triturated with heptane and the product was filtered off. 3.7 g (83%) of (S)-2-(4,4-pentamethylene-2,5-dioxoimidazolidin-1-yl)-2-cyclopropylmethylacetic acid were obtained.

Example 40

(S)-3-((S)-2-(4,4-Pentamethylene-3-(4-(3-(2-methylphenyl)ureido)benzyl)-2,5-dioxoimidazolidin-1-yl)-2-cyclopropylmethylacetylamino)-3-(2,4-dimethoxyphenyl)propionic acid

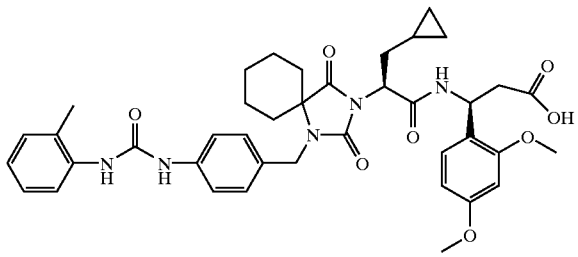

The compound was prepared analogously to Example 1 from 522 mg (1 mmol) of (S)-2-(4,4-pentamethylene-3-(4-(3-(2-methylphenyl)ureido)benzyl)-2,5-dioxoimidazolidin-1-yl)-2-cyclopropylmethylacetic acid (preparation see Example 39) and 284 mg (1 mmol) of tert-butyl (S)-3-amino-3-(2,4-dimethoxyphenyl)propionate. After coupling, chromatographic purification of the coupling product, cleavage of the tert-butyl ester using 90% strength trifluoroacetic acid, removal of the trifluoroacetic acid in vacuo, taking-up of the residue in dichloromethane, washing the dichloromethane phase three times with water, removal of the dichloromethane in vacuo and subsequent freeze drying, 590 mg (81%) of the title compound were obtained.

ES(+)-MS: 726.3 $(M+H)^+$.

Example 41

(S)-3-((S)-2-(4,4-Pentamethylene-3-(4-(3-(2-methylphenyl)ureido)benzyl)-2,5-dioxoimidazolidin-1-yl)-2-cyclopropylmethylacetylamino)-3-(2,4-dimethoxyphenyl)propionic acid sodium salt

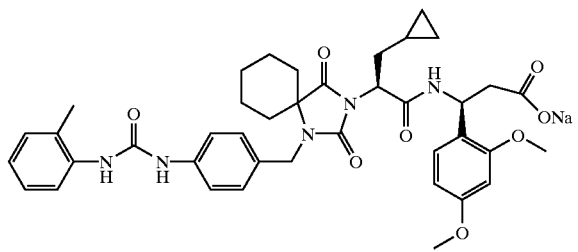

7.07 ml of 0.1 N sodium hydroxide solution were added in portions with stirring to a suspension of 540 mg (0.74 mmol) of (S)-3-((S)-2-(4,4-pentamethylene-3-(4-(3-(2-methylphenyl)ureido)benzyl)-2,5-dioxoimidazolidin-1-yl)-2-cyclopropylmethylacetylamino)-3-(2,4-dimethoxyphenyl)propionic acid in 20 ml of water and the mixture was stirred at room temperature for 1 hour. After filtration and freeze drying of the filtrate, 524 mg (95%) of the title compound were obtained.

ES(+)-MS: 726.3 ((S)-3-((S)-2-(4,4-pentamethylene-3-(4-(3-(2-methylphenyl)ureido)benzyl)-2,5-dioxoimidazolidin-1-yl)-2-cyclopropylmethylacetylamino)-3-(2,4-dimethoxyphenyl)propionic acid+H)$^+$, 748.3 $(M+H)^+$.

Investigation of the Biological Activity

A) U937/VCAM-1 Cell Adhesion Test

The test method used for the activity of the compounds of the formula I on the interaction between VCAM-1 and VLA-4 is the assay described below, which is specific for this interaction. The cellular binding components, that is the VLA-4 integrins, are supplied in their natural form as surface molecules on human U937 cells (ATCC CRL 1593), which belong to the leukocytes group. The specific binding components used are genetically engineered recombinant soluble fusion proteins, consisting of the extracytoplasmic domain of human VCAM-1 and the constant region of a human immunoglobulin of the subclass IgG1.

Assay for the Measurement of the Adhesion of U937 Cells (ATCC CRL 1593) to hVCAM-1 (1-3)-IgG 1. Preparation of Human VCAM-1(1-3)-IgG and Human CD4-IgG A genetic construct for the expression of the extracellular domain of human VCAM-1, combined with the genetic sequence of the heavy chain of human immunoglobulin IgG1 (hinge, CH2 and CH3 regions) (from Brian Seed, Massachusetts General Hospital, Boston, USA; cf. Damle and Aruffo, Proc. Natl. Acad. Sci. USA 1991, 88, 6403), was employed. The soluble fusion protein hVCAM-1(1-3)-IgG contained the three aminoterminal extracellular immunoglobulin-like domains of human VCAM-1 (Damle and Aruffo, Proc. Natl. Acad. Sci. USA 1991, 88, 6403). CD4-IgG (Zettlmeissl et al., DNA and Cell Biology 1990, 9, 347) served as a fusion protein for negative controls. The recombinant proteins were expressed as soluble proteins after DEAE/dextran-mediated DNA transfection in COS cells (ATCC CRL1651) according to standard procedures (Ausubel et al., Current protocols in molecular biology, John Wiley & Sons, Inc., 1994).

2. Assay for the Measurement of the Adhesion of U937 Cells to hVCAM-1(1-3)-IgG 2.1 96-well microtiter test plates (Nunc Maxisorb) were incubated at room temperature for 1 hour with 100 µl/well of a goat-anti-human IgG antibody solution (10 µg/ml in 50 mM tris, pH 9.5). After removal of the antibody solution, washing was carried out once with PBS.

2.2 150 µl/well of a blocking buffer (1% BSA in PBS) were incubated on the plates at room temperature for 0.5 hour. After removal of the blocking buffer, washing was carried out once with PBS.

2.3 100 µl per well of a cell culture supernatant of transfected COS cells were incubated on the plates at room temperature for 1.5 hours. The COS cells were transfected with a plasmid which codes for the three N-terminal immunoglobulin-like domains of VCAM-1, coupled to the Fc portion of human IgG$_1$ (hVCAM-1 (1-3)-IgG). The content of hVCAM-1(1-3)-IgG was about 0.5–1 µg/ml. After removing the culture supernatant, washing was carried out once with PBS.

2.4 The plates were incubated at room temperature for 20 minutes with 100 µl/well of Fc receptor blocking buffer (1 mg/ml of γ-globulin, 100 mM NaCl, 100 µM MgCl$_2$, 100 µM MnCl$_2$, 100 µM CaCl$_2$, 1 mg/ml of BSA in 50 mM HEPES, pH 7.5). After removal of the Fc receptor blocking buffer, washing was carried out once with PBS.

2.5 20 µl of binding buffer (100 µM NaCl, 100 µM MgCl$_2$, 100 µM MnCl$_2$, 100 µM CaCl$_2$, 1 mg/ml of BSA in 50 mM HEPES, pH 7.5) were initially introduced, and the substances to be tested were added in 10 µl of binding buffer and incubated for 20 minutes. The controls used were antibodies against VCAM-1(BBT, No. BBA6) and against VLA-4 (Immunotech, No. 0764).

2.6 U937 cells were incubated in Fc receptor blocking buffer for 20 minutes and then pipetted in at a concentration of 1×10$^6$/ml and in an amount of 100 µl per well (final volume 125 µl/well).

2.7 The plates were slowly immersed at an angle of 45° in stop buffer (100 mM NaCl, 100 µM MgCl$_2$, 100 µM MnCl$_2$, 100 µM CaCl$_2$ in 25 mM Tris, pH 7.5) and shaken off. The process was repeated.

2.8 50 µl/well of a dye solution (16.7 pg/ml of Hoechst Dye 33258, 4% formaldehyde, 0.5% Triton X-100 in PBS) were then incubated on the plates for 15 minutes.

2.9 The plates were shaken off and slowly immersed at an angle of 45° in stop buffer (100 mM NaCl, 100 µM MgCl$_2$, 100 µM MnCl$_2$, 100 µM CaCl$_2$ in 25 mM Tris, pH 7.5). the process was repeated. Then, with the liquid (stop buffer) present, the plates were measured in a cytofluorimeter (Millipore) (sensitivity: 5, filter: excitation wavelength: 360 nm, emission wavelength: 460 nm) with the liquid present (stop buffer).

The intensity of the light emitted from the stained U937 cells is a measure of the number of U937 cells adhered to the hVCAM-1(1-3)-IgG and remaining on the plate and thus a measure of the ability of the added test substance to inhibit this adhesion. From the inhibition of the adhesion at various concentrations of the test substance, the concentration IC$_{50}$ was calculated which leads to an inhibition of adhesion by 50%.

3. Results

The following test results were obtained in the U937/VCAM-1 cell adhesion test (IC$_{50}$ values in nM (nanomol/liter).

| Compound of Example No. | IC$_{50}$ (nM) |
|---|---|
| 1 | 3.2 |
| 2 | 4.5 |
| 3 | 17 |
| 4 | 85.4 |
| 8 | 3.2 |
| 9 | 2.2 |
| 16 | 4 |
| 17 | 1.9 |
| 18 | 2.4 |
| 19 | 3 |
| 20 | 1.6 |
| 21 | 3 |
| 22 | 6.7 |
| 23 | 5.5 |
| 24 | 1.7 |
| 25 | 1.1 |
| 26 | 2.6 |
| 27 | 3.4 |
| 28 | 2.1 |
| 29 | 1.9 |
| 30 | 3.6 |
| 31 | 0.8 |
| 32 | 0.6 |
| 33 | 1.3 |
| 34 | 1.8 |
| 35 | 3.4 |
| 37 | 1.3 |
| 38 | 1.6 |
| 39 | 0.8 |
| 40 | 2.1 |
| 41 | 2.3 |

The pharmacological properties of the compounds of the formula I can also be investigated in the following models.

B) Leukocyte Adhesion in Rats

In this model of leukocyte adhesion, the effect on the adhesion of leukocytes by the compounds of the formula I in venules of rats is investigated. The leukocyte adhesion to the endothelium of postcapillary venules is regarded as an important step in inflammatory reactions (J. M. Harlan, Blood 1985, 65, 513). In the recruitment of leukocytes from the blood into inflamed areas, a well-coordinated dynamic sequence of events takes place in which chemotactic cytokines and cellular adhesion molecules play an active part. It has been found that VCAM-1/VLA-4 interactions play a crucial role in the adhesion and emigration of leukocytes and the increased permeability of vessels for macromolecules which are induced by various mediator substances and cytokines (D. Seiffge, Int. J. Microcirc. 1995, 15, 301). In the present model, a generalized inflammation or rheumatoid arthritis which leads to adhesion of the leukocytes and their emigration into diseased areas of the organ, is caused by local or systemic injection of endotoxins, for example zymosan, bacterial toxins such as lipopolysaccharides (LPS) of Freund's adjuvant. The increased adhesion to the endothelium of the venules produced by the endotoxin is determined.

For the determination of the leukocyte adhesion, a camera inverted microscope (Zeiss) which is equipped with a video system is used. Male Sprague-Dawley rats (body weight about 250 g) are injected with zymosan or bacterial endotoxin under a slight halothane premedication. The control animals receive an identical volume of 0.9% strength saline solution. The test substance is then administered to the animals subcutaneously or orally as an individual dose or as a multiple dose. For carrying out the measurement, the rats are anesthetized by an intramuscular injection of 1.25 g/kg of urethane. They are allowed to breathe spontaneously through a tracheal tube. The body temperature is kept at 37° C. by means of a regulated heating pad. The mesentery is carefully exposed by means of a hypogastric incision on a thermostated (37° C.) window of the microscope stage, and is covered with liquid paraffin at 37° C. The ileocecal area of the mesentery is held in position with three blunt needles and modeling clay. After a 30-minute equilibration time, during which the tissue is allowed to stabilize, the leukocyte adhesion is determined in postcapillary venules of 20–30 µm diameter and about 100 µm length by counting in 2–3 segments of the venules over 1 hour at intervals of 10 minutes. A leukocyte is regarded as adherent to the endothelium if it is stationary for more than 30 seconds. After the experiment, the systemic leukocyte count and the fibrinogen content of the blood is determined. The inhibition of leukocyte adhesion by the test substance is indicated by the decrease (in %) of the number of adherent leukocytes in the treated animals in comparison with the number in the control animals.

C) Delayed-type Hypersensitivity in Mice

In the model of delayed-type hypersensitivity (DTH model), the antiallergic or antiinflammatory action of the compounds of the formula I is investigated. DTH is an inflammatory reaction of the skin which is induced by sensitization with antigenic substances. In order to determine the corresponding inflammatory reaction and the leukocyte recruitment in the inflamed areas in vivo, the substances are tested in the following DTH model in mice (see also T. B. Issekutz, J. Immunol. 1991, 147, 4178).

Groups of female BALB/c mice (body weight about 20 g) are sensitized epicutaneously on a shaved part of the skin with 150 µl of a 3% strength solution of oxazolone, which has been known to induce a strong inflammatory DTH reaction. 6 days later, the reaction is challenged by administration of 20 µl of a 1% strength oxazolone solution on the right ear of the animals. The test substances are administered subcutaneously or orally in each case 44 hours before the challenge of the reaction, 20 hours before the challenge and 4 hours after the challenge. Directly before the challenge of the reaction and 24 hours after the challenge, the altered ear thickness due to the inflammatory swelling of the ear is measured on the right ear using a Mitutoyo Engineering micrometer. The difference between these two measurements is determined for each animal of the group. The mean values of the differences of an animal group treated with the test substance on the one hand and an untreated control group on the other hand are compared. The percentage inhibition of ear swelling is indicated as a measure of the effect of the substance.

D) Anti-asthmatic Action in Guinea Pigs

The effects on the lung function and the anti-asthmatic action of the compounds of the formula I can be determined in a model guinea pigs which follows the method described by G. Moacevic, Arch. Toxicol. 1975, 34, 1. For this, the technical preparations for the investigation are carried out corresponding to the details described by Moacevic. Male albino guinea pigs having a body weight of 300–500 g are employed. The animals are placed in a plethysmograph (FMI) and three starting values of the parameters respiratory rate and respiratory amplitude are recorded. In this model, an asthmatic respiration is characterized by the decrease in the respiratory amplitude (=lowering of the respiratory volume on account of the bronchoconstriction) and the increase in the respiratory frequency (=reflex reaction). This condition is known in asthma patients as dyspnoea.

22 days before the start of the study, the albino guinea pigs are sensitized with 1 ml per animal of a 0.1% strength ovalbumin solution on two successive days. The experimental asthma attack is induced by inhalation of a 0.3% strength ovalbumin solution for 1 minute. After a recovery phase of 40–60 minutes, the animals inhale the test substance as an aqueous solution. Immediately afterwards, 0.3% strength ovalbumin solution is administered for 1 minute. In the following recovery phase of 30 minutes, the animals breathe normal air. This process is repeated twice. If the asthma attacks become life-threatening, oxygen is administered to the animals.

German Patent Application No. 199 22 462.5, filed on May 17, 1999, including the specification, figures, and abstract, is expressly incorporated by reference in its entirety.

The compounds, compositions, methods of preparation and methods for treating subjects described above are but some of many compounds, compositions, methods of preparation and methods for treating subjects that are within the scope of the present invention. Accordingly, the above description is only illustrative of preferred embodiments which can achieve the features and advantages of the present invention. It is not intended that the invention be limited to the embodiments described in detail herein. The invention is only limited by the scope of the following claims.

We claim:

1. A compound of the formula I, or a physiologically acceptable salt thereof, or a stereoisomeric form or mixture thereof, or a prodrug thereof, wherein the compound has the formula:

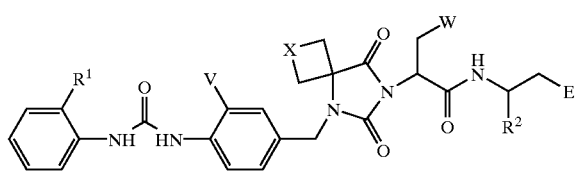

and wherein:

$R^1$ is hydrogen or methyl;

$R^2$ is unsubstituted phenyl, substituted phenyl or $(C_1-C_4)$-alkyl;

X is $-CH_2-CH_2-$ or $-CH_2-CH_2-CH_2-$, where one of the $CH_2$ groups in these two residues is optionally replaced by a carbonyl group $C=O$;

W is isopropyl or cyclopropyl;

V is hydrogen or methoxy;

E is $-CO-R^3$, $-CO-H$, $-CH_2-O-R^4$, $-CH_2-O-CO-R^4$, $-CH_2-O-CO-O-R^5$ or 5-tetrazolyl;

$R^3$ is hydroxy, $(C_1-C_{10})$-alkoxy, phenyl-$(C_1-C_8)$-alkoxy-, phenyloxy-, $(C_1-C_8)$-alkylcarbonyloxy-$(C_1-C_6)$-alkoxy-, phenylcarbonyloxy-$(C_1-C_6)$-alkoxy-, phenyl-$(C_1-C_6)$-alkylcarbonyloxy-$(C_1-C_6)$-alkoxy-, $(C_1-C_8)$-alkoxycarbonyloxy-$(C_1-C_6)$-alkoxy-, phenyloxycarbonyloxy-$(C_1-C_6)$-alkoxy-, phenyl-$(C_1-C_6)$-alkoxycarbonyloxy-$(C_1-C_6)$-alkoxy-, amino, mono-$((C_1-C_{10})$-alkyl)-amino-, di-$((C_1-C_{10})$-alkyl)-amino- or $R^4R^4N-CO-(C_1-C_6)$-alkoxy- in which the residues $R^4$ are independent of one another and may be identical or different, wherein each phenyl residue of $R^3$ is unsubstituted phenyl or substituted phenyl;

$R^4$ is hydrogen, $(C_1-C_{10})$-alkyl, unsubstituted phenyl, substituted phenyl or phenyl-$(C_1-C_8)$-alkyl-, wherein the phenyl residue is unsubstituted phenyl or substituted phenyl;

$R^5$ has one of the meanings of $R^4$ with the proviso that $R^4$ is not hydrogen;

wherein substituted phenyl residue is substituted by one or more identical or different substituents from the group consisting of $(C_1-C_4)$-alkyl, $(C_1-C_4)$-alkoxy, methylenedioxy, ethylenedioxy, halogen, trifluoromethyl and trifluoromethoxy.

2. The compound set forth in claim 1, wherein W is isopropyl and V is hydrogen.

3. The compound set forth in claim 1, wherein $R^2$ is selected from the group consisting of unsubstituted phenyl, phenyl substituted with a methylenedioxy residue, phenyl substituted with an ethylenedioxy residue, phenyl substituted by one or two $(C_1-C_4)$-alkoxy groups, and $(C_1-C_4)$-alkyl.

4. The compound set forth in claim 1, wherein E is selected from the group consisting of $-CO-R^3$ or $-CH_2-OH$, where $R^3$ is hydroxy, $(C_1-C_6)$-alkoxy or amino.

5. The compound set forth in claim 1, wherein $R^2$ is selected from the group consisting of unsubstituted phenyl, phenyl substituted by a methylenedioxy residue, phenyl substituted by an ethylenedioxy residue, phenyl substituted by one or two methoxy groups, and $(C_1-C_4)$-alkyl; and E is selected from the group consisting of $-CO-OH$, $-CO-O-(C_1-C_4)$-alkyl, $-CO-NH_2$ and $-CH_2-OH$.

6. The compound set forth in claim 1, wherein W is isopropyl; V is hydrogen;

R$^2$ is selected from the group consisting of unsubstituted phenyl, phenyl substituted by a methylenedioxy residue, phenyl substituted by an ethylenedioxy residue, phenyl substituted by one or two methoxy groups, and (C$_1$–C$_4$)-alkyl; and E is selected from the group consisting of —CO—OH, —CO—O—(C$_1$–C$_4$)-alkyl, —CO—NH$_2$ and —CH$_2$—OH.

7. The compound set forth in claim 1, or a physiologically acceptable salt thereof, or a stereoisomeric form or a mixture thereof wherein said compound is selected from the group consisting of:

3-(2-(4,4-pentamethylene-3-(4-(3-phenylureido)benzyl)-2,5-dioxoimidazolidin--yl)-2-(2-methylpropyl)acetylamino)-3-phenylpropionic acid, 3-(2-(4,4-pentaethylene-3-(4-(3-phenylureido)benzyl)-2,5-dioxoimidazolidin-1-yl)-2-(2-methylpropyl)acetylamino)-3-methylpropionic acid, 3-(2-(4,4-pentamethylene-3-(4-(3-phenylureido)benzyl)-2,5-dioxoimidazolidin-1-yl)-2-(2-methylpropyl)acetylamino)-3-(2-methylpropyl)propionic acid, 3-(2-(4,4-pentamethylene-3-(4-(3-(2-methylphenyl)ureido)benzyl)-2,5-dioxoimidazolidin-1-yl)-2-(2-methylpropyl)acetylamino)-3-phenylpropionic acid, 3-(2-(4,4-pentamethylene-3-(4-(3-(2-methylphenyl)ureido)benzyl)-2,5-dioxoimidazolidin-1-yl)-2-(2-methylpropyl)acetylamino)-3-methylpropionic acid, 3-(2-(4,4-pentamethylene-3-(4-(3-(2-methylphenyl)ureido)benzyl)-2,5-dioxoimidazolidin-1-yl)-2-(2-methylpropyl)acetylamino)-3-(2-methylpropyl)propionic acid, 3-(2-(4,4-Pentamethylene-3-(4-(3-phenylureido)benzyl)-2,5-dioxoimidazolidin-1-yl)-2-(2-methylpropyl)acetylamino)-3-methylpropionamide, 3-(2-(4,4-Pentamethylene-3-(4-(3-phenylureido)benzyl)-2,5-dioxoimidazolidin-1-yl)-2-(2-methylpropyl)acetylamino)-3-phenylpropionamide, 3-(2-(4,4-Pentamethylene-3-(4-(3-phenylureido)benzyl)-2,5-dioxoimidazolidin-1-yl)-2-(2-methylpropyl)acetylamino)-3-(2,4-dimethoxyphenyl)propionic acid, 3-(2-(4,4-Pentamethylene-3-(4-(3-phenylureido)benzyl)-2,5-dioxoimidazolidin-1-yl)-2-(2-methylpropyl)acetylamino)-3-(3,4-dimethoxyphenyl)propionic acid, 3-(2-(4,4-Pentamethylene-3-(4-(3-(2-methyphenyl)ureido)benzyl)-2,5-dioxoimidazolidin-1-yl)-2-(2-methylpropylacetylamino)-3-(2,4-dimethoxyphenyl)propionic acid, 3-(2-(4,4-Pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid, 3-(2-(4,4-Pentamethylene-3-(4-(3-(2-methylphenyl)ureido)benzyl)-2,5-dioxoimidazolidin-1-yl)-2-(2-methylpropyl)acetylamino)-3-methylpropionamide, 3-(2-(4,4-Pentamethylene-3-(4-(3-(2-methylphenyl)ureido)-3-methoxybenzyl)-2,5-dioxoimidazolidin-1-yl)-2-(2-methylpropyl)acetylamino)-3-(3,4-dimethoxyphenyl)propionic acid, 3-(2-(4,4-Pentamethylene-3-(4-(3-(2-methylphenyl)ureido)benzyl)-2,5-dioxoimidazolidin-1-yl)-2-cyclopropylmethylacetylamino)-3-(3,4-dimethoxyphenyl)propionic acid, and 3-(2-(4,4-Pentamethylene-3-(4-(3-(2-methylphenyl)ureido)benzyl)-2,5-dioxoimidazolidin-1-yl)-2-cyclopropylmethylacetylamino)-3-(2,4-dimethoxyphenyl)propionic acid.

8. The compound set forth in claim 1, or a physiologically acceptable salt thereof, wherein said compound is selected from the group consisting of:

(S)-3-((S)-2-(4,4-pentamethylene-3-(4-(3-phenylureido)benzyl)-2,5-dioxoimidazolidin-1-yl)-2-(2-methylpropyl)acetylamino)-3-phenylpropionic acid, (R)-3-((S)-2-(4,4-pentamethylene-3-(4-(3-phenylureido)benzyl)-2,5-dioxoimidazolidin-1-yl)-2-(2-methylpropyl)acetylamino)-3-methyl propionic acid, (R)-3-((S)-2-(4,4-pentamethylene-3-(4-(3-phenylureido)benzyl)-2,5-dioxoimidazolidin-1-yl)-2-(2-methylpropyl)acetylamino)-3-(2-methylpropyl)propionic acid, (S)-3-((S)-2-(4,4-pentamethylene-3-(4-(3-(2-methylphenyl)ureido)benzyl)-2,5dioxoimidazolidin-1-yl)-2-(2-methylpropyl)acetylamino)-3-phenylpropionic acid, (R)-3-((S)-2-(4,4-pentamethylene-3-(4-(3-(2-methylphenyl)ureido)benzyl)-2,5dioxoimidazolidin-1-yl)-2-(2-methylpropyl)acetylamino)-3-methylpropionic acid, (R)-3-((S)-2-(4,4-pentamethylene-3-(4-(3-(2-methylphenyl)ureido)benzyl)-2,5dioxoimidazolidin-1-yl)-2-(2-methylpropyl)acetylamino)-3-(2-methylpropyl)propionic acid, (R)-3-((S)-2-(4,4-Pentamethylene-3-(4-(3-phenylureido)benzyl)-2,5-dioxoimidazolidin-1-yl)-2-(2-methylpropyl)acetylamino)-3-methylpropionamide, (S)-3-((S)-2-(4,4-Pentamethylene-3-(4-(3-phenylureido)benzyl)-2,5-dioxoimidazolidin-1-yl)-2-(2-methylpropyl)acetylamino)-3-phenylpropionamide, (S)-3-((S)-2-(4,4-Pentamethylene-3-(4-(3-phenylureido)benzyl)-2,5-dioxoimidazolidin-1-yl)-2-(2-methylpropyl)acetylamino)-3-(2,4-dimethoxyphenyl)propionic acid, (S)-3-((S)-2-(4,4-Pentamethylene-3-(4-(3-phenylureido)benzyl)-2,5-dioxoimidazolidin-1-yl)-2-(2-methylpropyl)acetylamino)-3-(3,4-dimethoxyphenyl)propionic acid, (S)-3-((S)-2-(4,4-Pentamethylene-3-(4-(3-(2-methyphenyl)ureido)benzyl)-2,5-dioxoimidazolidin-1-yl)-2-(2-methylpropyl)acetylamino)-3-(2,4-dimethoxyphenyl)propionic acid, (S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-(3,4-dimethoxyphenyl)propionic acid, (R)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-methylpropionamide, (S)-3-((S)-2-(4,4-Pentamethylene-3-(4-(3-(2-methylphenyl)ureido)-3-methoxybenzyl)-2,5-dioxoimidazolidin-1-yl)-2-(2-methylpropyl)acetylamino)-3-(3,4-dimethoxyphenyl)propionic acid, (S)-3-((S)-2-(4,4-Pentamethylene-3-(4-(3-(2-methylphenyl)ureido)benzyl)-2,5-dioxoimidazolidin-1-yl)-2-cyclopropylmethylacetylamino)-3-(3,4-dimethoxyphenyl)propionic acid, and (S)-3-((S)-2-(4,4-Pentamethylene-3-(4-(3-(2-methylphenyl)ureido)benzyl)-2,5-dioxoimidazolidin-1-yl)-2-cyclopropylmethylacetylamino)-3-(2,4-dimethoxyphenyl)propionic acid.

9. The compound set forth in claim 1, wherein said compound is selected from the group consisting of:

(S)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-phenylpropionic acid tromethamine salt, (R)-3-((S)-2-(4,4-Pentamethylene-3-(4-(3-(2-methylphenyl)ureido)benzyl)-2,5-dioxoimidazolidin-1-yl)-2-(2-methylpropyl)acetylamino)-3-methylpropionic acid tromethamine salt, (S)-3-((S)-2-(4,4-Pentamethylene-3-(4-(3-(2-methylphenyl)ureido)benzyl-2,5-dioxoimidazolidin-1-yl)-2-(2- methylpropyl)acetylamino)-3-(2,4-dimethoxyphenyl) propionic acid tromethamine salt, (S)-3-((S)-2-(4,4-Pentamethylene-3-(4-(3-(2-methylphenyl) ureido)benzyl)-2,5dioxoimidazolidin-1-yl)-2-(2-methylpropyl)acetylamino)-3-(2,4-dimethoxyphenyl) propionic acid sodium salt, (S)-3-((S)-2-(4,4-Pentamethylene-3-(4-(3-(2-methylphenyl) ureido)benzyl)-2,5-dioxoimidazolidin-1-yl)-2-(2-methylpropyl)acetylamino)-3-(3,4-dimethoxyphenyl) propionic acid tromethamine salt, (S)-3-((S)-2-(4,4-Pentamethylene-3-(4-(3-(2-methylphenyl) ureido)benzyl)-2,5-dioxoimidazolidin-1-yl)-2-(2-methylpropyl)acetylamino)-3-(3,4-dimethoxyphenyl) propionic acid sodium salt, (S)-3-((S)-2-(4,4-Pentamethylene-3-(4-(3-(2-methylphenyl) ureido)-3-methoxybenzyl-2,5-dioxoimidazolidin-1-yl)-2-(2-methylpropyl)acetylamino)-3-(3,4-dimethoxyphenyl) propionic acid tromethamine salt, and (S)-3-((S)-2-(4,4-Pentamethylene-3-(4-(3-(2-methylphenyl) ureido)benzyl)-2,5-dioxoimidazolidin-1-yl)-2-cyclopropylmethylacetylamino)-3-(2,4-dimethoxyphenyl)propionic acid sodium salt.

10. A process for preparing a compound of the formula I as set forth in claim 1, said process comprising carrying out a condensation of a compound of the formula II with a compound of the formula III

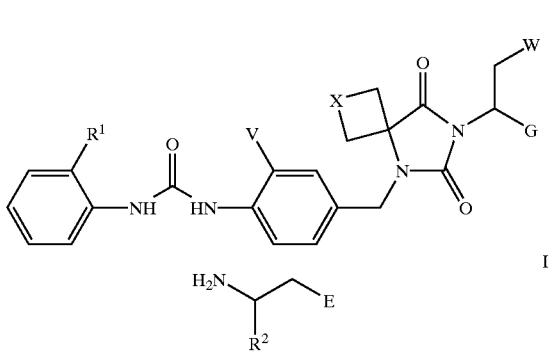

where, in the formulae II and III, the groups E, V, W, X, $R^1$ and $R^2$ are defined as set forth in claim 1 or, alternatively functional groups are present in protected form or in the form of precursors, and wherein G is hydroxycarbonyl, $(C_1-C_6)$-alkoxycarbonyl or a carboxylic acid active ester or a carboxylic acid chloride.

11. A pharmaceutical preparation, which comprises one or more compounds of the formula I as set forth in claim 1, a physiologically acceptable salt thereof and/or a prodrug thereof, and a pharmaceutically acceptable carrier.

12. A method for the treatment of inflammatory disorders which comprises administering to a subject in need thereof an effective amount of a composition comprising one or more compounds of the formula I set forth in claim 1, a physiologically acceptable salt thereof and/or a prodrug thereof, and a pharmaceutically acceptable carrier.

13. A method for the treatment of arthritis, rheumatoid arthritis, polyarthritis, inflammatory bowel disease, systemic lupus erythematosus, multiple sclerosis or inflammatory disorders of the central nervous system which comprises administering to a subject in need thereof an effective amount of a composition comprising one or more compounds of the formula I as set forth in claim 1, a physiologically acceptable salt thereof and/or a prodrug thereof, and a pharmaceutically acceptable carrier.

14. A method for the treatment of asthma or allergies which comprises administering to a subject in need thereof an effective amount of a composition comprising one or more compounds of the formula I as set forth in claim 1, a physiologically acceptable salt thereof and/or a prodrug thereof, and a pharmaceutically acceptable carrier.

15. A method for the treatment of cardiovascular disorders, arteriosclerosis, restenoses, diabetes, damage to organ transplants, immune disorders, autoimmune disorders, tumor growth or metastasis, or malaria which comprises administering to a subject in need thereof an effective amount of a composition comprising one or more compounds of the formula I as set forth in claim 1, a physiologically acceptable salt thereof and/or a prodrug thereof, and a pharmaceutically acceptable carrier.

16. A method for inhibiting the adhesion and/or migration of leukocytes which comprises administering to a subject in need thereof an effective amount of a composition comprising one or more compounds of the formula I as set forth in claim 1, a physiologically acceptable salt thereof and/or a prodrug thereof, and a pharmaceutically acceptable carrier.

17. A method for the inhibition of the VLA-4 receptor which comprises administering to a subject in need thereof an effective amount of a composition comprising one or more compounds of the formula I as set forth in claim 1, a physiologically acceptable salt thereof and/or a prodrug thereof, and a pharmaceutically acceptable carrier.

* * * * *